(12) United States Patent
Sole Feu et al.

(10) Patent No.: US 10,173,985 B2
(45) Date of Patent: Jan. 8, 2019

(54) AMINOINDAZOLE DERIVATIVES AS SODIUM CHANNEL INHIBITORS

(71) Applicant: ALMIRALL, S.A., Barcelona (ES)

(72) Inventors: Laia Sole Feu, Barcelona (ES); Silvia Fonquerna Pou, Barcelona (ES)

(73) Assignee: Almirall, S.A., Barcelona (ES)

( * ) Notice: Subject to any disclaimer, the term of this patent is extended or adjusted under 35 U.S.C. 154(b) by 0 days.

(21) Appl. No.: 15/559,120

(22) PCT Filed: Mar. 22, 2016

(86) PCT No.: PCT/EP2016/056273
§ 371 (c)(1),
(2) Date: Sep. 18, 2017

(87) PCT Pub. No.: WO2016/150971
PCT Pub. Date: Sep. 29, 2016

(65) Prior Publication Data
US 2018/0244626 A1   Aug. 30, 2018

(30) Foreign Application Priority Data

Mar. 24, 2015 (EP) ..................................... 15382139

(51) Int. Cl.
| | |
|---|---|
| *C07D 231/56* | (2006.01) |
| *C07D 401/04* | (2006.01) |
| *C07D 405/10* | (2006.01) |
| *C07D 471/04* | (2006.01) |
| *C07D 487/04* | (2006.01) |
| *A61K 31/416* | (2006.01) |
| *A61K 45/06* | (2006.01) |
| *A61K 31/454* | (2006.01) |
| *A61K 31/4545* | (2006.01) |
| *A61K 31/437* | (2006.01) |
| *A61K 31/4985* | (2006.01) |
| *A61K 31/5377* | (2006.01) |
| *A61K 31/4439* | (2006.01) |

(52) U.S. Cl.
CPC .......... *C07D 231/56* (2013.01); *A61K 31/416* (2013.01); *A61K 31/437* (2013.01); *A61K 31/4439* (2013.01); *A61K 31/454* (2013.01); *A61K 31/4545* (2013.01); *A61K 31/4985* (2013.01); *A61K 31/5377* (2013.01); *A61K 45/06* (2013.01); *C07D 401/04* (2013.01); *C07D 405/10* (2013.01); *C07D 471/04* (2013.01); *C07D 487/04* (2013.01)

(58) Field of Classification Search
None
See application file for complete search history.

(56) References Cited

U.S. PATENT DOCUMENTS

| | | |
|---|---|---|
| 2004/0235892 A1 | 11/2004 | Dai et al. |
| 2010/0113415 A1 | 5/2010 | Rajapakse et al. |

FOREIGN PATENT DOCUMENTS

| | | |
|---|---|---|
| WO | WO 2012/007861 A1 | 1/2012 |
| WO | WO 2012/095781 A1 | 7/2012 |

OTHER PUBLICATIONS

International Search Report for International Application No. PCT/EP2016/056273, dated May 3, 2016.
Written Opinion of the International Searching Authority for International Application No. PCT/EP2015/056273.

*Primary Examiner* — Alicia L Otton
(74) *Attorney, Agent, or Firm* — Finnegan, Henderson, Farabow, Garrett & Dunner, LLP

(57) ABSTRACT

The present invention relates to novel aminoindazolyl derivative compounds of Formula (I), the use of said compounds in treating diseases mediated by modulation of voltage-gated sodium channels in particular Nav 1.7, to compositions containing said derivatives and processes for their preparation.

Formula (I)

20 Claims, No Drawings

AMINOINDAZOLE DERIVATIVES AS SODIUM CHANNEL INHIBITORS

This application is a national stage filing under 35 U.S.C. § 371 of International Application No. PCT/EP2016/056273, filed on Mar. 22, 2016, which claims priority of European Patent Application No. 15382139.2, filed Mar. 24, 2015. The contents of these applications are each incorporated herein by reference.

FIELD OF THE INVENTION

The present invention relates to novel aminoindazolyl derivative compounds, the use of said compounds in treating diseases mediated by modulation of voltage-gated sodium channels in particular Nav1.7, to compositions containing said derivatives and processes for their preparation.

BACKGROUND OF THE INVENTION

Voltage-gated sodium channels have a relevant role in the initiation and propagation of electrical signalling in excitable cells. Genetic studies have proven that inherited disorders like cardiac arrhythmias, epilepsy and loss or gain of pain sensation could be linked to mutations of genes that encode Nav subtypes. (Nardi A. et al, *Chem Med Chem*, 2012, 7, 1-30).

There are nine subtypes of voltage-gated sodium channels in humans. Although they are very similar in sequence, different sodium channel subtypes have important and diverse physiological roles. Nav1.1, Nav1.2, and Nav1.3 are highly expressed in the central nervous system. Nav1.4 is primarily found in skeletal muscle and Nav1.5 is expressed mainly in the cardiac muscle. Nav1.6 is a widely expressed sodium channel and it can be found throughout the central and the peripheral nervous system. Nav1.7, Nav1.8 and Nav1.9 are found predominantly in peripheral sympathetic and sensory neurons.

Most of the small Nav1.7 inhibitors are known to bind a region of the channel in the inner vestibule of the pore on transmembrane S6 domain IV which is highly conserved between subtypes. However, it is possible to find selective Nav1.7 inhibitors.

A selective Nav1.7 would be highly desirable to avoid undesired adverse effects observed with existing non-selective Nav inhibitors such as Lidocaine which have a limited therapeutic window.

Particularly, finding selectivity of Nav1.7 with respect to Nav1.5 would be desirable to avoid any cardiovascular side effects.

State dependent inhibitors are thought to stabilise an inactivated conformation of the channel which is adopted rapidly after the channel opens. This inactivated state provides a refractory period before the channel returns to its resting state ready to be reactivated. State dependent inhibition is proposed to reflect an allosteric mechanism by which the drug receptor site is in the low-affinity conformation when the channel is at rest and converts into a high-affinity conformation when the channel is open or inactivated. This ability for sodium channels to adopt different conformations depending on the voltage would increase therapeutic index by enhancing functional selectivity as in healthy tissues sodium channels mostly reside in the resting state whereas inactivated state has a greater relevance in diseased tissue. (Priest B. T. et al, *Curr. Top. Med. Chem.* 2008, 3, 121-143, Ragsdale D. S., *Brain Res. Brain Res. Rev.* 1998, 26, 16-28, Yanagidate F., *Exp. Pharmacol.* 2007, 95-127).

Several studies relate gain-of-function mutations of the gene that encodes Nav1.7 to pain whereas loss-of-function mutations in this gene lead to an indifference to pain (Dib-Hajj, S. D et al, *Annu. Rev. Neurosci.* 2010, 33, 325-347). Additional studies have linked Nav1.7 to cough reflex (Muroi, Y. et al, *J. Physiol.* 2011, 589, 5663-5676).

Some modulators of voltage gated sodium channels in particular Nav1.7 were described in WO 2012/007861 and WO 2012/095781.

Other indazole and pyrazolo derivatives were described in the documents US 2004/235892 and US 2010/113415, although these compounds are useful as a modulators of tyrosin kinases.

Nav1.7 inhibitors are potentially useful in the treatment of a wide range of disorders, such as pain, including but not limited to acute pain, chronic pain, inflammatory pain, visceral pain, nociceptive pain, neuropathic pain, postherpethic pain, trigeminal neuralgia, diabetic neuropathy, chronic back pain, chronic pelvic pain, pain resulting from cancer and chemotherapy, migraine, idiopathic cough, chronic cough or cough related to respiratory diseases, respiratory diseases, itch, dermatological diseases, epilepsy, squizophrenia and bipolar disorder. They can also be potentially used as analgesic and anaesthetic drugs.

We have now discovered novel aminoindazolyl derivative compounds as potent state dependent and selective Nav1.7 inhibitors.

SCOPE OF THE INVENTION

Accordingly, the present invention provides a compound of Formula (I), or a pharmaceutically acceptable salt, or N-oxide, or isotopically-labeled derivate thereof:

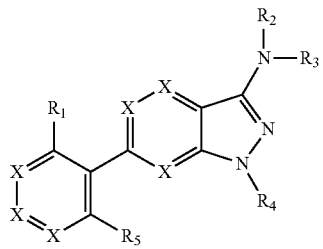

Formula (I)

wherein
each X independently represents a —N= or —CR$^C$=,
R$_1$ represents —R$^d$, or —O—R$^d$,
R$_2$ and R$_3$ independently are selected from the group consisting of a hydrogen atom, a lineal or branched C$_{1-4}$ alkyl group, a lineal or branched C$_{1-4}$ hydroxyalkyl group, a monocyclic C$_{3-7}$ cycloalkyl group optionally substituted with one or more substituents selected from a lineal or branched C$_{1-4}$ alkyl group and amino group; a monocyclic 4 to 7-membered heterocyclyl containing at least one heteroatom selected from N, S, and O, a lineal or branched C$_{1-4}$ alkylsulfonyl group, —(CH$_2$)$_p$—CO—(CH$_2$)$_q$—NH$_2$ group, —(CH$_2$)$_r$—NR$^a$R$^b$ group, —(CH$_2$)$_p$—R$^e$ group, —SO$_2$—NR$^a$R$^b$ group, and —CO—CF$_3$ group,
R$_4$ is selected from the group consisting of a lineal or branched C$_{1-4}$ alkyl group optionally substituted with one or more substituent selected from a halogen atom, —(CH$_2$)$_p$—CO—(CH$_2$)$_q$—NH$_2$ group, a lineal or branched C$_{1-4}$ hydroxyalkyl group, a lineal or branched C$_{1-4}$ aminoalkyl group, (C$_{1-2}$ alkoxy)-(C$_{1-2}$)alkyl group, —(CH$_2$)$_p$—R$^e$ group and —(CH$_2$)$_r$—NR$^a$R$^b$ group, R$_5$ is selected from the group consisting of a hydrogen atom and halogen atom, R$^a$ and R$^b$ independently represents a hydrogen atom or a lineal or branched C$_{1-4}$ alkyl group, or R$^a$ and R$^b$ together with N form a monocyclic 4 to 7-membered heterocyclyl and optionally containing at least one further heteroatom selected from N, S, and O, each R$^c$ independently represents a hydrogen atom, halogen atom, a lineal or branched C$_{1-4}$ alkyl group or a lineal or branched C$_{1-4}$ alkoxy group, R$^d$ represents a lineal or branched C$_{1-6}$ haloalkyl group, R$^e$ represents a monocyclic 6 to 8-membered heteroaryl group containing at least one heteroatom selected from N, S and O, a monocyclic 3 to 8-membered heterocyclyl group containing at least one heteroatom selected from N, S and O and optionally substituted with one or more substituents selected from a lineal or branched C$_{1-4}$ alkyl group, p and q independently have a value of 0, 1 or 2, r has a value of 1, 2, 3 or 4.

The invention further provides synthetic processes and intermediates described herein, which are useful for preparing said compounds.

The invention also provides a pharmaceutical composition comprising at least a compound of the invention and a pharmaceutically acceptable diluent or carrier.

The invention also provides a compound of the invention for use in the treatment of the human or animal body by therapy.

The invention is also directed to the compounds of the invention as described herein, for use in the treatment of a pathological condition or disease mediated by modulation of voltage-gated sodium channels in particular Nav1.7, which condition or disease is selected from pain, including but not limited to acute pain, chronic pain, inflammatory pain, visceral pain, nociceptive pain, neurophatic pain, postherpetic pain, trigeminal neuralgia, diabetic neuropathy, chronic back pain, chronic pelvic pain, pain resulting from cancer and chemotherapy, migraine, idiopathic cough, chronic cough or cough related to respiratory diseases, respiratory diseases, itch, dermatological diseases, epilepsy, squizophrenia and bipolar disorder. They can also be potentially used as analgesic and anaesthetic drugs.

The invention also provides the use of the compounds of the invention as described herein, for the manufacture of a medicament for the treatment of a pathological condition or disease mediated by modulation of voltage-gated sodium channels in particular Nav1.7, which condition or disease is selected from pain, including but not limited to acute pain, chronic pain, inflammatory pain, visceral pain, nociceptive pain, neurophatic pain, postherpetic pain, trigeminal neuralgia, diabetic neuropathy, chronic back pain, chronic pelvic pain, pain resulting from cancer and chemotherapy, migraine, idiopathic cough, chronic cough or cough related to respiratory diseases, respiratory diseases, itch, dermatological diseases, epilepsy, squizophrenia and bipolar disorder.

The invention is also directed to a method of treatment of a pathological condition or disease mediated by modulation of voltage-gated sodium channels in particular Nav1.7, which condition or disease is selected from pain, including but not limited to acute pain, chronic pain, inflammatory pain, visceral pain, nociceptive pain, neurophatic pain, postherpetic pain, trigeminal neuralgia, diabetic neuropathy, chronic back pain, chronic pelvic pain, pain resulting from cancer and chemotherapy, migraine, idiopathic cough, chronic cough or cough related to respiratory diseases, respiratory diseases, itch, dermatological diseases, epilepsy, squizophrenia and bipolar disorder, comprising administering a therapeutically effective amount of the compounds of the invention or a pharmaceutical composition of the invention to a subject in need of such treatment.

The invention also provides a combination product comprising (i) at least a compound of the invention as described herein; and (ii) one or more active ingredients selected from:

(a) Opioid receptor agonists such as but not restricted to morphine, phentanyl, hydromorphone or hydrocodone, (b) Opioid receptor partial agonists such as but not restricted to meptazinol, (c) NSAIDS such as but not restricted to acetyl salicilic acid, ibuprofen, naproxen, aceclofenac or diclofenac, (d) COX-2 inhibitors such as but not restricted to rofecoxib or celecoxib, (e) Ion channel modulators such as but not restricted to ziconotide or gabapentine, (f) Centrally acting agents such as but not restricted to flupirtine or neofam, (g) Agents for neuropathic pain such as but not restricted to carbamazepine, gabapentine, duloxetine or pregabaline, (h) Agents for cancer pain such as but not restricted to calcitonine, lexidronam or oxycodone for pain patients, (i) Anti-fibrotics such as but not restricted to pirfenidone, nintenadib for patients with idiopathic pulmonary fibrosis, (j) Prostacyclin analogues such as but not restricted to epoprostenol, beraprost, treprostinil or iloprost, (k) Endothelin antagonists such as but not restricted to bosentac, sitaxentan, ambrisentan or macitentan, (l) Phosphodiesterase V inhibitors such as but not restricted to sildenafil or taldenafil, (m) Guanylate cyclase stimulators such as but not restricted to riociguat for patients with pulmonary hypertension, (n) Oral and inhaled corticosteroids such as but not restricted to fluticasone, (o) Phosphodiesterase IV inhibitors like roflumilast, (p) Beta2-adrenoceptor agonists such as but not restricted to salbutamol, salmeterol, indacaterol or olodaterol, (q) Muscarinic antagonists such as but not restricted to ipratropium, tiotropium, aclidinium, glycopyrronium or umeclidinium, (r) Xantines such as but not restricted to teophyline, (s) Mast cell stabilizers such as but not restricted to tranilast and tazonilast, (t) Leukotriene modifiers such as but not restricted to montelukast, zafirlukast and zileuton, (u) Th2 cytokine inhibidors such as but not restricted to suplatast, (v) Thromboxane antagonists/thromboxane synthase inhibidors such as but not restricted to ozagrel and seratrodast, (w) Anti-IgE therapy compounds such as but not restricted to xolair for patients with asthma, (x) Histamine antagonists such as but not restricted to ebastine, cetiricine and loratadine, (y) Antiinflammatory agents such as NSAIDs, corticosteroids, calcineurin inhibitors, anti-TNF, anti-IL17, anti-IL12/IL13, anti-IL5, anti IL4/IL-13, anti-IL31 or anti-IgE antibodies, (z) JAK inhibidors such as but not restricted to ruxolitinib or tofacitinib, (aa) Syk inhibidors, (ab) Immunosupressants, (ac) Antipruritic agents such as kappa opioid agonists, mu opioid agonists, neurokinin receptor 1 antagonists such as but not restricted to aprepitant, 5-HT3 antagonists and cannabinoids (ad) Anti-tussive agents; Decongestants; Mucolytics; Expectorants or Proton Pump Inhibitors, for simultaneous, separate or sequential use in the treatment of the human or animal body.

DETAILED DESCRIPTION OF THE INVENTION

When describing the compounds, compositions and methods of the invention, the following terms have the following meanings, unless otherwise indicated.

As used herein the term $C_{1-4}$ alkyl embraces linear or branched radicals having 1 to 4 carbon atoms. Examples include methyl, ethyl, n-propyl, i-propyl, n-butyl, sec-butyl and t-butyl radicals.

As used herein, the term $C_{1-6}$ haloalkyl group is a $C_{1-6}$, preferably $C_{1-4}$ linear or branched alkyl group, which is substituted by one or more halogen atoms. Examples of said haloakyl group include, among others, —$CF_3$, —$CHFCF_3$, —$CF_2$—$CF_3$, —$CH_2CF_3$, —$CH_2CF_2CF_3$, —$CH_2CHF_2$ and —$CH_2CF_2CF_2CF_3$.

As used herein, the term $C_{1-4}$ alkoxy (or alkyloxy) embraces optionally substituted, linear or branched oxy-containing radicals each having alkyl portions of 1 to 4 carbon atoms. Examples include methoxy, ethoxy, n-propoxy, i-propoxy, n-butoxy, sec-butoxy and t-butoxy.

As used herein, the term $C_{1-4}$ aminoalkyl embraces radicals containing an optionally substituted, linear or branched alkyl radicals of 1 to 4 carbon atoms attached to a —$NH_2$ radical. Examples of $C_{1-4}$ aminoalkyl include methylamino, ethylamino, n-propylamino, i-propylamino, n-butylamino, sec-butylamino and t-butylamino.

As used herein, the term $C_{1-4}$ hydroxyalkyl embraces linear or branched alkyl radicals having 1 to 4 carbon atoms, any one of which may be substituted with one or more hydroxyl radicals. Examples of such radicals include hydroxymethyl, hydroxyethyl, hydroxypropyl, and hydroxybutyl.

As used herein, the term $C_{1-4}$ alkylsulfonyl embraces radicals containing a linear or branched alkyl radicals of 1 to 4 carbon atoms attached to a divalent —$SO_2$— radical.

As used herein, the term 6- to 8-membered heteroaryl radical embraces typically a monocyclic 6- to 8-membered ring system comprising one heteroaromatic ring and containing at least one heteroatom selected from O, S and N. Examples include pyridyl, pyrazinyl, pyrimidinyl, pyridazinyl, azepinyl, diazepinyl, azocinyl, diazocinyl and triazocinyl.

As used herein, the term $C_{3-7}$ cycloalkyl radical embraces saturated monocyclic carbocyclic radicals having from 3 to 7 carbon atoms. Examples of monocyclic cycloalkyl groups include cyclopropyl, cyclobutyl, cyclopentyl, cyclohexyl and cycloheptyl.

As used herein, the term monocyclic 3 to 8-membered heterocyclyl radical embraces typically a single ring non-aromatic, saturated or unsaturated $C_{3-8}$ carbocyclic ring system in which one or more of the carbon atoms are replaced by a heteroatom selected from N, O and S. Examples of 3 to 8-membered heterocyclyl radicals include aziridinyl, oxiranyl, piperidyl, pyrrolidyl, pyrrolinyl, piperazinyl, morpholinyl, thiomorpholinyl, pyrrolyl, pyrazolinyl and pirazolidinyl.

As used herein, some of the atoms, radicals, moieties, chains and cycles present in the general structures of the invention are "optionally substituted". This means that these atoms, radicals, moieties, chains and cycles can be either unsubstituted or substituted in any position by one or more, for example 1, 2, 3 or 4, substituents, whereby the hydrogen atoms bound to the unsubstituted atoms, radicals, moieties, chains and cycles are replaced by chemically acceptable atoms, radicals, moieties, chains and cycles. When two or more substituents are present, each substituent may be the same or different. The substituents are typically themselves unsubstituted.

As used herein, the term halogen atom embraces chlorine, fluorine, bromine and iodine atoms. Examples of halogen atoms include a fluorine, chlorine or bromine atom. The term halo when used as a prefix has the same meaning.

Also included within the scope of the invention are the isomers, polymorphs, pharmaceutically acceptable salts, N-oxides, isotopes, solvates and prodrugs of the compounds of Formula (I). Any reference to a compound of Formula (I) throughout the present specification includes a reference to any isomer, polymorph, pharmaceutically acceptable salt, N-oxide, isotope, solvate or prodrug of such compound of Formula (I).

Compounds containing one or more chiral centre may be used in enantiomerically or diastereoisomerically pure form, in the form of racemic mixtures and in the form of mixtures enriched in one or more stereoisomer. The compounds of Formula (I) as described and claimed encompass the racemic forms of the compounds as well as the individual enantiomers, diastereomers, and stereoisomer-enriched mixtures.

Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereoisomeric mixture may be separated by chromatography and/or fractional crystallization and one or both of the diastereoisomers converted to the corresponding pure enantiomer(s) by means well known to one skilled in the art. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomer conglomerates may be separated by conventional techniques known to those skilled in the art. See, e.g. "Stereochemistry of Organic Compounds" by Ernest L. Eliel (Wiley, New York, 1994).

Atropisomers are stereoisomers resulting from hindered rotation about single bonds where the steric strain barrier to rotation is high enough to allow for the isolation of the conformers. Oki (Oki, M; Topics in Stereochemistry 1983, 1) defined atropisomers as conformers that interconvert with a half-life of more than 1000 seconds at a given temperature. The scope of the invention as described and claimed encompasses the racemic forms of the compounds as well as the individual atropisomers (an atropisomer "substantially free" of tis corresponding enantionmer) and stereoisomer-enriched mixtures, i.e. mixtures of atropisomers.

Separation of atropisomers is possibly by chiral resolution methods such as selective crystallization. In an atropoenantioselective or atroposelective synthesis one atropisomer is formed at the expense of the other. Atroposelective synthesis may be carried out by use of chiral auxiliaries like a Corey-Bakshi-Shibata (CBS) catalyst (asymmetric catalyst derived from proline) in the total synthesis of knipholone or by approaches based on thermodynamic equilibration when an isomerization reaction favors one atropisomer over the other.

As used herein, the term pharmaceutically acceptable salt refers to a salt prepared from a base or acid which is acceptable for administration to a patient, such as a mammal. Such salts can be derived from pharmaceutically-acceptable inorganic or organic bases and from pharmaceutically-acceptable inorganic or organic acids.

As used herein, an N-oxide is formed from the tertiary basic amines or imines present in the molecule, using a convenient oxidising agent.

The invention also includes isotopically-labeled derivatives of the compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled derivatives of the compounds of the invention can generally be prepared by conventional techniques known to those skilled in the art or by processes analogous to those described herein, using an appropriate isotopically-labeled reagent in place of the non-labeled reagent otherwise employed.

Preferred isotopically-labeled derivatives include deuterated derivatives of the compounds of the invention. As used herein, the term deuterated derivative embraces compounds of the invention where in a particular position at least one hydrogen atom is replaced by deuterium. Deuterium (D or $^2$H) is a stable isotope of hydrogen which is present at a natural abundance of 0.015 molar %.

The compounds of the invention may exist in both unsolvated and solvated forms. The term solvate is used herein to describe a molecular complex comprising a compound of the invention and an amount of one or more pharmaceutically acceptable solvent molecules. The term hydrate is employed when said solvent is water. Examples of solvate forms include, but are not limited to, compounds of the invention in association with water, acetone, dichloromethane, 2-propanol, ethanol, methanol, dimethylsulfoxide (DMSO), ethyl acetate, acetic acid, ethanolamine, or mixtures thereof. It is specifically contemplated that in the present invention one solvent molecule can be associated with one molecule of the compounds of the present invention, such as a hydrate.

Prodrugs of the compounds described herein are also within the scope of the invention. Thus certain derivatives of the compounds of the present invention, which derivatives may have little or no pharmacological activity themselves, when administered into or onto the body may be converted into compounds of the present invention having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association).

Prodrugs in accordance with the invention can, for example, be produced by replacing appropriate functionalities present in the compounds of the present invention with certain moieties known to those skilled in the art as 'promoieties' as described, for example, in Design of Prodrugs by H. Bundgaard (Elsevier, 1985).

X represents —N= or —CR$^c$=. R$^c$ represents a hydrogen atom, halogen atom, a lineal or branched C$_{1-4}$ alkyl group or a lineal or branched C$_{1-4}$ alkoxy group.

Typically, in the compound of Formula (I), X represents —CR$^c$=, wherein R$^c$ represents a hydrogen atom or halogen atom, preferably R$^c$ represents a hydrogen atom or a fluorine atom. Each R$^c$ may independently represent a hydrogen atom or halogen atom. Each R$^c$ may independently represent a hydrogen atom or a fluorine atom Typically R$_1$ represents —R$^d$, or —O—R$^d$, wherein R$^d$ represents a lineal or branched C$_{1-3}$ fluoroalkyl group.

Typically R$_2$ and R$_3$ independently are selected from the group consisting of a hydrogen atom, a lineal or branched C$_{1-4}$ alkyl group, a lineal or branched C$_{1-4}$ hydroxyalkyl group, —(CH$_2$)$_p$—R$^e$ group and —SO$_2$—NR$^a$R$^b$ group, R$^a$ and R$^b$ independently represents a hydrogen atom or a C$_{1-2}$ alkyl group, and wherein R$^e$ represents a monocyclic 4 to 6-membered N-containing heterocyclyl group and substituted with a methyl group.

In a preferred embodiment, R$_2$ and R$_3$ independently are selected from the group consisting of a hydrogen atom, a methyl group and a C$_{1-2}$ hydroxyalkyl group, preferably, a hydrogen atom and a methyl group, more preferably, R$_2$ and R$_3$ represents a hydrogen atom.

Typically R$_4$ is selected from the group consisting of a lineal or branched C$_{1-4}$ alkyl group optionally substituted with one or more substituent selected from a halogen atom, —(CH$_2$)—CO—NH$_2$ group and a lineal C$_{1-3}$ hydroxyalkyl group, more preferably a C$_{1-2}$ alkyl group optionally substituted with one or more substituent selected from a fluorine atom, even more preferably, R$_4$ represents a methyl group or a —CH$_2$CF$_3$ group, being most preferred a methyl group.

Typically, R$_5$ represents a hydrogen atom or a fluorine atom, preferably a hydrogen atom.

In a still preferred embodiment, compounds of the present invention having Formula (I)
  wherein
  each X independently represents a —N= or —CR$^c$=,
  R$_1$ represents —R$^d$, or —O—R$^d$, R$_2$ and R$_3$ independently are selected from the group consisting of a hydrogen atom, a methyl group, a lineal C$_{2-3}$ hydroxyalkyl group, a cyclohexyl group substituted with an amino group, a O-containing monocyclic 6-membered heterocyclyl group, a C$_{1-2}$ alkylsulfonyl group, —(CH$_2$)$_p$—CO—(CH$_2$)$_q$—NH$_2$ group, —(CH$_2$)$_r$—NR$^a$R$^b$ group, —(CH$_2$)$_p$—R$^e$ group, —SO$_2$—NR$^a$R$^b$ group, and —CO—CF$_3$ group, R$_4$ is selected from the group consisting of a lineal or branched C$_{1-4}$ alkyl group optionally substituted with one or more substituent selected from a fluorine atom, —(CH$_2$)—CO—NH$_2$ group, a lineal C$_{2-3}$ hydroxyalkyl group, an aminopropyl group, a methoxyethyl group, —(CH$_2$)$_p$—R$^e$ group and —(CH$_2$)$_r$—NR$^a$R$^b$ group, R$_5$ is selected from the group consisting of a hydrogen atom and halogen atom, R$^a$ and R$^b$ independently represents a hydrogen atom or C$_{1-2}$ alkyl group, or R$^a$ and R$^b$ together with N form a monocyclic 4 to 6-membered heterocyclyl and optionally containing at least one further heteroatom selected from O, each R$^c$ independently represents a hydrogen atom, a fluorine atom or a methoxy group, R$^d$ represents a lineal or branched C$_{1-3}$ fluoroalkyl group, R$^e$ represents a monocyclic 6-membered heteroaryl group containing N as heteroatom or a monocyclic 6-membered heterocyclyl group containing N as heteroatom and optionally substituted with a methyl group, p and q independently have a value of 0, 1 or 2, r has a value of 2.

In even more preferred embodiment, compounds of the present invention having Formula (I)

wherein:

X represents —CR$^C$=, wherein each R$^c$ independently represents a hydrogen atom or a fluorine atom, R$_1$ represents —R$^d$, or —O—R$^d$, wherein R$^d$ represents a lineal or branched C$_{2-3}$ fluoroalkyl group, both R$_2$ and R$_3$ represents a hydrogen atom, R$_4$ represents a methyl group, and R$_5$ represents a hydrogen atom.

In some cases, all X are —CR$^C$= and all R$^C$ are hydrogen.

Particular individual compounds of the invention include:

2-(3-amino-6-(5-fluoro-2-(2,2,3,3,3-pentafluoropropoxy)phenyl)-1H-indazol-1-yl)acetamide 2-(3-amino-6-(5-fluoro-2-(2,2,2-trifluoroethoxy)phenyl)-1H-indazol-1-yl)acetamide 6-(5-methoxy-2-(2,2,3,3,3-pentafluoropropoxy)phenyl)-1-methyl-1H-indazol-3-amine 6-(5-fluoro-2-(2,2,3,3,3-pentafluoropropoxy)phenyl)-1-methyl-1H-indazol-3-amine 2-(3-amino-6-(2-(2,2,3,3,3-pentafluoropropoxy)phenyl)-1H-indazol-1-yl)acetamide 2-(3-amino-6-(2-(2,2,2-trifluoroethoxy)phenyl)-1H-indazol-1-yl)acetamide 1-methyl-6-(2-(2,2,3,3,3-pentafluoropropoxy)phenyl)-1H-indazol-3-amine 1-methyl-6-(2-(2,2,2-trifluoroethoxy)phenyl)-1H-indazol-3-amine 6-(5-methoxy-2-(2,2,2-trifluoroethoxy)phenyl)-1-methyl-1H-indazol-3-amine 6-(5-fluoro-2-(2,2,2-trifluoroethoxy)phenyl)-1-methyl-1H-indazol-3-amine 2-(1-methyl-6-(2-(2,2,2-trifluoroethoxy)phenyl)-1H-indazol-3-ylamino)acetamide 2-(1-methyl-6-(2-(2,2,3,3,3-pentafluoropropoxy)phenyl)-1H-indazol-3-ylamino)ethanol 2-(1-trifluoromethyl-6-(2-(2,2,2-trifluoroethoxy)phenyl)-1H-indazol-3-amine 6-(2-(2,2,3,3,3-pentafluoropropoxy)phenyl)-1H-indazol-3-amine 2-(3-amino-6-(2-(2,2,2-trifluoroethoxy)phenyl)-1H-indazol-1-yl)ethanol 6-(5-fluoro-2-(2,2,3,3,3-pentafluoropropoxy)phenyl)-1H-indazol-3-amine 3-(3-amino-6-(2-(2,2,3,3,3-pentafluoropropoxy)phenyl)-1H-indazol-1-yl)propan-1-ol 3-(3-amino-6-(5-fluoro-2-(2,2,2-trifluoroethoxy)phenyl)-1H-indazol-1-yl)propan-1-ol 3-(3-amino-6-(5-fluoro-2-(2,2,3,3,3-pentafluoropropoxy)phenyl)-1H-indazol-1-yl)propan-1-ol 2-(6-(5-fluoro-2-(2,2,3,3,3-pentafluoropropoxy)phenyl)-3-(3-hydroxypropylamino)-1H-indazol-1-yl)acetamide 6-(3-fluoro-2-(2,2,2-trifluoroethoxy)phenyl)-1-methyl-1H-indazol-3-amine 6-(3-fluoro-2-(2,2,3,3,3-pentafluoropropoxy)phenyl)-1-methyl-1H-indazol-3-amine 6-(4-fluoro-2-(2,2,3,3,3-pentafluoropropoxy)phenyl)-1-methyl-1H-indazol-3-amine 6-(2-fluoro-6-(2,2,3,3,3-pentafluoropropoxy)phenyl)-1-methyl-1H-indazol-3-amine 6-(2-fluoro-6-(2,2,2-trifluoroethoxy)phenyl)-1-methyl-1H-indazol-3-amine 2-(3-amino-6-(3-fluoro-2-(2,2,3,3,3-pentafluoropropoxy)phenyl)-1H-indazol-1-yl)acetamide 3-(1-methyl-6-(2-(2,2,3,3,3-pentafluoropropoxy)phenyl)-1H-indazol-3-ylamino)propan-1-ol 2-(3-amino-6-(3-fluoro-2-(2,2,2-trifluoroethoxy)phenyl)-1H-indazol-1-yl)acetamide 2-(3-amino-6-(4-fluoro-2-(2,2,3,3,3-pentafluoropropoxy)phenyl)-1H-indazol-1-yl)acetamide 2-(3-amino-6-(4-fluoro-2-(2,2,2-trifluoroethoxy)phenyl)-1H-indazol-1-yl)acetamide 2-(3-amino-6-(2-fluoro-6-(2,2,2-trifluoroethoxy)phenyl)-1H-indazol-1-yl)acetamide 2,2'-(1-methyl-6-(2-(2,2,2-trifluoroethoxy)phenyl)-1H-indazol-3-ylazanediyl)diethanol 3-(3-amino-6-(3-fluoro-2-(2,2,2-trifluoroethoxy)phenyl)-1H-indazol-1-yl)propan-1-ol 3-(3-amino-6-(3-fluoro-2-(2,2,3,3,3-pentafluoropropoxy)phenyl)-1H-indazol-1-yl)propan-1-ol 3-((1-methyl-6-(2-(2,2,2-trifluoroethoxy)phenyl)-1H-indazol-3-yl)amino)-3-oxopropan-1-amine 3-((6-(5-fluoro-2-(2,2,2-trifluoroethoxy)phenyl)-1-methyl-1H-indazol-3-yl)amino)-3-oxopropan-1-amine N-1-(6-(5-fluoro-2-(2,2,3,3,3-pentafluoropropoxy)phenyl)-1-methyl-1H-indazol-3-yl)-N2-methylethane-1,2-diamine 3-(3-amino-6-(2-fluoro-6-(2,2,2-trifluoroethoxy)phenyl)-1H-indazol-1-yl)propan-1-ol 3-(3-amino-6-(2-(2,2-difluoroethoxy)-6-fluorophenyl)-1H-indazol-1-yl)propan-1-ol 6-(3-methoxy-2-(2,2,2-trifluoroethoxy)phenyl)-1-methyl-1H-indazol-3-amine 6-(2-(2,2-difluoroethoxy)-3-methoxyphenyl)-1-methyl-1H-indazol-3-amine 6-(2-(2,2-difluoroethoxy)-3-fluorophenyl)-1-methyl-1H-indazol-3-amine 3-(3-amino-6-(2-(2,2-difluoroethoxy)phenyl)-1H-indazol-1-yl)propan-1-ol 6-(3-fluoro-2-(2,2,2-trifluoroethoxy)phenyl)-1-methyl-N-((1-methylpiperidin-4-yl)methyl)-1H-indazol-3-amine N-1-(6-(3-fluoro-2-(2,2,2-trifluoroethoxy)phenyl)-1-methyl-1H-indazol-3-yl)-N2-methylethane-1,2-diamine 6-(3-fluoro-2-(2,2,2-trifluoroethoxy)phenyl)-1-methyl-N,N-bis(2-(piperidin-4-yl)ethyl)-1H-indazol-3-amine 1-methyl-6-(2-(2,2,2-trifluoroethoxy)pyridin-3-yl)-1H-indazol-3-amine 3-(3-amino-6-(3-fluoro-2-(2,2,2-trifluoroethoxy)phenyl)-1H-indazol-1-yl)propane-1,2-diol 6-(2-(2,2-difluoroethoxy)pyridin-3-yl)-1-methyl-1H-indazol-3-amine N-(6-(3-fluoro-2-(2,2,2-trifluoroethoxy)phenyl)-1-methyl-1H-indazol-3-yl)sulfonamide 1-(3-aminopropyl)-6-(3-fluoro-2-(2,2,2-trifluoroethoxy)phenyl)-1H-indazol-3-amine 3-(3-amino-6-(2-fluoro-6-(2,2,2-trifluoroethoxy)phenyl)-1H-indazol-1-yl)propane-1,2-diol N-(6-(3-fluoro-2-(2,2,2-trifluoroethoxy)phenyl)-1-methyl-1H-indazol-3-yl)methanesulfonamide N-(6-(3-fluoro-2-(2,2,2-trifluoroethoxy)phenyl)-1-methyl-1H-indazol-3-yl)ethanesulfonamide 6-(2-(2,2-difluoroethoxy)-3-fluorophenyl)-N,N,1-trimethyl-1H-indazol-3-amine N-(6-(2-(2,2-difluoroethoxy)-3-fluorophenyl)-1-methyl-1H-indazol-3-yl)-2,2,2-trifluoroacetamide 6-(2-(2,2-difluoroethoxy)-3-fluorophenyl)-N,1-dimethyl-1H-indazol-3-amine 6-(2-(difluoromethoxy)-3-fluorophenyl)-1-methyl-1H-indazol-3-amine N-methyl-N'-(6-(3-fluoro-2-(2,2,2-trifluoroethoxy)phenyl)-1-methyl-1H-indazol-3-yl)sulfamide 1-methyl-6-(2-(trifluoromethoxy)phenyl)-1H-indazol-3-amine 2-(3-amino-6-(2-(trifluoromethoxy)phenyl)-1H-indazol-1-yl)acetamide 2-(1-(2-amino-2-oxoethyl)-6-(2-(trifluoromethoxy)phenyl)-1H-indazol-3-ylamino)acetamide 2-(3-(2-hydroxyethylamino)-6-(2-(trifluoromethoxy)phenyl)-1H-indazol-1-yl)acetamide 2-(3-amino-6-(2-(trifluoromethyl)phenyl)-1H-indazol-1-yl)acetamide 2-(3-((2-aminoethyl)amino)-6-(2-(trifluoromethoxy)phenyl)-1H-indazol-1-yl)acetamide 2-(3-amino-6-(2-(trifluoromethoxy)phenyl)-1H-indazol-1-yl)ethanol 3-(3-amino-6-(2-(trifluoromethyl)phenyl)-1H-indazol-1-yl)propan-1-ol 3-(3-amino-6-(2-(trifluoromethoxy)phenyl)-1H-indazol-1-yl)propan-1-ol 1-(3-aminopropyl)-6-(2-(trifluoromethoxy)phenyl)-1H-indazol-3-amine 1-methyl-6-(2-(trifluoromethyl)phenyl)-1H-pyrazolo[3,4-b]pyridin-3-amine 3-(3-amino-6-(2-(trifluoromethyl)phenyl)-1H-pyrazolo[3,4-b]pyridin-1-yl)propan-1-ol 6-(3-fluoro-2-(trifluoromethyl)phenyl)-1-methyl-1H-indazol-3-amine 1-methyl-6-(2-(trifluoromethyl)phenyl)-1H-pyrazolo[3,4-b]pyrazin-3-amine 1-methyl-6-(2-(trifluoromethyl)pyridin-3-yl)-1H-indazol-3-amine N,N-dimethyl-N'-(6-(3-fluoro-2-(2,2,2-trifluoroethoxy)phenyl)-1-methyl-1H-indazol-3-yl)sulfamide N-(6-(3-fluoro-2-(2,2,2-trifluoroethoxy)phenyl)-1-methyl-1H-indazol-3-yl)piperidine-1-sulfonamide 6-(2-fluoro-6-(2,2,2-trifluoroethoxy)phenyl)-1-methyl-1H-pyrazolo[3,4-b]pyrazin-3-amine 1-(3-aminopropyl)-6-(3-fluoro-2-(2,2,3,3,3-pentafluoropropoxy)phenyl)-1H-indazol-3-amine 1-methyl-6-(3-(2,2,2-trifluoroethoxy)pyridin-4-yl)-1H-indazol-3-amine 1-isopropyl-6-(2-(trifluoromethoxy)phenyl)-1H-indazol-3-amine 1-isobutyl-6-(2-(trifluoromethoxy)phenyl)-1H-indazol-3-amine 1-(2-methoxyethyl)-6-(2-(trifluoromethoxy)phenyl)-1H-indazol-3-amine 1-(pyridin-3-ylmethyl)-6-(2-(trifluoromethoxy)phenyl)-1H-indazol-3-amine 1-ethyl-6-(2-(trifluoromethoxy)phenyl)-1H-indazol-3-amine N-(6-(3-fluoro-2-(2,2,2-trifluoroethoxy)phenyl)-1-methyl-1H-indazol-3-yl)morpholine-4-sulfonamide N-(6-(3-fluoro-2-(2,2,2-trifluoroethoxy)phenyl)-1-methyl-1H-indazol-3-yl)azetidine-1-sulfonamide 6-(3-fluoro-2-(2,2,3,3,3-pentafluoropropoxy)phenyl)-1-methyl-N-(tetrahydro-2H-pyran-4-yl)-1H-indazol-3-amine $N^1$-(6-(3-fluoro-2-(2,2,3,3,3-pentafluoropropoxy)phenyl)-1-methyl-1H-indazol-3-yl)cyclohexane-1,4-diamine N-(6-(3-fluoro-2-(2,2,2-trifluoroethoxy)phenyl)-1-methyl-1H-indazol-3-yl)-N-(methylsulfonyl)methanesulfonamide 1-(3-(dimethylamino)propyl)-6-(3-fluoro-2-(2,2,2-trifluoroethoxy)phenyl)-1H-indazol-3-amine 6-(3-fluoro-2-(2,2,2-trifluoroethoxy)phenyl)-1-methyl-1H-pyrazolo[4,3-b]pyridin-3-amine 6-(3-fluoro-2-(2,2,2-trifluoroethoxy)phenyl)-4-methoxy-1-methyl-1H-indazol-3-amine 4-fluoro-6-(3-fluoro-2-(2,2,2-trifluoroethoxy)phenyl)-1-methyl-1H-indazol-3-amine, or a pharmaceutically acceptable salt, or N-oxide, or isotopically-labeled derivate thereof.

Of outstanding interest are:

6-(5-methoxy-2-(2,2,3,3,3-pentafluoropropoxy)phenyl)-1-methyl-1H-indazol-3-amine, 1-methyl-6-(2-(2,2,3,3,3-pentafluoropropoxy)phenyl)-1H-indazol-3-amine, 1-methyl-6-(2-(2,2,2-trifluoroethoxy)phenyl)-1H-indazol-3-amine, 2-(1-methyl-6-(2-(2,2,3,3,3-pentafluoropropoxy)phenyl)-1H-indazol-3-ylamino)ethanol, 6-(2-(2,2,3,3,3-pentafluoropropoxy)phenyl)-1H-indazol-3-amine, 6-(5-fluoro-2-(2,2,3,3,3-pentafluoropropoxy)phenyl)-1H-indazol-3-amine, 3-(3-amino-6-(2-(2,2,3,3,3-pentafluoropropoxy)phenyl)-1H-indazol-1-yl)propan-1-ol, 3-(3-amino-6-(5-fluoro-2-(2,2,2-trifluoroethoxy)phenyl)-1H-indazol-1-yl)propan-1-ol, 6-(3-fluoro-2-(2,2,2-trifluoroethoxy)phenyl)-1-methyl-1H-indazol-3-amine, 6-(3-fluoro-2-(2,2,3,3,3-pentafluoropropoxy)phenyl)-1-methyl-1H-indazol-3-amine, 6-(2-fluoro-6-(2,2,3,3,3-pentafluoropropoxy)phenyl)-1-methyl-1H-indazol-3-amine,
3-(3-amino-6-(3-fluoro-2-(2,2,2-trifluoroethoxy)phenyl)-1H-indazol-1-yl)propan-1-ol,
6-(3-methoxy-2-(2,2,2-trifluoroethoxy)phenyl)-1-methyl-1H-indazol-3-amine,
6-(2-(2,2-difluoroethoxy)-3-fluorophenyl)-1-methyl-1H-indazol-3-amine,
6-(2-(difluoromethoxy)-3-fluorophenyl)-1-methyl-1H-indazol-3-amine,
3-(3-amino-6-(2-(trifluoromethyl)phenyl)-1H-indazol-1-yl)propan-1-ol,
3-(3-amino-6-(2-(trifluoromethoxy)phenyl)-1H-indazol-1-yl)propan-1-ol,
or a pharmaceutically acceptable salt, or N-oxide, or isotopically-labeled derivate thereof.

The invention is also directed to a compound of the invention as described herein for use in the treatment of the human or animal body by therapy.

The invention also provides pharmaceutical compositions comprising at least a compound of Formula (I), as hereinabove described, in association with a pharmaceutically acceptable diluent or carrier.

The invention is also directed to the compounds of the invention as described herein, for use in the treatment of a pathological condition or disease mediated by modulation of voltage-gated sodium channels in particular Nav1.7, which condition or disease is preferably selected from pain, including but not limiting to, acute pain, chronic pain, inflammatory pain, visceral pain, nociceptive pain, neuropathic pain, postherpetic pain, trigeminal neuralgia, diabetic neuropathy, chronic back pain, chronic pelvic pain, migraine and pain resulting from cancer and chemotherapy, idiopathic cough, chronic cough or cough related to respiratory diseases, respiratory diseases, itch, dermatological diseases, epilepsy, squizophrenia and bipolar disorder.

The invention also provides the use of the compounds of the invention as described herein, for the manufacture of a medicament for the treatment of a pathological condition or disease as described above. The invention is also directed to a method of treatment of said pathological condition or disease described above, comprising administering a therapeutically effective amount of the compounds of the invention or a pharmaceutical composition of the invention to a subject in need of such treatment.

In still another embodiment the present invention covers a combination product comprising (i) at least a compound of Formula (I), as herein above described, and (ii) one or more active ingredients as mentioned above, for simultaneous, separate or sequential use in the treatment of the human or animal body.

As used herein, the term therapeutically effective amount refers to an amount sufficient to effect treatment when administered to a patient in need of treatment.

As used herein, the term treatment refers to the treatment of a disease or medical condition in a human patient which includes:

(a) preventing the disease or medical condition from occurring, i.e., prophylactic treatment of a patient;

(b) ameliorating the disease or medical condition, i.e., causing regression of the disease or medical condition in a patient;

(c) suppressing the disease or medical condition, i.e., slowing the development of the disease or medical condition in a patient; or (d) alleviating the symptoms of the disease or medical condition in a patient.

As used herein, the term disease or condition associated with modulation of voltage-gated sodium channels in particular Nav1.7 activity includes all disease states and/or conditions that are acknowledged now, or that are found in the future, to be associated with modulation of voltage-gated sodium channels in particular Nav1.7 activity. Such disease states include, but are not limited to pain, including but not limiting to, acute pain, chronic pain, inflammatory pain, visceral pain, nociceptive pain, neuropathic pain, postherpetic pain, trigeminal neuralgia, diabetic neuropathy, chronic back pain, chronic pelvic pain, migraine and pain resulting from cancer and chemotherapy, cough, respiratory diseases, itch, dermatological diseases, epilepsy, squizophrenia and bipolar disorder.

General Synthetic Procedures

The compounds of the invention can be prepared using the methods and procedures described herein, or using similar methods and procedures. It will be appreciated that typical or preferred process conditions (i.e., reaction temperatures, times, mole ratios of reactants, solvents, pressures, etc.) are given. Other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal are described in T. W. Greene and G. M. Wuts, Protecting Groups in Organic Synthesis, Third Edition, Wiley, New York, 1999, and references cited therein.

Processes for preparing compounds of the invention are provided as further embodiments of the invention and are illustrated by the procedures below.

One of the most convenient route for the preparation of compounds of Formula (I) is depicted in Scheme 1.

Scheme 1

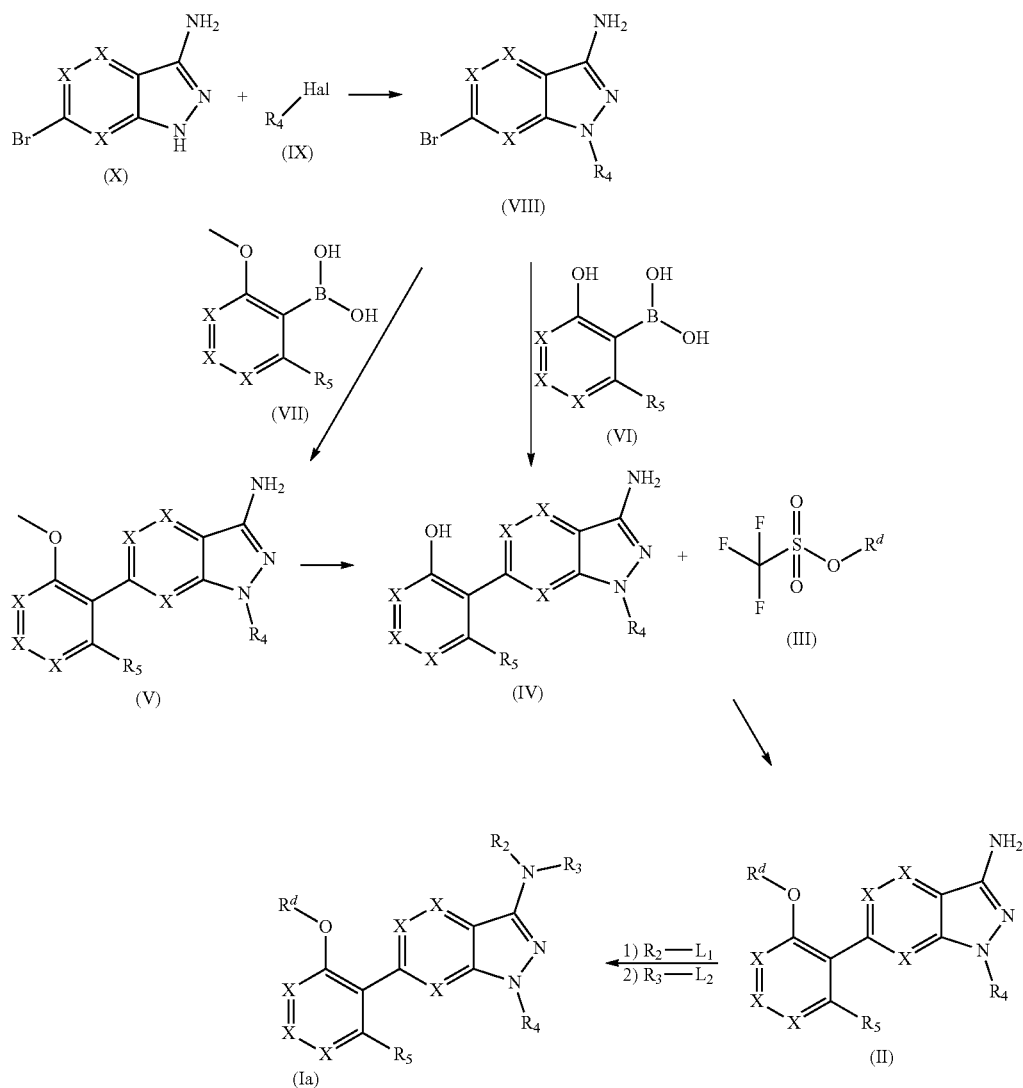

Compounds of Formula (Ia) may be prepared by reacting intermediates of Formula (II) wherein $R^4$, $R^5$ and $R^d$ are as defined above, with the halo derivatives $R_2$-$L_1$ and with $R_3$-$L_2$, wherein $R^2$ and $R^3$ are as defined above and both $L_1$ and $L_2$ may be the same or different and represent a leaving group. This reaction is best carried out in DMF at a temperature between 40 and 100° C. using the corresponding haloderivative in the presence of TBAI and NaI or KI.

Intermediate of Formula (II) can be prepared by reacting intermediate (IV) with intermediate (III), which consist in a commercially avable sulfone. This reaction is carried out in DMF at a temperature between 40 and 100° C. using a base, such as cesium carbonate.

Intermediate of Formula (IV) was obtained via Suzuki coupling, reacting commercially available intermediate (VI), [1,1'-Bis(diphenylphosphino)ferrocene]dichloropalladium(II) and sodium carbonate at at a temperature between 70 and 100° C. in a mixture of dioxane:water.

Alternatively, intermediate (IV) can be obtained through intermediate (V) using Hydrogen Bromide (48% in water) at 100° C.

Intermediate of Formula (V) was obtained via Suzuki coupling, reacting commercially available intermediate (VII), [1,1'-Bis(diphenylphosphino)ferrocene]dichloropalladium(II) and sodium carbonate at at a temperature between 70 and 100° C. in a mixture of dioxane:water.

Finally, intermediate of Formula (VIII) can be prepared by the corresponding commercially available intermediate of Formula (X) and commercially available intermediate of Formula (IX). The reaction is carried out in DMF from 0° C. to 25° C. using sodium hydride (60% dispersion in mineral oil).

Compounds of Formula (XI), wherein $R_1$ represents $R^d$ and both $R_2$ and $R_3$ represent a hydrogen atom, can be prepared in general terms as is depicted in Scheme 2.

Scheme 2

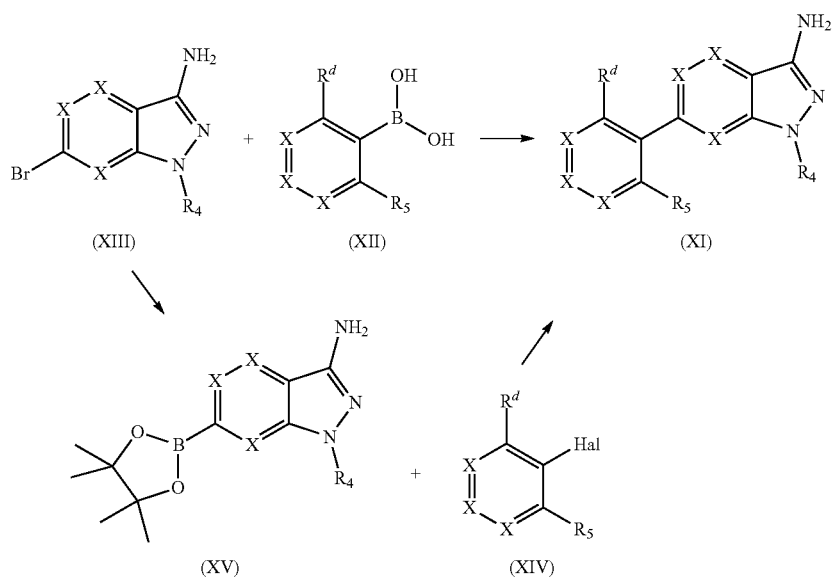

Compounds of Formula (XI) may be prepared by reacting commercially available intermediates of Formulas (XIII) and (XII). The reaction was carried out in dioxane:water (4:1) at a temperature between 40 and 100° C. using [1,1'-Bis(diphenylphosphino)ferrocene]-dichloropalladium (II) and sodium carbonate as reactants.

Alternatively, compound of Formula (XI) can be also prepared by reacting commercially available intermediate of Formula (XIV), wherein Hal represents an halogen atom, and intermediate of Formula (XV) using the reaction conditions described above. Additionally, intermediate of Formula (XV) can be obtained by reacting intermediate of Formula (XIII) and 4,4,4',4',5,5,5',5'-octamethyl-2,2'-bi(1,3, 2-dioxaborolane) in dioxane:water at a temperature between 60 and 100° C.

Another synthetic route to obtain compounds of Formula (II) is depicted in Scheme 3.

Scheme 3

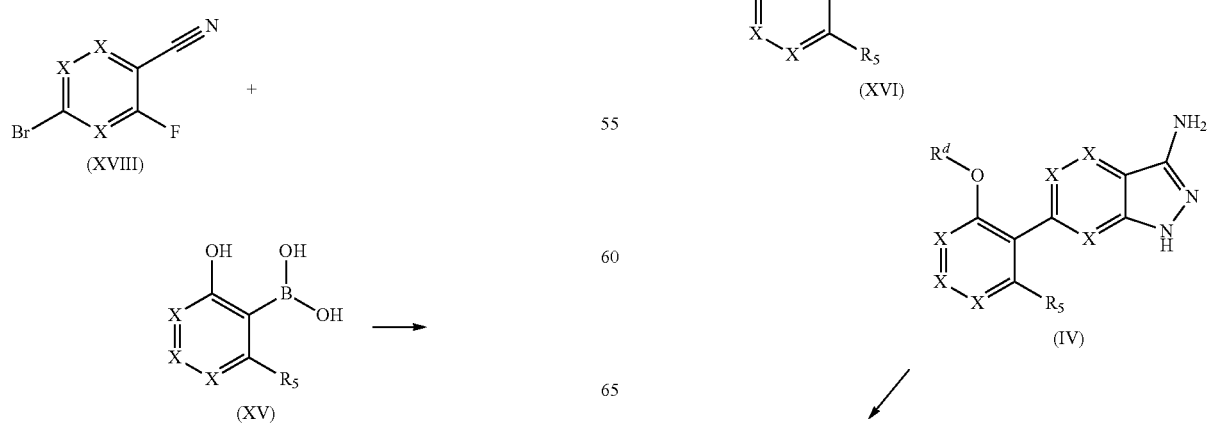

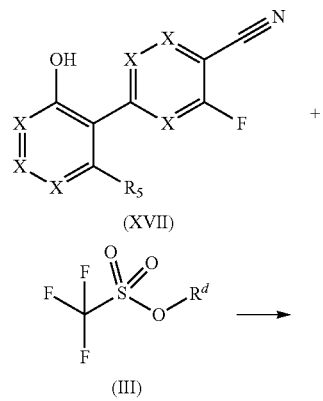

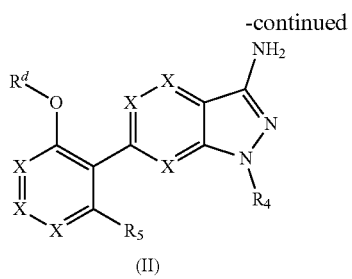

(II)

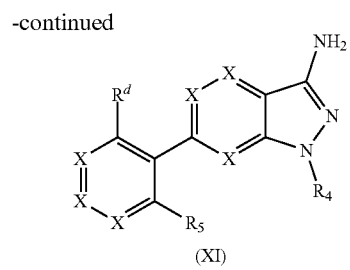

(XI)

Alternatively, compounds of Formula (II) can be prepared by reacting intermediate of Formula (IV) via alquilation described in Scheme 3. Intermediate of Formula (IV) is obtained by reacting intermediate of Formula (XVI) and hydrazine hydrate under microwave conditions in isopropanol at a temperature between 80 and 150° C. Intermediate of Formula (XVI) can be obtained via alquilation of the commercially available sulfone with intermediate of Formula (XVII). This reaction is carried out in DMF at a temperature between 40 and 100° C. using a base, such as cesium carbonate.

Finally, intermediate of Formula (XVII) can be obtained via Suzuki coupling by reacting intermediates (XVIII) and (XV) with [1,1'-Bis(diphenylphosphino)ferrocene]-dichloropalladium(II) and sodium carbonate at at a temperature between 70 and 100° C. in a mixture of dioxane:water.

An alternative route to obtain compounds of Formula (XI) is depicted in Scheme 4.

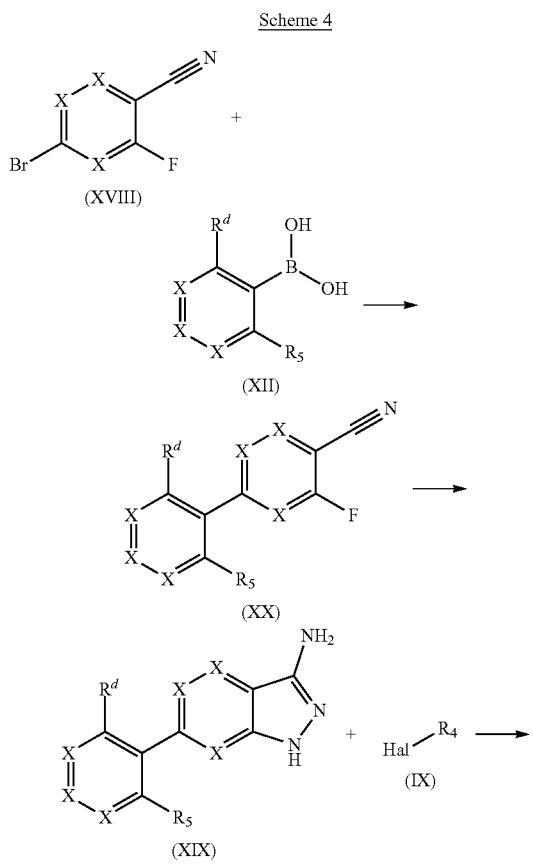

Compounds of Formula (XI) can be obtained by reacting intermediates of Formula (XIX) and (IX). The reaction is carried out in DMF from 0° C. to 25° C. using sodium hydride (60% dispersion in mineral oil). Intermediate of Formula (XIX) may be obtained via cyclization with hydrazine hydrate under microwave conditions in isopropanol at a temperature between 80 and 150° C. Intermediate of Formula (XX) was obtained via Suzuki coupling by reacting intermediates of Formula (XVIII) and (XII) with [1,1'-Bis (diphenylphosphino)-ferrocene]dichloropalladium(II) and sodium carbonate at a temperature between 70 and 100° C. in a mixture of dioxane:water.

EXAMPLES

General.

Reagents, starting materials, and solvents were purchased from commercial suppliers and used as received. Concentration refers to evaporation under vacuum using a Buchi rotatory evaporator. Reaction products were purified, when necessary, using preparative HPLC conditions C-18 reverse phase column silica from MERCK, water/acetonitrile as eluents [0.1% v/v ammonium formate buffered] using a gradient from 0% to 100%.

Spectroscopic data were recorded on a Varian Gemini 300 spectrometer. HPLC-MS were performed on a Gilson instrument equipped with a Gilson piston pump 321, a Gilson 864 vacuum degasser, a Gilson liquid handler 215, a Gilson 189 injection module, a Gilson Valvemate 7000, a 1/1000 splitter, a Gilson 307 make-up pump, a Gilson 170 diode array detector, and a Thermoquest Finnigan aQa detector.

The syntheses of the compounds of the invention and of the intermediates for use therein are illustrated by the following Examples (1-88) including Preparations (1 to 65) which do not limit the scope of the invention in any way.

Intermediate 1.
2-(3-amino-6-bromo-1H-indazol-1-yl)acetamide

To a solution of 6-bromo-1H-indazol-3-amine (544 mg, 2.5 mmol) in anhydrous dimethyl-formamide (3 mL) was added in portions at 0° C. sodium hydride (60% of an oil dispersion; 110 mg, 4.5 mmol). The mixture was stirred for 30 minutes at 0° C. A solution of 2-bromoacetamide (371 mg, 2.68 mmol) in dimethylformamide (1 mL) was added into the solution and the crude was stirred for 1 hour at room temperature. Water was added into the crude mixture and an orange precipitate was obtained. It was filtered and dried to give the title compound as an orange solid (75% of yield), which was used in the next step without further purification.

LRMS (m/z): 269 (M)$^+$; 271 (M+2)$^+$ $^1$H NMR (300 MHz, DMSO-d$_6$) δ ppm 4.71 (s, 2H); 5.6 (s, 2H); 7.02 (d, 1H); 7.61 (m, 2H)

Intermediate 2. 2-(3-amino-6-(5-fluoro-2-hydroxy-phenyl)-1H-indazol-1-yl)acetamide A solution of 2-(3-amino-6-bromo-1H-indazol-1-yl)acetamide (Intermediate 1; 100 mg, 0.37 mmol) in dioxane: water 4:1 (5 mL) was degassed under Argon. Sodium carbonate (118 mg, 1.11 mmol) and 5-fluoro-2-hydroxyphenylboronic acid (64 mg, 0.41 mmol) were added into the solution. [1,1'-Bis(diphenylphosphino)ferrocene]dichloropalladium(II) (14 mG, 0.02 mmol) was added into the crude mixture and the mixture was degassed under Argon for several minutes. The reaction was stirred at 95° C. for 16 hours. The crude mixture was filtered and evaporated under reduced pressure to give a black foam (75% of yield), which was used in the next step without further purification.

LRMS (m/z): 301 (M+1)$^+$

Intermediate 3. 6-bromo-1-methyl-1H-indazol-3-amine

A solution of 6-bromo-1H-indazol-3-amine (788 mg, 3.71 mmol) in dimethylformamide (3 mL) was cooled to 0° C. and sodium hydride (60% of an oil dispersion; 163 mg, 6.79 mmol) was added in portions. The mixture was stirred for 30 minutes at 0° C. Methyl iodide (225 µL, 4.09 mmol) was added into the mixture and stirred for 2 hours at room temperature. Water was added into the crude mixture and a red solid precipitates. The crude mixture was filtered and dried. A red solid was obtained as the title compound (80% of yield).

LRMS (m/z): 226 (M)$^+$, 228 (M+2)$^+$ $^1$H NMR (300 MHz, DMSO-d$_6$) δ ppm 3.75 (s, 3H); 5.7 (s, 2H); 7.01 (d, 1H); 7.59 (d, 1H); 7.6 (s, 1H).

Intermediate 4. 2-(3-amino-1-methyl-1H-indazol-6-yl)-4-methoxyphenol

Obtained as a foam (85% of yield) from 6-bromo-1-methyl-1H-indazol-3-amine (Intermediate 3; 100 mg, 0.44 mmol), 2-hydroxy-5-methoxyphenylboronic acid (82 mg, 0.48 mmol), sodium carbonate (140 mg, 1.32 mmol) and [1,1'-Bis(diphenylphosphino)ferrocene]-dichloropalladium(II) (18 mg, 0.02 mmol) following the experimental procedure as described for Intermediate 2. The crude obtained was used in the next step without further purification.

LRMS (m/z): 270 (M+1)$^+$

Intermediate 5. 2-(3-amino-1-methyl-1H-indazol-6-yl)-4-fluorophenol

Obtained as a foam (95% of yield) from 6-bromo-1-methyl-1H-indazol-3-amine (Intermediate 3; 100 mg, 0.44 mmol), 5-fluoro-2-hydroxyphenylboronic acid (76 mg, 0.48 mmol), sodium carbonate (140 mg, 1.32 mmol) and [1,1'-Bis(diphenylphosphino)ferrocene]-dichloropalladium(II) (18 mg, 0.02 mmol) following the experimental procedure as described for Intermediate 2. The crude obtained was used in the next step without further purification.

LRMS (m/z): 258 (M+1)$^+$

Intermediate 6. 2-(3-amino-6-(2-hydroxyphenyl)-1H-indazol-1-yl)acetamide

Obtained as black solid (88% of yield) from 2-(3-amino-6-bromo-1H-indazol-1-yl)acetamide (Intermediate 1; 200 mg, 0.74 mmol), 2-(4,4,5,5-tetramethyl-1,3,2-dioxaborolan-2-yl)phenol (138 µL, 0.65 mmol), sodium carbonate (159 mg, 1.5 mmol) and [1,1'-Bis(diphenylphosphino)ferrocene]dichloropalladium(II) (25 mg, 0.03 mmol) following the experimental procedure as described for Intermediate 2. The crude obtained was used in the next step without further purification.

LRMS (m/z): 283 (M+1)$^+$

Intermediate 7. 2-(3-amino-1-methyl-1H-indazol-6-yl)phenol

Obtained as foam (75% of yield) from 6-bromo-1-methyl-1H-indazol-3-amine (Intermediate 3; 150 mg, 0.66 mmol), 2-hydroxyphenylboronic acid (100 mg, 0.72 mmol), sodium carbonate (210 mg, 1.99 mmol) and [1,1'-Bis(diphenylphosphino)ferrocene]dichloropalladium(II) (27 mg, 0.03 mmol) following the experimental procedure as described for Intermediate 2. The crude obtained was used in the next step without further purification.

LRMS (m/z): 240 (M+1)$^+$

Intermediate 8. 6-bromo-1-(2-(tert-butyldimethylsilyloxy)ethyl)-1H-indazol-3-amine To a solution of 6-bromo-1H-indazol-3-amine (200 mg, 0.94 mmol) in dimethylformamide (2 mL) was added cesium carbonate (614 mg, 1.88 mmol) and (2-bromoethoxy)(tert-butyl)dimethylsilane (215 µL, 1.03 mmol). The reaction mixture was stirred for 3 hours at 65° C. Water was added into the crude mixture. A solid precipitates and it was dried to obtain the title compound as an orange solid (83% of yield), which was used in the next step without further purification.

LRMS (m/z): 371 (M+1)$^+$

Intermediate 9. 2-(3-amino-1-(2-(tert-butyldimethylsilyloxy)ethyl)-1H-indazol-6-yl)phenol Obtained as a brown solid (95% of yield) from 6-bromo-1-(2-(tert-butyldimethylsilyloxy)ethyl)-1H-indazol-3-amine (Intermediate 8; 180 mg, 0.48 mmol), 2-(4,4,5,5-tetramethyl-1,3,2-dioxaborolan-2-yl)phenol (117 mg, 0.53 mmol), sodium carbonate (154 mg, 1.45 mmol) and [1,1'-Bis(diphenylphosphino)ferrocene]dichloropalladium(II) (20 mg, 0.02 mmol) following the experimental procedure as described for Intermediate 2. The crude obtained was used in the next step without further purification.

LRMS (m/z): 384 (M+1)$^+$

Intermediate 10. 2-(3-amino-1-(2-(tert-butyldimethylsilyloxy)ethyl)-1H-indazol-6-yl)-4-fluorophenol Obtained as a brown solid (98% of yield) from 6-bromo-1-(2-(tert-butyldimethylsilyloxy)ethyl)-1H-indazol-3-amine (Intermediate 8; 180 mg 0.48 mmol), 5-fluoro-2-hydroxyphenylboronic acid (83 mg, 0.53 mmol), sodium carbonate (154 mg, 1.45 mmol) and [1,1'-Bis(diphenylphosphino)ferrocene]dichloropalladium(II) (20 mg, 0.02 mmol) following the experimental procedure as described for Intermediate 2. The crude obtained was used in the next step without further purification.

LRMS (m/z): 402 (M+1)$^+$

Intermediate 11. 6-bromo-1-(3-(tert-butyldimethylsilyloxy)propyl)-1H-indazol-3-amine To a solution of 6-bromo-1H-indazol-3-amine (400 mg, 1.88 mmol) in dimethylformamide (5 mL) was added cesium carbonate (1.2 g, 3.77 mmol) and (3-bromopropoxy)(tert-butyl)dimethylsilane (525 mg, 2.07 mmol). The reaction mixture was stirred for 2 hours at 65° C. The crude was poured into water and the solid obtained was filtered and dried. The title compound was obtained as a brown solid (95% of yield), which was used in the next step without further purification.

LRMS (m/z): 385 (M+1)$^+$

Intermediate 12. 2-(3-amino-1-(3-(tert-butyldimethylsilyloxy)propyl)-1H-indazol-6-yl)phenol Obtained as a foam (54% of yield) from 6-bromo-1-(3-(tert-butyldimethylsilyloxy)propyl)-1H-indazol-3-amine (150 mg, 0.39 mmol), 2-(4,4,5,5-tetramethyl-1,3,2-dioxaborolan-2-yl)phenol (117 mg, 0.53 mmol), sodium carbonate (154 mg, 1.45 mmol) and [1,1'-Bis(diphenylphosphino)ferrocene]dichloropalladium(II) (20 mg, 0.02 mmol) following the experimental procedure as described for Intermediate 2. The crude obtained was used in the next step without further purification.

LRMS (m/z): 398 (M+1)$^+$

Intermediate 13. 1-(3-(tert-butyldimethylsilyloxy)propyl)-6-(2-(2,2,3,3,3-pentafluoropropoxy)phenyl)-1H-indazol-3-amine Obtained as a brown solid (95% of yield) from 2-(3-amino-1-(3-(tert-butyldimethylsilyloxy)propyl)-1H-indazol-6-yl)phenol (Intermediate 12; 77 mg, 0.19 mmol), cesium carbonate (189 mg, 0.58 mmol) and 2,2,3,3,3-pentafluoropropyl trifluoromethanesulfonate (109 µL, 0.38 mmol) following the experimental procedure as described for Example 1. The crude obtained was used in the final step without further purification.

LRMS (m/z): 530 (M+1)$^+$

Intermediate 14. 2-(3-amino-1-(3-(tert-butyldimethylsilyloxy)propyl)-1H-indazol-6-yl)-4-fluorophenol Obtained as a foam (95% of yield) from 6-bromo-1-(3-(tert-butyldimethylsilyloxy)propyl)-1H-indazol-3-amine (Intermediate 11; 150 mg, 0.39 mmol), 5-fluoro-2-hydroxyphenylboronic acid (67 mg, 0.42 mmol), sodium carbonate (124 mg, 1.17 mmol) and [1,1'-Bis(diphenylphosphino)ferrocene]dichloropalladium(II) (16 mg, 0.019 mmol) following the experimental procedure as described for Intermediate 2. The crude obtained was used in the next step without further purification.

LRMS (m/z): 416 (M+1)$^+$

Intermediate 15. 1-(3-(tert-butyldimethylsilyloxy)propyl)-6-(5-fluoro-2-(2,2,2-trifluoroethoxy)phenyl)-1H-indazol-3-amine Obtained as a foam (65% of yield) from 2-(3-amino-1-(3-(tert-butyldimethylsilyloxy)propyl)-1H-indazol-6-yl)-4-fluorophenol (Intermediate 14; 77 mg, 0.19 mmol), cesium carbonate (189 mg, 0.58 mmol) and 2,2,2-trifluoroethyl trifluoromethanesulfonate (20 µL, 0.13 mmol) following the experimental procedure as described for Example 1. The crude obtained was used in the final step without further purification.

LRMS (m/z): 498 (M+1)$^+$

Intermediate 16. 1-(3-(tert-butyldimethylsilyloxy)propyl)-6-(5-fluoro-2-(2,2,3,3,3-pentafluoropropoxy)phenyl)-1H-indazol-3-amine Obtained as a foam (97% of yield) from 2-(3-amino-1-(3-(tert-butyldimethylsilyloxy)propyl)-1H-indazol-6-yl)-4-fluorophenol (Intermediate 14; 81 mg, 0.19 mmol), cesium carbonate (190 mg, 0.58 mmol) and 2,2,3,3,3-pentafluoropropyl trifluoromethanesulfonate (23 µL, 0.13 mmol) (20 µL, 0.13 mmol) following the experimental procedure as described for Example 1. The crude obtained was used in the final step without further purification.

LRMS (m/z): 548 (M+1)$^+$

Intermediate 17. 2-(3-(3-(tert-butyldimethylsilyloxy)propylamino)-6-(5-fluoro-2-(2,2,3,3,3-pentafluoropropoxy)phenyl)-1H-indazol-1-yl)acetamide To a solution of 2-(3-amino-6-(5-fluoro-2-(2,2,2-trifluoroethoxy)phenyl)-1H-indazol-1-yl)acetamide (Example 1; 44 mg, 0.10 mmol) in dimethylformamide (2 mL) was added (3-bromopropoxy)(tert-butyl)dimethylsilane (60 µL; 0.25 mmol) and cesium carbonate (100 mg, 0.3 mmol). The reaction mixture was stirred at 65° C. overnight. The crude mixture was dried under reduced pressure and purified by preparative-HPLC using the described conditions in the general procedures to give the title compound as foam (47% of yield).

LRMS (m/z): 603 (M+1)$^+$

Intermediate 18. 2-(3-amino-1-methyl-1H-indazol-6-yl)-6-fluorophenol

Obtained as a red solid (98% of yield) from 6-bromo-1-methyl-1H-indazol-3-amine (Intermediate 3; 500 mg, 2.2 mmol), 3-fluoro-2-hydroxyphenylboronic acid (413 mg, 2.64 mmol), sodium carbonate (703 mg, 6.63 mmol) and [1,1'-Bis(diphenylphosphino)ferrocene]dichloropalladium(II) (90 mg, 0.1 mmol) following the experimental procedure as described for Intermediate 2. The crude obtained was used in the next step without further purification.

LRMS (m/z): 258 (M+1)$^+$

Intermediate 19. 2-(3-amino-1-methyl-1H-indazol-6-yl)-5-fluorophenol

Obtained as a foam (21% of yield) from 6-bromo-1-methyl-1H-indazol-3-amine (Intermediate 3; 100 mg, 0.44 mmol), 4-fluoro-2-hydroxyphenylboronic acid (83 mg, 0.53 mmol), sodium carbonate (140 mg, 1.32 mmol) and [1,1'-Bis(diphenylphosphino)ferrocene]dichloropalladium(II) (18 mg, 0.02 mmol) following the experimental procedure as described for Intermediate 2. The crude obtained was used in the next step without further purification.

LRMS (m/z): 258 (M+1)$^+$

Intermediate 20. 2-(3-amino-1-methyl-1H-indazol-6-yl)-3-fluorophenol

Obtained as a black solid (95% of yield) from 6-bromo-1-methyl-1H-indazol-3-amine (Intermediate 3; 100 mg, 0.44 mmol), 2-fluoro-6-hydroxyphenylboronic acid (83 mg, 0.53 mmol), sodium carbonate (140 mg, 1.32 mmol) and [1,1'-Bis(diphenylphosphino)ferrocene]dichloropalladium(II) (18 mg, 0.02 mmol) following the experimental procedure as described for Intermediate 2. The crude obtained was used in the next step without further purification.
LRMS (m/z): 258 (M+1)+

Intermediate 21. 2-(3-amino-6-(3-fluoro-2-hydroxyphenyl)-1H-indazol-1-yl)acetamide Obtained as a foam (89% of yield) from 2-(3-amino-6-bromo-1H-indazol-1-yl)acetamide (Intermediate 1; 100 mg, 0.37 mmol), 3-fluoro-2-hydroxyphenylboronic acid (69 mg, 0.44 mmol), sodium carbonate (118 mg, 1.11 mmol) and [1,1'-Bis(diphenylphosphino)ferrocene]dichloropalladium (II) (15 mg, 0.018 mmol) following the experimental procedure as described for Intermediate 2. The crude obtained was used in the next step without further purification.
LRMS (m/z): 301 (M+1)+

Intermediate 22. 2-(3-amino-6-(4-fluoro-2-hydroxyphenyl)-1H-indazol-1-yl)acetamide Obtained as a black solid (89% of yield) from 2-(3-amino-6-bromo-1H-indazol-1-yl)acetamide (Intermediate 1; 100 mg, 0.37 mmol), 4-fluoro-2-hydroxyphenylboronic acid (69 mg, 0.44 mmol), sodium carbonate (118 mg, 1.11 mmol) and [1,1'-Bis(diphenylphosphino)ferrocene]dichloropalladium (II) (15 mg, 0.018 mmol) following the experimental procedure as described for Intermediate 2. The crude obtained was used in the next step without further purification.
LRMS (m/z): 301 (M+1)+

Intermediate 23. 2-(3-amino-6-(2-fluoro-6-hydroxyphenyl)-1H-indazol-1-yl)acetamide Obtained as a black solid (86% of yield) from 2-(3-amino-6-bromo-1H-indazol-1-yl)acetamide (Intermediate 1; 100 mg, 0.37 mmol), 2-fluoro-6-hydroxyphenylboronic acid (69 mg, 0.44 mmol), sodium carbonate (118 mg, 1.11 mmol) and [1,1'-Bis(diphenylphosphino)ferrocene]dichloropalladium (II) (15 mg, 0.018 mmol) following the experimental procedure as described for Intermediate 2. The crude obtained was used in the next step without further purification.
LRMS (m/z): 301 (M+1)+

Intermediate 24. N,N-bis(2-((tert-butyldimethylsilyl)oxy)ethyl)-1-methyl-6-(2-(2,2,2-trifluoroethoxy)phenyl)-1H-indazol-3-amine To a solution of 1-methyl-6-(2-(2,2,2-trifluoroethoxy)phenyl)-1H-indazol-3-amine (Example 8; 64 mg, 0.20 mmol) in methanol (5 mL) was added few drops of acetic acid and 2-(tert-butyldimethylsilyloxy)acetaldehyde (40 μL, 0.24 mmol). The reaction mixture was stirred for half an hour and cyanoborohydride (17 mg, 0.27 mmol) was added (17 mg, 0.27 mmol). The reaction mixture was stirred overnight at room temperature. The solvent was removed under reduced pressure and the crude was partitioned between dichloromethane and sodium bicarbonate. The organic phase was dried, filtered and the solvent was removed under reduced pressure to give the title compound as foam (90% of yield). The title compound was used in the next step without further purification.
LRMS (m/z): 638 (M+1)+

Intermediate 25. 2-(3-amino-1-(3-(tert-butyldimethylsilyloxy)propyl)-1H-indazol-6-yl)-6-fluorophenol Obtained as a solid (99% of yield) from 6-bromo-1-(3-(tert-butyldimethylsilyloxy)propyl)-1H-indazol-3-amine (Intermediate 11; 150 mg, 0.39 mmol), 3-fluoro-2-hydroxyphenylboronic acid (67 mg, 0.42 mmol), sodium carbonate (124 mg, 1.17 mmol) and [1,1'-Bis(diphenylphosphino)ferrocene]dichloropalladium(II) (16 mg, 0.019 mmol) following the experimental procedure as described for Intermediate 2. The crude obtained was used in the next step without further purification.
LRMS (m/z): 416 (M+1)+

Intermediate 26. 1-(3-(tert-butyldimethylsilyloxy)propyl)-6-(3-fluoro-2-(2,2,2-trifluoroethoxy)phenyl)-1H-indazol-3-amine Obtained as a foam (95% of yield) from 2-(3-amino-1-(3-(tert-butyldimethylsilyloxy)propyl)-1H-indazol-6-yl)-6-fluorophenol (Intermediate 25; 81 mg, 0.19 mmol), cesium carbonate (190 mg, 0.58 mmol) and 2,2,2-trifluoroethyl trifluoromethanesulfonate (90 μL, 0.38 mmol) following the experimental procedure as described for Example 1. The crude obtained was used in the next step without further purification.
LRMS (m/z): 498 (M+1)+

Intermediate 27. 1-(3-(tert-butyldimethylsilyloxy)propyl)-6-(3-fluoro-2-(2,2,3,3,3-pentafluoropropoxy)phenyl)-1H-indazol-3-amine Obtained as a foam (97% of yield) from 2-(3-amino-1-(3-(tert-butyldimethylsilyloxy)propyl)-1H-indazol-6-yl)-6-fluorophenol (Intermediate 25; 81 mg, 0.19 mmol), cesium carbonate (190 mg, 0.58 mmol) and 2,2,3,3,3-pentafluoropropyl trifluoromethanesulfonate (109 μL, 0.38 mmol) following the experimental procedure as described for Example 1. The crude obtained was used in the next step without further purification.
LRMS (m/z): 548 (M+1)+

Intermediate 28. tert-butyl 3-(1-methyl-6-(2-(2,2,2-trifluoroethoxy)phenyl)-1H-indazol-3-ylamino)-3-oxopropylcarbamate A solution of 2-(1H-benzo[d][1,2,3]triazol-1-yl)-1,1,3,3-tetramethylisouronium tetrafluoroborate (44 mg, 0.13 mmol) and 1-Hydroxybenzotriazole hydrate (5 mg, 0.037 mmol) in dimethylformamide (2 mL) was placed in a sealed reactor and a solution of 3-(tert-butoxycarbonylamino)propanoic acid (37 mg, 0.19 mmol) and N,N-Diisopropylethylamine (104 μL, 0.59 mmol) in dimethylformamide (1 mL) were added. The mixture was stirred at room temperature for ten minutes and the solution of 1-methyl-6-(2-(2,2,2-trifluoroethoxy)phenyl)-1H-indazol-3-amine (Example 8; 64 mg, 0.19 mmol) was added. The reaction mixture was stirred at room temperature for two hours. Additional 0.7 eq of 1-Hydroxybenzotriazole hydrate and 2-(1H-benzo[d][1,2,3]triazol-1-yl)-1,1,3,3-tetramethylisouronium tetrafluoroborate were added into the reaction mixture and stirred overnight at room temperature.

The crude mixture was evaporated to dryness under reduced pressure and the crude was purified by preparative-HPLC using the described conditions in the general procedures. The title compound was obtained as a brown solid (38% of yield).
LRMS (m/z): 493 (M+1)+

Intermediate 29. tert-butyl 3-(6-(5-fluoro-2-(2,2,2-trifluoroethoxy)phenyl)-1-methyl-1H-indazol-3-ylamino)-3-oxopropylcarbamate Obtained as a white solid (52% of yield) from 6-(5-fluoro-2-(2,2,2-trifluoroethoxy)phenyl)-1-methyl-1H-indazol-3- amine (Example 10; 79 mg, 0.23 mmol), 2-(1H-benzo[d][1,2,3]triazol-1-yl)-1,1,3,3-tetramethylisouronium tetrafluoroborate (44 mg, 0.13 mmol), 1-Hydroxybenzotriazole hydrate (6 mg, 0.044 mmol), 3-(tert-butoxycarbonylamino)propanoic acid (44 mg, 0.23 mmol) and N,N-Diisopropylethylamine (121 µL, 0.69 mmol) following the experimental procedure as described for Intermediate 28. The crude was purified by preparative-HPLC using the described conditions in the general procedures.
LRMS (m/z): 511 (M+1)+

Intermediate 30. tert-butyl 2-(6-(5-fluoro-2-(2,2,3,3,3-pentafluoropropoxy)phenyl)-1-methyl-1H-indazol-3-ylamino)ethyl(methyl)carbamate Obtained as a foam (58% of yield) from 6-(5-fluoro-2-(2,2,3,3,3-pentafluoropropoxy)phenyl)-1-methyl-1H-indazol-3-amine (Example 4; 54 mg, 0.13 mmol), tert-butyl methyl(3-oxopropyl)carbamate (32 mg, 0.17 mmol) and cyanoborohydride (17 mg, 0.27 mmol) following the experimental procedure as described for Intermediate 24. The crude obtained was used in the next step without further purification.
LRMS (m/z): 547 (M+1)+

Intermediate 31. 2-(3-amino-1-(3-(tert-butyldimethylsilyloxy)propyl)-1H-indazol-6-yl)-3-fluorophenol Obtained as a foam (12% of yield) from 6-bromo-1-(3-(tert-butyldimethylsilyloxy)propyl)-1H-indazol-3-amine (Intermediate 11; 480 mg, 1.24 mmol), 2-fluoro-6-hydroxyphenylboronic acid (214 mg, 1.37 mmol), sodium carbonate (397 mg, 3.7 mmol) and [1,1'-Bis(diphenylphosphino)ferrocene]dichloropalladium(II) (50 mg, 0.06 mmol) following the experimental procedure as described for Intermediate 2. The crude obtained was purified by preparative-HPLC using the described conditions in the general procedures.
LRMS (m/z): 416 (M+1)+

Intermediate 32. 1-(3-(tert-butyldimethylsilyloxy)propyl)-6-(2-fluoro-6-(2,2,2-trifluoroethoxy)phenyl)-1H-indazol-3-amine Obtained as an oil (95% of yield) from 2-(3-amino-1-(3-(tert-butyldimethylsilyloxy)propyl)-1H-indazol-6-yl)-3-fluorophenol (Intermediate 31; 34 mg, 0.08 mmol), cesium carbonate (53 mg, 0.16 mmol) and 2,2,2-trifluoroethyl trifluoromethanesulfonate (37 µL, 0.16 mmol) following the experimental procedure as described for Example 1. The crude was used in the final step without further purification.
LRMS (m/z): 498 (M+1)+

Intermediate 33. 1-(3-(tert-butyldimethylsilyloxy)propyl)-6-(2-(2,2-difluoroethoxy)-6-fluorophenyl)-1H-indazol-3-amine Obtained as an oil (99% of yield) from 2-(3-amino-1-(3-(tert-butyldimethylsilyloxy)propyl)-1H-indazol-6-yl)-3-fluorophenol (Intermediate 31; 34 mg, 0.08 mmol), 2,2-difluoroethyl trifluoromethanesulfonate (35 µL, 0.16 mmol) and cesium carbonate (79 mg, 0.24 mmol) following the experimental procedure as described for Example 1. The crude was used in the next step without further purification.
LRMS (m/z): 480 (M+1)+

Intermediate 34. 2-(3-amino-1-methyl-1H-indazol-6-yl)-6-methoxyphenol

Obtained as brown solid (78% of yield) from 6-bromo-1-methyl-1H-indazol-3-amine (Intermediate 3; 75 mg, 0.33 mmol), 2-hydroxy-3-methoxyphenylboronic acid (50 mg, 0.29 mmol), sodium carbonate (105 mg, 0.99 mmol) and [1,1'-Bis(diphenylphosphino)ferrocene]dichloropalladium (II) (13 mg, 0.015 mmol) following the experimental procedure as described for Intermediate 2. The crude was used in the next step without further purification.
LRMS (m/z): 270 (M+1)+

Intermediate 35. 1-(3-(tert-butyldimethylsilyloxy)propyl)-6-(2-(2,2-difluoroethoxy)phenyl)-1H-indazol-3-amine Obtained as a foam (9% of yield) from 2-(3-amino-1-(3-(tert-butyldimethylsilyloxy)propyl)-1H-indazol-6-yl)phenol (Intermediate 12; 52 mg, 0.13 mmol), cesium carbonate (127 mg, 0.39 mmol) and 2,2-difluoroethyl trifluoromethanesulfonate (56 µL, 0.26 mmol) following the experimental procedure as described for Example 1. The crude obtained was purified by preparative-HPLC using the described conditions in the general procedures.
LRMS (m/z): 462 (M+1)+

Intermediate 36. tert-butyl 2-(6-(3-fluoro-2-(2,2,2-trifluoroethoxy)phenyl)-1-methyl-1H-indazol-3-ylamino)ethyl(methyl)carbamate Obtained as a foam (44% of yield) from 6-(3-fluoro-2-(2,2,2-trifluoroethoxy)phenyl)-1-methyl-1H-indazol-3-amine (Example 21; 60 mg, 0.17 mmol), tert-butyl methyl (2-oxoethyl)carbamate (36 mg, 0.21 mmol) and cyanoborohydride (22 mg, 0.35 mmol) following the experimental procedure as described for Intermediate 24. The crude was used in the next step without further purification.
LRMS (m/z): 497 (M+1)+

Intermediate 37. tert-butyl 4,4'-(2,2'-(6-(3-fluoro-2-(2,2,2-trifluoroethoxy)phenyl)-1-methyl-1H-indazol-3-ylazanediyl)bis(ethane-2,1-diyl))dipiperidine-1-carboxylate Obtained as an oil (50% of yield) from 6-(3-fluoro-2-(2,2,2-trifluoroethoxy)phenyl)-1-methyl-1H-indazol-3-amine (Example 21; 40 mg, 0.11 mmol), tert-butyl 4-(2-oxoethyl)piperidine-1-carboxylate (96 mg, 0.42 mmol) and cyanoborohydride (22 mg, 0.35 mmol) following the experimental procedure as described for Intermediate 24. The crude obtained was used in the next step without further purification.
LRMS (m/z): 762 (M+1)+

Intermediate 38. 6-(2-methoxypyridin-3-yl)-1-methyl-1H-indazol-3-amine

Obtained as a foam (88% of yield) from 6-bromo-1-methyl-1H-indazol-3-amine (Intermediate 3; 150 mg, 0.66 mmol), 2-methoxypyridin-3-ylboronic acid (111 mg, 0.72 mmol), sodium carbonate (210 mg, 1.99 mmol) and [1,1'-Bis(diphenylphosphino)ferrocene]dichloropalladium(II) (27 mg, 0.03 mmol) following the experimental procedure as described for Intermediate 2. The crude was purified by preparative-HPLC using the described conditions in the general procedures.
LRMS (m/z): 255 (M+1)+

Intermediate 39. 3-(3-amino-1-methyl-1H-indazol-6-yl)pyridin-2-ol 6-(2-methoxypyridin-3-yl)-1-methyl-1H-indazol-3-amine (Intermediate 38; 140 mg, 0.55 mmol) was dissolved in a solution of acid bromide (48% in water, 3 mL). The mixture was stirred for 1 hour at 120° C. The mixture was neutralized with sodium hydroxide until pH 7. The solvent was removed under reduced pressure and the crude was purified by preparative-HPLC using the conditions described in general procedures. The title compound was obtained as a white solid (23% of yield).
LRMS (m/z): 241 (M+1)$^+$ Intermediate 40. 3-(3-amino-6-bromo-1H-indazol-1-yl)propane-1,2-diol Obtained as an oil (95% of yield) from 6-bromo-1H-indazol-3-amine (650 mg, 3.06 mmol), 3-bromopropane-1,2-diol (950 mg, 6.13 mmol) and cesium carbonate (2.9 g, 9.1 mmol) following the experimental procedure as described for Intermediate 1. The crude obtained was used in the next step without further purification.
LRMS (m/z): 287 (M+1)$^+$ Intermediate 41. 3-(3-amino-6-(3-fluoro-2-hydroxyphenyl)-1H-indazol-1-yl)propane-1,2-diol Obtained as a black solid (44% of yield) from 3-(3-amino-6-bromo-1H-indazol-1-yl)propane-1,2-diol (Intermediate 40; 328 mg, 1.14 mmol), 3-fluoro-2-hydroxyphenylboronic acid (178 mg, 1.14 mmol), sodium carbonate (303 mg, 2.86 mmol) and [1,1'-Bis(diphenylphosphino)ferrocene]dichloropalladium(II) (47 mg, 0.05 mmol) following the experimental procedure as described for Intermediate 2. The crude was purified by preparative-HPLC using the described conditions in the general procedures.
LRMS (m/z): 318 (M+1)$^+$ Intermediate 42. 1-methyl-6-(4,4,5,5-tetramethyl-1,3,2-dioxaborolan-2-yl)-1H-indazol-3-amine A solution of 6-bromo-1-methyl-1H-indazol-3-amine (Intermediate 3; 250 mg, 1.1 mmol) in a mixture of dioxane:water (4:1; 5 mL) was degassed under Argon. Sodium carbonate (351 mg, 3.31 mmol) and [1,1'-Bis(diphenylphosphino)ferrocene]dichloropalladium(II) (45 mg, 0.05 mmol) were added into the solution and finally 4,4,4',4',5,5,5',5'-octamethyl-2,2'-bi(1,3,2-dioxaborolane) (307 mg, 1.2 mmol) was added into the mixture and it was degassed for several minutes under Argon. The reaction mixture was placed into a sealed reactor and heated at 110° C. for 2 hours. The reaction mixture was filtered and the solvent was evaporated under reduced pressure. The crude obtained was treated with ether giving a brown solid as the title compound (74% of yield), which was used in the next step without further purification.
LRMS (m/z): 274 (M+1)$^+$ Intermediate 43. tert-butyl 3-(3-amino-6-bromo-1H-indazol-1-yl)propylcarbamate Obtained as a red solid (98% of yield) from 6-bromo-1H-indazol-3-amine (250 mg, 1.17 mmol), tert-butyl 3-bromopropylcarbamate (308 mg, 1.29 mmol) and sodium hydride (51 mg, 2.12 mmol) following the experimental procedure as described for Intermediate 1. The crude obtained was used in the next step without further purification.
LRMS (m/z): 370 (M+1)$^+$ Intermediate 44. tert-butyl 3-(3-amino-6-(3-fluoro-2-hydroxyphenyl)-1H-indazol-1-yl)propylcarbamate Obtained as an oil (77% of yield) from tert-butyl 3-(3-amino-6-bromo-1H-indazol-1-yl)propylcarbamate (Intermediate 43; 70 mg, 0.18 mmol), 3-fluoro-2-hydroxyphenylboronic acid (32 mg, 0.20 mmol), sodium carbonate (60 mg, 0.56 mmol) and [1,1'-Bis(diphenylphosphino)ferrocene]dichloropalladium(II) (7 mg, 0.01 mmol) following the experimental procedure as described for Intermediate 2. The crude was used in the next step without further purification.
LRMS (m/z): 401 (M+1)$^+$ Intermediate 45. tert-butyl 3-(3-amino-6-(3-fluoro-2-(2,2,2-trifluoroethoxy)phenyl)-1H-indazol-1-yl)propylcarbamate Obtained as an oil (55% of yield) from tert-butyl 3-(3-amino-6-(3-fluoro-2-hydroxyphenyl)-1H-indazol-1-yl)propylcarbamate (Intermediate 44; 70 mg, 0.17 mmol), cesium carbonate (171 mg, 0.52 mmol) and 2,2,2-trifluoroethyl trifluoromethanesulfonate (38 µL, 0.26 mmol) following the experimental procedure as described for Example 1. The crude obtained was used in the next step without further purification.
LRMS (m/z): 483 (M+1)$^+$ Intermediate 46. 3-(3-amino-6-(2-fluoro-6-hydroxyphenyl)-1H-indazol-1-yl)propane-1,2-diol Obtained as a brown solid (12% of yield) from 3-(3-amino-6-bromo-1H-indazol-1-yl)propane-1,2-diol (Intermediate 41; 328 mg, 1.14 mmol), 2-fluoro-6-hydroxyphenylboronic acid (178 mg, 1.14 mmol), sodium carbonate (303 mg, 2.86 mmol) and [1,1'-Bis(diphenylphosphino)ferrocene]dichloropalladium(II) (47 mg, 0.05 mmol) following the experimental procedure as described for Intermediate 2. The crude was purified by preparative-HPLC using the described conditions in the general procedures.
LRMS (m/z): 318 (M+1)$^+$ Intermediate 47. N-(6-(2-(2,2-difluoroethoxy)-3-fluorophenyl)-1-methyl-1H-indazol-3-yl)-2,2,2-trifluoro-N-methylacetamide To a solution of N-(6-(2-(2,2-difluoroethoxy)-3-fluorophenyl)-1-methyl-1H-indazol-3-yl)-2,2,2-trifluoroacetamide (Example 56; 20 mg, 0.04 mmol) in dimethylformamide (1 mL) was added potassium carbonate (7 mg, 0.05 mmol) and methyl iodide (3 µL, 0.04 mmol). The reaction mixture was stirred for 2 hours at room temperature and then methyl iodide (2 µL, 0.04 mmol) was added into the reactor. The reaction mixture was stirred overnight at room temperature. The solvent was removed under reduced pressure and the crude obtained was partitioned between ether and water. The organic phase was dried, filtered and the solvent was removed under reduced pressure to give the title compound as an oil (91% of yield), which was used in the next step without further purification.
LRMS (m/z): 432 (M+1)$^+$ Intermediate 48. 2-(3-amino-6-bromo-1H-indazol-1-yl)ethanol Obtained as foam (40% of yield) from 6-bromo-1H-indazol-3-amine (0.5 gr, 2.35 mmol), 2-bromoethanol (252 uL, 3.55 mmol) and sodium hydride (60% in oil dispersion;

0.09 g, 3.75 mmol) following the experimental procedure as described for Example 1. The crude obtained was purified by preparative-HPLC using the described conditions in the general procedures.

LRMS (m/z): 257 (M+1)+

Intermediate 49. 1-(3-(tert-butyldimethylsilyloxy)propyl)-6-(2-(trifluoromethyl)phenyl)-1H-indazol-3-amine Obtained as a foam (41% of yield) from 6-bromo-1-(3-(tert-butyldimethylsilyloxy)propyl)-1H-indazol-3-amine (Intermediate 11; 100 mg, 0.26 mmol), 2-(trifluoromethyl)phenylboronic acid (54 mg, 0.28 mmol), sodium carbonate (82 mg, 0.78 mmol) and [1,1'-Bis(diphenylphosphino)ferrocene]dichloropalladium(II) (10 mg, 0.0513 mmol) following the experimental procedure as described for Intermediate 2. The crude was purified by preparative-HPLC using the described conditions in the general procedures.

LRMS (m/z): 450 (M+1)+

Intermediate 50. 1-(3-(tert-butyldimethylsilyloxy)propyl)-6-(2-(trifluoromethoxy)phenyl)-1H-indazol-3-amine Obtained as a foam (33% of yield) from 6-bromo-1-(3-(tert-butyldimethylsilyloxy)propyl)-1H-indazol-3-amine (Intermediate 11; 100 mg, 0.26 mmol), 2-(trifluoromethoxy)phenylboronic acid (58 mg, 0.28 mmol), sodium carbonate (82 mg, 0.78 mmol) and [1,1'-Bis(diphenylphosphino)ferrocene]dichloropalladium(II) (10 mg, 0.0513 mmol) following the experimental procedure as described for Intermediate 2. The crude was purified by preparative-HPLC using the described conditions in the general procedures.

LRMS (m/z): 466 (M+1)+

Intermediate 51. 6-(2-(trifluoromethoxy)phenyl-5,6-dihydro-1H-indazol-3-amine Obtained as a black solid (95% of yield) from 6-bromo-1H-indazol-3-amine (100 mg, 0.47 mmol), 2-(trifluoromethoxy)phenylboronic acid (106 mg, 0.52 mmol), sodium carbonate (149 mg, 1.41 mmol) and [1,1'-Bis(diphenylphosphino)ferrocene]dichloropalladium(II) (19 mg, 0.02 mmol) following the experimental procedure as described for Intermediate 2. The crude obtained was used in the next step without further purification.

LRMS (m/z): 296 (M+1)+

Intermediate 52. tert-butyl 3-(3-amino-6-(2-(trifluoromethoxy)phenyl)-1H-indazol-1-yl)propylcarbamate Obtained as a foam (95% of yield) from 6-(2-(trifluoromethoxy)phenyl-5,6-dihydro-1H-indazol-3-amine (Intermediate 51; 58 mg, 0.2 mmol) and sodium hydride (9 mg, 0.39 mmol) following the experimental procedure as described for Intermediate 1. The crude obtained was used in the next step without further purification.

LRMS (m/z): 451 (M+1)+

Intermediate 53. 2-chloro-6-(2-(trifluoromethyl)phenyl)nicotinonitrile

Obtained as a pale yellow solid (55% of yield) from 2,6-dichloronicotinonitrile (150 mg, 0.86 mmol), 2-(trifluoromethyl)phenylboronic acid (197 mg, 1.04 mmol), sodium carbonate (275 mg, 2.6 mmol) and [1,1'-Bis(diphenylphosphino)ferrocene]dichloropalladium(II) (36 mg, 0.043 mmol) following the experimental procedure as described for Intermediate 2. The crude was purified by preparative-HPLC using the described conditions in the general procedures.

LRMS (m/z): 283 (M+1)+

Intermediate 54. 6-(2-(trifluoromethyl)phenyl)-1H-pyrazolo[3,4-b]pyridin-3-amine To a solution of 2-chloro-6-(2-(trifluoromethyl)phenyl)nicotinonitrile (Intermediate 52; 150 mg, 0.49 mmol) in ⁱsopropanol (3 mL) was added hydrazine hydrate (1.5 mL, 1.5 mmol). The crude mixture was placed into a sealed microwave reactor and it was submitted for 20 minutes at 120° C. The solvent was removed under reduced pressure and the crude obtained was treated with a mixture of ether and ethyl acetate. The solid obtained was filtered giving the title compound as a white solid (70% of yield), which was used in the next step without further purification.

LRMS (m/z): 279(M+1)+

Intermediate 55. 1-(3-(tert-butyldimethylsilyloxy)propyl)-6-(2-(trifluoromethyl)phenyl)-1H-pyrazolo[3,4-b]pyridin-3-amine Obtained as a foam (98% of yield) from 6-(2-(trifluoromethyl)phenyl)-1H-pyrazolo[3,4-b]pyridin-3-amine (Intermediate 53; 54 mg, 0.19 mmol), cesium carbonate (126 mg, 0.38 mmol) and (3-bromopropoxy)(tert-butyl)dimethylsilane (54 mg, 0.21 mmol) following the experimental procedure as described for Intermediate 11. The crude obtained was used in the next step without further purification.

LRMS (m/z): 451(M+1)+

Intermediate 56. 3-chloro-5-(2-(trifluoromethyl)phenyl)pyrazine-2-carbonitrile Obtained as a black solid (95% of yield) from 3,5-dichloropyrazine-2-carbonitrile (100 mg, 0.57 mmol), 2-(trifluoromethyl)phenylboronic acid (109 mg, 0.57 mmol), sodium carbonate (182 mg, 1.72 mmol) and [1,1'-Bis(diphenylphosphino)ferrocene]dichloropalladium(II) (23 mg, 0.028 mmol) following the experimental procedure as described for Intermediate 2. The title compound was used in the next step without further purification.

LRMS (m/z): 284 (M+1)+

Intermediate 57. 6-(2-(trifluoromethyl)phenyl)-1H-pyrazolo[3,4-b]pyrazin-3-amine Obtained as a white solid (87% of yield) from 3-chloro-5-(2-(trifluoromethyl)phenyl)pyrazine-2-carbonitrile (Intermediate 56; 80 mg, 0.28 mmol) and hydrazine hydrate (400 μL) following the experimental procedure as described for Intermediate 53. The title compound was used in the next step without further purification.

LRMS (m/z): 280 (M+1)+

Intermediate 58. 3-chloro-5-(2-fluoro-6-methoxyphenyl)pyrazine-2-carbonitrile Obtained as a black solid (99% of yield) from 3,5-dichloropyrazine-2-carbonitrile (75 mg, 0.43 mmol), 2-fluoro-6-methoxyphenylboronic acid (73 mg, 0.43 mmol), sodium carbonate (137 mg, 1.3 mmol) and [1,1'-Bis(diphenylphosphino)ferrocene]dichloropalladium(II) (10 mg, 0.012 mmol) following the experimental procedure as described for Intermediate 2. The title compound was used in the next step without further manipulation.
LRMS (m/z): 264 (M+1)+

Intermediate 59. 6-(2-fluoro-6-methoxyphenyl)-1H-pyrazolo[3,4-b]pyrazin-3-amine Obtained as a yellow solid (29% of yield) from 3-chloro-5-(2-fluoro-6-methoxyphenyl)pyrazine-2-carbonitrile (Intermediate 58; 110 mg, 0.41 mmol) and Hydrazine Hydrate (0.5 mL, 0.45 mmol) following the experimental procedure as described for Intermediate 53. The title compound was used in the next step without further manipulation.
LRMS (m/z): 260 (M+1)+

Intermediate 60. 6-(2-fluoro-6-methoxyphenyl)-1-methyl-1H-pyrazolo[3,4-b]pyrazin-3-amine Obtained as an oil (66% of yield) from 6-(2-fluoro-6-methoxyphenyl)-1H-pyrazolo[3,4-b]pyrazin-3-amine (Intermediate 59; 30 mg, 0.11 mmol), iodomethane (7.9 µL, 0.12 mmol) and sodium hydride (5 mg, 0.21 mmol) following the experimental procedure as described for Intermediate 1. The crude obtained was used in the next step without further purification.
LRMS (m/z): 274 (M+1)+

Intermediate 61. 2-(3-amino-1-methyl-1H-pyrazolo[3,4-b]pyrazin-6-yl)-3-fluorophenol Obtained as a foam (95% of yield) from 6-(2-fluoro-6-methoxyphenyl)-1-methyl-1H-pyrazolo[3,4-b]pyrazin-3-amine (Intermediate 60; 25 mg, 0.09 mmol) and acid bromide (48% solution in water; 0.49 mL) following the experimental procedure as described for Intermediate 39. The crude obtained was used in the next step without further purification.
LRMS (m/z): 260 (M+1)+

Intermediate 62. tert-butyl 3-(3-amino-6-(3-fluoro-2-(2,2,3,3,3-pentafluoropropoxy)-phenyl)-1H-indazol-1-yl)propylcarbamate Obtained as red solid (96% of yield) from tert-butyl 3-(3-amino-6-(3-fluoro-2-hydroxyphenyl)-1H-indazol-1-yl)propylcarbamate (50 mg, 0.12 mmol), cesium carbonate (250 mg, 0.76 mmol) and 2,2,3,3,3-pentafluoropropyl trifluoromethanesulfonate (85 µL, 0.51 mmol) following the experimental procedure as described for Example 1. The title compound was used in the next step without further manipulation.
LRMS (m/z): 533 (M+1)+

Intermediate 63. 6-(3-methoxypyridin-4-yl)-1-methyl-1H-indazol-3-amine

Obtained as a white solid (88% of yield) from 6-bromo-1-methyl-1H-indazol-3-amine (Intermediate 3; 150 mg, 0.66 mmol), 3-methoxy-4-(4,4,5,5-tetramethyl-1,3,2-dioxaborolan-2-yl)pyridine (171 mg, 0.72 mmol), sodium carbonate (210 mg, 1.99 mmol) and [1,1'-Bis(diphenylphosphino)ferrocene]dichloropalladium(II) (27 mg, 0.033 mmol) following the experimental procedure as described for Intermediate 2. The crude obtained was purified by preparative-HPLC using the described conditions in the general procedures
LRMS (m/z): 255 (M+1)+

Intermediate 64. 4-(3-amino-1-methyl-1H-indazol-6-yl)pyridin-3-ol

Obtained as a foam (97% of yield) from 6-(3-methoxypyridin-4-yl)-1-methyl-1H-indazol-3-amine (Intermediate 63; 30 mg, 0.11 mmol) and acid bromide (48% in water, 0.89 mL) following the experimental procedure as described for Intermediate 39. The title compound obtained was used in the next step without further manipulation.
LRMS (m/z): 241 (M+1)+

Intermediate 65. tert-butyl 4-(6-(3-fluoro-2-(2,2,3,3,3-pentafluoropropoxy)phenyl)-1-methyl-1H-indazol-3-ylamino)cyclohexylcarbamate Obtained as a solid (29% of yield) from 6-(3-fluoro-2-(2,2,3,3,3-pentafluoropropoxy)phenyl)-1-methyl-1H-indazol-3-amine (Example 22; 40 mg, 0.10 mmol), tert-butyl 4-oxo-cyclohexylcarbamate (35 mg, 0.16 mmol), sodium triacetoxiborohydride (55 mg, 0.25 mmol) and acetic acid (18 µL, 0.31 mmol) following the experimental procedure as described for Intermediate 24. The title compound was used in the next step without further purification.
LRMS (m/z): 587 (M+1)+

Example 1. 2-(3-amino-6-(5-fluoro-2-(2,2,3,3,3-pentafluoropropoxy)phenyl)-1H-indazol-1-yl)acetamide To a mixture of 2-(3-amino-6-(5-fluoro-2-hydroxyphenyl)-1H-indazol-1-yl)acetamide (Intermediate 2, 30 mg, 0.09 mmol) in dimethylformamide (1 mL) was added cesium carbonate (70 mg, 0.2 mmol) and 2,2,3,3,3-pentafluoropropyl trifluoromethanesulfonate (23 µL, 0.13 mmol). The reaction mixture was stirred for 3 hours at 65° C. The crude was filtered and evaporated under reduced pressure. A foam was obtained, which was purified by preparative-HPLC using the described conditions in the general procedures. The title compound was obtained as a white solid (42% of yield).
LRMS (m/z): 433 (M+1)+
$^1$H NMR (300 MHz, DMSO-d$_6$) δ 4.66 (s, 2H), 4.79 (t, J=13.5 Hz, 2H), 5.51 (s, 2H), 7.07 (d, J=7.3 Hz, 1H), 7.24 (m, 3H), 7.41 (s, 1H), 7.67 (d, J=7.3 Hz, 1H).

Example 2. 2-(3-amino-6-(5-fluoro-2-(2,2,2-trifluoroethoxy)phenyl)-1H-indazol-1-yl)acetamide Obtained as white solid (10 mg, 36% of yield) from 2-(3-amino-6-(5-fluoro-2-hydroxyphenyl)-1H-indazol-1-yl) acetamide (Intermediate 2; 30 mg, 0.09 mmol), cesium carbonate (68 mg, 0.2 mmol) and 2,2,2-trifluoroethyl trifluoromethanesulfonate (20 µL, 0.13 mmol) following the experimental procedure as described for Example 1. The crude obtained was purified by preparative-HPLC using the described conditions in the general procedures.
LRMS (m/z): 383 (M+1)+
$^1$H NMR (300 MHz, DMSO-d$_6$) δ 4.66 (s, 2H), 4.68-4.79 (q, 2H), 5.51 (s, 2H), 7.09 (d, J=8.4 Hz, 1H), 7.18-7.31 (m, 3H), 7.43 (s, 1H), 7.68 (d, J=8.3 Hz, 1H).

Example 3. 6-(5-methoxy-2-(2,2,3,3,3-pentafluoropropoxy)phenyl)-1-methyl-1H-indazol-3-amine Obtained as a white solid (29% of yield) from 2-(3-amino-1-methyl-1H-indazol-6-yl)-4-methoxyphenol (Intermediate 4; 125 mg, 0.46 mmol), cesium carbonate (250 mg, 0.76 mmol) and 2,2,3,3,3-pentafluoropropyl trifluoromethanesulfonate (85 µL, 0.51 mmol) following the experimental procedure as described for Example 1. The crude obtained was purified by preparative-HPLC using the described conditions in the general procedures.

LRMS (m/z): 404 (M+1)$^+$ $^1$H NMR (300 MHz, CDCl$_3$) δ 3.83 (s, 2H), 3.86 (s, 3H), 4.17 (t, J=12.5 Hz, 2H), 6.87 (dd, J=8.9, 3.1 Hz, 1H), 6.97 (s, 1H), 7.00 (d, J=3.1 Hz, 1H), 7.16 (dd, J=8.4, 1.2 Hz, 1H), 7.39 (s, 1H), 7.56 (d, J=8.4 Hz, 1H).

Example 4. 6-(5-fluoro-2-(2,2,3,3,3-pentafluoropropoxy)phenyl)-1-methyl-1H-indazol-3-amine Obtained as a pale yellow solid (26% of yield) from 2-(3-amino-1-methyl-1H-indazol-6-yl)-4-fluorophenol (Intermediate 5, 30 mg, 0.11 mmol), cesium carbonate (101 mg, 0.31 mmol) and 2,2,3,3,3-pentafluoropropyl trifluoromethanesulfonate (34 µL, 0.20 mmol) following the experimental procedure as described for Example 1. The crude obtained was purified by preparative-HPLC using the described conditions in the general procedures.

LRMS (m/z): 390 (M+1)$^+$ $^1$H NMR (300 MHz, CDCl$_3$) δ 3.86 (s, 3H), 4.07 (s, 2H), 4.23 (t, J=12.4, 2H), 6.95-7.08 (m, 2H), 7.13 (dd, J=8.4, 1.3 Hz, 1H), 7.16-7.21 (m, 1H), 7.38 (d, 1H), 7.54-7.59 (m, 1H).

Example 5. 2-(3-amino-6-(2-(2,2,3,3,3-pentafluoropropoxy)phenyl)-1H-indazol-1-yl)acetamide Obtained as a foam (23% of yield) from 2-(3-amino-6-(2-hydroxyphenyl)-1H-indazol-1-yl)acetamide (Intermediate 6; 170 mg, 0.60 mmol), cesium carbonate (588 mg, 1.8 mmol) and 2,2,3,3,3-pentafluoropropyl trifluoromethanesulfonate (200 µL, 1.2 mmol) following the experimental procedure as described for Example 1. The crude obtained was purified by preparative-HPLC using the described conditions in the general procedures.

LRMS (m/z): 415 (M+1)$^+$ $^1$H NMR (300 MHz, CDCl$_3$) δ 4.22 (s, 2H), 4.37 (t, J=12.3 Hz, 2H), 4.83 (s, 2H), 7.01 (d, J=8.3 Hz, 1H), 7.17-7.23 (m, 2H), 7.37-7.47 (m, 3H), 7.58-7.63 (m, 1H).

Example 6. 2-(3-amino-6-(2-(2,2,2-trifluoroethoxy)phenyl)-1H-indazol-1-yl)acetamide Obtained as a brown solid (1.1% of yield) from 2-(3-amino-6-(2-hydroxyphenyl)-1H-indazol-1-yl)acetamide (Intermediate 6; 50 mg, 0.17 mmol), cesium carbonate (103 mg, 0.31 mmol) and 2,2,2-trifluoroethyl trifluoromethanesulfonate (30 µL, 0.2 mmol) following the experimental procedure as described for Example 1. The crude obtained was purified by preparative-HPLC using the described conditions in the general procedures.

LRMS (m/z): 365 (M+1)$^+$ $^1$H NMR (300 MHz, CDCl$_3$) δ 4.21 (s, 2H), 4.30 (q, J=8.1 Hz, 2H), 4.81 (s, 2H), 6.98 (d, J=8.2 Hz, 1H), 7.17 (t, J=7.6 Hz, 1H), 7.29 (s, 1H), 7.33-7.47 (m, 3H), 7.59 (d, J=8.4 Hz, 1H).

Example 7. 1-methyl-6-(2-(2,2,3,3,3-pentafluoropropoxy)phenyl)-1H-indazol-3-amine Obtained as a foam (35% of yield) from 2-(3-amino-1-methyl-1H-indazol-6-yl)phenol (Intermediate 7; 450 mg, 1.88 mmol), cesium carbonate (1.4 g, 4.2 mmol) and 2,2,3,3-pentafluoropropyl trifluoromethanesulfonate (370 µL, 2.2 mmol) following the experimental procedure as described for Example 1. The crude obtained was purified by preparative-HPLC using the described conditions in the general procedures.

LRMS (m/z): 372 (M+1)$^+$ $^1$H NMR (300 MHz, CDCl$_3$) δ 3.87 (s, 1H), 4.01 (d, J=4.6 Hz, 1H), 4.08 (s, 3H), 4.30-4.46 (m, 2H), 7.03 (d, J=8.2 Hz, 1H), 7.16-7.25 (m, 1H), 7.30-7.46 (m, 2H), 7.48 (dd, J=7.5, 1.7 Hz, 1H), 7.55 (bs, 1H), 7.58-7.66 (m, 1H).

Example 8. 1-methyl-6-(2-(2,2,2-trifluoroethoxy)phenyl)-1H-indazol-3-amine

Obtained as a white solid (47% of yield) from 2-(3-amino-1-methyl-1H-indazol-6-yl)phenol (Intermediate 7; 450 mg, 1.88 mmol), cesium carbonate (1.4 g, 4.2 mmol) and 2,2,2-trifluoroethyl trifluoromethanesulfonate (321 µL, 2.2 mmol) following the experimental procedure as described for Example 1. The crude obtained was purified by preparative-HPLC using the described conditions in the general procedures.

LRMS (m/z): 322 (M+1)$^+$ $^1$H NMR (300 MHz, CDCl$_3$) δ 3.86 (s, 3H), 4.27 (q, J=8.2 Hz, 2H), 7.01 (d, J=8.2 Hz, 1H), 7.14-7.21 (m, 2H), 7.32-7.39 (m, 1H), 7.40-7.42 (m, 1H), 7.47 (dd, J=7.6, 1.8 Hz, 1H), 7.56 (dd, J=8.4, 0.7 Hz, 1H).

Example 9. 6-(5-methoxy-2-(2,2,2-trifluoroethoxy)phenyl)-1-methyl-1H-indazol-3-amine Obtained as a solid (9% of yield) from 2-(3-amino-1-methyl-1H-indazol-6-yl)-4-methoxyphenol (Intermediate 4; 100 mg, 0.37 mmol), cesium carbonate (239 mg, 0.73 mmol) and 2,2,2-trifluoroethyl trifluoromethanesulfonate (70 µL, 0.48 mmol) following the experimental procedure as described for Example 1. The crude obtained was purified by preparative-HPLC using the described conditions in the general procedures.

LRMS (m/z): 352 (M+1)$^+$ $^1$H NMR (300 MHz, CDCl$_3$) δ 3.83 (s, 3H), 3.86 (s, 3H), 4.11 (q, J=8.3 Hz, 3H), 6.86 (dd, J=8.9, 3.1 Hz, 1H), 6.95-7.02 (m, 2H), 7.19 (dd, J=8.4, 1.3 Hz, 1H), 7.39-7.42 (bs, 1H), 7.57 (dd, J=8.4, 0.7 Hz, 1H).

Example 10. 6-(5-fluoro-2-(2,2,2-trifluoroethoxy)phenyl)-1-methyl-1H-indazol-3-amine Obtained as a pale yellow solid (37% of yield) from 2-(3-amino-1-methyl-1H-indazol-6-yl)-4-fluorophenol (Intermediate 5; 30 mg, 0.11 mmol), cesium carbonate (101 mg, 0.31 mmol) and 2,2,2-trifluoroethyl trifluoromethanesulfonate (29 µL, 0.20 mmol) following the experimental procedure as described for Example 1. The crude obtained was purified by preparative-HPLC using the described conditions in the general procedures.

LRMS (m/z): 340 (M+1)$^+$ $^1$H NMR (300 MHz, CDCl$_3$) δ 3.86 (s, 3H), 4.17 (q, J=8.2 Hz, 3H), 6.94-7.08 (m, 2H), 7.12-7.23 (m, 2H), 7.40 (s, 1H), 7.58 (d, J=8.3 Hz, 1H).

Example 11. 2-(1-methyl-6-(2-(2,2,2-trifluoroethoxy)phenyl)-1H-indazol-3-ylamino)-acetamide To a solution of 1-methyl-6-(2-(2,2,2-trifluoroethoxy)phenyl)-1H-indazol-3-amine (Example 8; 27 mg, 0.08 mmol) in dimethylformamide (1 mL) was added 2-bromoacetamide (24 mg, 0.17 mmol), cesium carbonate (84 mg, 0.25 mmol), potassium iodide (14 mg, 0.08 mmol) and tetrabutylammonium iodide (10 mg, 0.08 mmol). The reaction mixture was stirred for 4 hours at 95° C. The mixture was filtered. The filtrate was evaporated under reduced pressure and purified by Preparative-HPLC using conditions described in general procedures. The title compound was obtained as a brown solid (7% of yield).

LRMS (m/z): 379 (M+1)$^+$
$^1$H NMR (300 MHz, CDCl$_3$) δ 2.19 (d, J=0.6 Hz, 2H), 3.88 (s, 3H), 4.15 (s, 2H), 4.30 (q, J=8.1 Hz, 2H), 7.02 (d, J=8.2 Hz, 1H), 7.16-7.24 (m, 2H), 7.38 (t, J=7.7 Hz, 1H), 7.43 (s, 1H), 7.48 (d, J=7.4 Hz, 1H), 7.59 (d, J=8.3 Hz, 1H).

Example 12. 2-(1-methyl-6-(2-(2,2,3,3,3-pentafluoropropoxy)phenyl)-1H-indazol-3-ylamino)ethanol Obtained as a foam (2.4% of yield) from 1-methyl-6-(2-(2,2,3,3,3-pentafluoropropoxy)phenyl)-1H-indazol-3-amine (Example 7; 45 mg, 0.12 mmol), 2-bromoethanol (17 mg, 0.13 mmol), cesium carbonate (84 mg, 0.25 mmol), potassium iodide (14 mg, 0.08 mmol) and tetrabutylammonium iodide (10 mg, 0.08 mmol) following the experimental procedure as described for Example 11. The crude obtained was purified by preparative-HPLC using the described conditions in the general procedures.

LRMS (m/z): 416 (M+1)$^+$
$^1$H NMR (300 MHz, CDCl$_3$) δ 3.65 (bs, 2H), 3.86 (s, 3H), 3.91-4.00 (m, 2H), 4.28-4.41 (m, 3H), 7.03 (d, J=8.2 Hz, 1H), 7.13-7.23 (m, 2H), 7.35-7.42 (m, 2H), 7.48 (dd, J=7.4, 1.8 Hz, 1H), 7.55 (d, J=8.4 Hz, 1H).

Example 13. 2-(1-trifluoromethyl-6-(2-(2,2,2-trifluoroethoxy)phenyl)-1H-indazol-3-amine Obtained as a white solid (35% of yield) from 2-(3-amino-1-methyl-1H-indazol-6-yl)phenol (Intermediate 7; 25 mg, 0.08 mmol), cesium carbonate (60 mg, 0.15 mmol) and 2,2,2-trifluoroethyl trifluoromethanesulfonate (15 μL, 0.1 mmol) following the experimental procedure as described for Example 1. The crude obtained was purified by preparative-HPLC using the described conditions in the general procedures.

LRMS (m/z): 390 (M+1)$^+$
$^1$H NMR (300 MHz, CDCl$_3$) δ 4.19 (s, 2H), 4.31 (q, J=8.2 Hz, 2H), 4.72 (q, J=8.5 Hz, 2H), 7.02 (d, J=8.0 Hz, 1H), 7.20 (t, J=7.4 Hz, 1H), 7.31 (s, 1H), 7.39 (t, J=7.2 Hz, 1H), 7.47 (d, J=8.3 Hz, 2H), 7.61 (d, J=8.3 Hz, 1H).

Example 14. 6-(2-(2,2,3,3,3-pentafluoropropoxy)phenyl)-1H-indazol-3-amine

Obtained as a brown solid (36% of yield) from 2-(3-amino-1-(2-(tert-butyldimethylsilyloxy)ethyl)-1H-indazol-6-yl)phenol (Intermediate 9; 65 mg, 0.16 mmol), cesium carbonate (588 mg, 1.8 mmol) and 2,2,3,3,3-pentafluoropropyl trifluoromethanesulfonate (200 μL, 1.2 mmol) following the experimental procedure as described for Example 1. The crude obtained was purified by preparative-HPLC using the described conditions in the general procedures and deprotecting tert-butyldimethylsilyloxy)ethyl group under the purification conditions.

LRMS (m/z): 402 (M+1)$^+$
$^1$H NMR (300 MHz, CDCl$_3$) δ 3.96-4.05 (m, 2H), 4.24 (d, J=4.1 Hz, 2H), 4.32 (t, J=12.4 Hz, 2H), 6.98 (d, J=8.2 Hz, 1H), 7.15 (t, J=7.2 Hz, 2H), 7.20-7.27 (m, 1H), 7.28-7.48 (m, 2H), 7.54 (d, J=8.4 Hz, 1H).

Example 15. 2-(3-amino-6-(2-(2,2,2-trifluoroethoxy)phenyl)-1H-indazol-1-yl)ethanol Obtained as a foam (13% of yield) from 2-(3-amino-1-(2-(tert-butyldimethylsilyloxy)ethyl)-1H-indazol-6-yl)phenol (Intermediate 9; 65 mg, 0.16 mmol), cesium carbonate (165 mg, 0.33 mmol) and 2,2,2-trifluoroethyl trifluoromethanesulfonate (78 μL, 0.3 mmol) following the experimental procedure as described for Example 1. The crude obtained was purified by preparative-HPLC using the described conditions in the general procedures and deprotecting tert-butyldimethylsilyloxy)ethyl group under the purification conditions.

LRMS (m/z): 352 (M+1)$^+$
$^1$H NMR (300 MHz, CDCl$_3$) δ 3.97-4.02 (m, 2H), 4.20-4.28 (m, 4H), 6.97 (d, J=8.1 Hz, 1H), 7.15 (q, J=7.5 Hz, 2H), 7.29-7.37 (m, 1H), 7.42 (d, J=7.2 Hz, 2H), 7.55 (d, J=8.4 Hz, 1H), 8.03 (s, 1H).

Example 16. 6-(5-fluoro-2-(2,2,3,3,3-pentafluoropropoxy)phenyl)-1H-indazol-3-amine Obtained as a foam (9.6% of yield) from 2-(3-amino-1-(2-(tert-butyldimethylsilyloxy)ethyl)-1H-indazol-6-yl)-4-fluorophenol (Intermediate 10; 85 mg, 0.21 mmol), cesium carbonate (206 mg, 0.63 mmol) and 2,2,3,3,3-pentafluoropropyl trifluoromethanesulfonate (70 μL, 0.42 mmol) following the experimental procedure as described for Example 1. The crude obtained was purified by preparative-HPLC using the described conditions in the general procedures and deprotecting tert-butyldimethylsilyloxy)ethyl group under the purification conditions.

LRMS (m/z): 420 (M+1)$^+$
$^1$H NMR (300 MHz, CDCl$_3$) δ 3.96-4.06 (m, 2H), 4.22 (q, J=9.0, 8.5 Hz, 4H), 6.91-7.09 (m, 2H), 7.15 (d, J=8.3 Hz, 2H), 7.22-7.28 (m, 1H), 7.57 (d, J=8.3 Hz, 1H).

Example 17. 3-(3-amino-6-(2-(2,2,3,3,3-pentafluoropropoxy)phenyl)-1H-indazol-1-yl)propan-1-ol To a solution of 1-(3-(tert-butyldimethylsilyloxy)propyl)-6-(2-(2,2,3,3,3-pentafluoropropoxy)phenyl)-1H-indazol-3-amine (Intermediate 13; 95 mg, 0.17 mmol) was added triethylamine trihydrofluoride (146 μL, 0.89 mmol). The reaction mixture was stirred overnight at room temperature. The crude reaction was evaporated under reduced pressure and purified by Preparative-HPLC using the conditions described in general procedures to give the title compound as foam (25% of yield).

LRMS (m/z): 416 (M+1)$^+$
$^1$H NMR (300 MHz, CDCl$_3$) δ 1.34 (s, 1H), 2.01 (s, 2H), 3.46 (s, 2H), 4.29 (s, 2H), 6.97 (bs, 1H), 7.13 (bs, 2H), 7.24 (bs, 1H), 7.38 b(s, 2H), 7.52 (bs, 1H).

Example 18. 3-(3-amino-6-(5-fluoro-2-(2,2,2-trifluoroethoxy)phenyl)-1H-indazol-1-yl)propan-1-ol Obtained as a pale yellow solid (8.1% of yield) from 1-(3-(tert-butyldimethylsilyloxy)propyl)-6-(5-fluoro-2-(2,2,2-trifluoroethoxy)phenyl)-1H-indazol-3-amine (Intermediate 14; 96 mg, 0.19 mmol) and triethylamine trihydrofluoride (157 μL, 0.96 mmol) following the experimental procedure as described for Example 17. The crude obtained was purified by Preparative-HPLC using the conditions described in general procedures.

LRMS (m/z): 384 (M+1)⁺

¹H NMR (300 MHz, CDCl₃) δ 2.01 (d, J=5.5 Hz, 2H), 3.61 (s, 2H), 4.17 (q, J=8.1 Hz, 2H), 4.30 (s, 2H), 6.90-7.07 (m, 2H), 7.14 (d, J=8.4 Hz, 2H), 7.42 (s, 1H), 7.58 (d, J=8.4 Hz, 1H).

Example 19. 3-(3-amino-6-(5-fluoro-2-(2,2,3,3,3-pentafluoropropoxy)phenyl)-1H-indazol-1-yl)propan-1-ol Obtained as a brown solid (8% of yield) from 1-(3-(tert-butyldimethylsilyloxy)propyl)-6-(5-fluoro-2-(2,2,3,3,3-pentafluoropropoxy)phenyl)-1H-indazol-3-amine (Intermediate 16; 106 mf, 0.19 mmol) and trielthylamine trihydrofluoride (157 μL, 0.96 mmol) following the experimental procedure as described for Example 17. The crude obtained was purified by Preparative-HPLC using the conditions described in general procedures.

LRMS (m/z): 434 (M+1)⁺

¹H NMR (300 MHz, MeOD) δ 2.01 (s, 2H), 3.53 (s, 2H), 4.32 (s, 2H), 4.55 (s, 2H), 7.05-7.31 (m, 4H), 7.57 (s, 1H), 7.78 (s, 1H).

Example 20. 2-(6-(5-fluoro-2-(2,2,3,3,3-pentafluoropropoxy)phenyl)-3-(3-hydroxy-propylamino)-1H-indazol-1-yl)acetamide Obtained as a white solid (60% of yield) from 2-(6-(3-(tert-butyldimethyl-silyloxy)propylamino)-6-(5-fluoro-2-(2,2,3,3,3-pentafluoropropoxy)phenyl)-1H-indazol-1-yl)-acetamide (Intermediate 17; 29 mg, 0.04 mmol) and triethylamine trihydrofluoride (23 μL, 0.14 mmol) following the experimental procedure as described for Example 17. The crude obtained was purified by Preparative-HPLC using the conditions described in general procedures.

LRMS (m/z): 491(M+1)⁺

¹H NMR (300 MHz, CDCl₃) δ 1.94 (bs, 2H), 3.04 (bs, 2H), 3.72 (bs, 2H), 3.80 (s, 2H), 4.27 (t, J=11.9 Hz, 2H), 6.99 (d, J=4.4 Hz, 1H), 7.07 (s, 1H), 7.17 (dd, J=15.0, 8.8 Hz, 2H), 7.36 (s, 1H), 7.56 (d, J=8.6 Hz, 1H).

Example 21. 6-(3-fluoro-2-(2,2,2-trifluoroethoxy)phenyl)-1-methyl-1H-indazol-3-amine Obtained as a white solid (82% of yield) from 2-(3-amino-1-methyl-1H-indazol-6-yl)-6-fluorophenol (Intermediate 18; 300 mg, 1.16 mmol), cesium carbonate (1.1 mg, 3.37 mmol) and 2,2,2-trifluoroethyl trifluoromethanesulfonate (252 μL, 1.74 mmol) following the experimental procedure as described for Example 1. The crude obtained was purified by preparative-HPLC using the described conditions in the general procedures.

LRMS (m/z): 340 (M+1)⁺

¹H NMR (300 MHz, CDCl₃) δ 3.89 (s, 3H), 4.13 (q, J=8.4 Hz, 2H), 7.12-7.26 (m, 4H), 7.43 (s, 1H), 7.60 (d, J=8.4 Hz, 1H).

Example 22. 6-(3-fluoro-2-(2,2,3,3,3-pentafluoropropoxy)phenyl)-1-methyl-1H-indazol-3-amine Obtained as a white solid (11% of yield) from 2-(3-amino-1-methyl-1H-indazol-6-yl)-6-fluorophenol (Intermediate 18; 57 mg, 0.22 mmol), cesium carbonate (216 mg, 0.66 mmol) and 2,2,3,3,3-pentafluoropropyl trifluoromethanesulfonate (55 μL, 0.33 mmol) following the experimental procedure as described for Example 1. The crude obtained was purified by preparative-HPLC using the described conditions in the general procedures.

LRMS (m/z): 390 (M+1)⁺

¹H NMR (300 MHz, CDCl₃) δ 3.88 (s, 3H), 4.19 (t, J=12.7 Hz, 2H), 7.20 (m, 4H), 7.41 (s, 1H), 7.60 (d, J=8.3 Hz, 1H).

Example 23. 6-(4-fluoro-2-(2,2,3,3,3-pentafluoropropoxy)phenyl)-1-methyl-1H-indazol-3-amine Obtained as white solid (51% of yield) from 2-(3-amino-1-methyl-1H-indazol-6-yl)-5-fluorophenol (Intermediate 19; 32 mg, 0.12 mmol), cesium carbonate (121 mg, 0.37 mmol) and 2,2,3,3,3-pentafluoropropyl trifluoromethanesulfonate (30 μL, 0.18 mmol) following the experimental procedure as described for Example 1. The crude obtained was purified by preparative-HPLC using the described conditions in the general procedures.

LRMS (m/z): 390 (M+1)⁺

¹H NMR (300 MHz, CDCl₃) δ 3.86 (s, 3H), 4.34 (t, J=12.2 Hz, 2H), 6.76 (dd, J=10.1, 2.4 Hz, 1H), 6.91 (td, J=8.2, 2.4 Hz, 1H), 7.11 (dd, J=8.4, 1.3 Hz, 1H), 7.33 (s, 1H), 7.43 (dd, J=8.5, 6.6 Hz, 1H), 7.56 (d, J=8.4 Hz, 1H).

Example 24. 6-(2-fluoro-6-(2,2,3,3,3-pentafluoropropoxy)phenyl)-1-methyl-1H-indazol-3-amine Obtained as white solid (16% of yield) from 2-(3-amino-1-methyl-1H-indazol-6-yl)-3-fluorophenol (Intermediate 20; 57 mg, 0.22 mmol), cesium carbonate (216 mg, 0.66 mmol) and 2,2,3,3,3-pentafluoropropyl trifluoromethanesulfonate (55 μL, 0.33 mmol) following the experimental procedure as described for Example 1. The crude obtained was purified by preparative-HPLC using the described conditions in the general procedures.

LRMS (m/z): 390 (M+1)⁺

¹H NMR (300 MHz, CDCl₃) δ 3.86 (s, 3H), 4.33 (td, J=12.2, 1.1 Hz, 2H), 6.82 (d, J=8.4 Hz, 1H), 6.96 (td, J=8.8, 1.0 Hz, 1H), 7.05 (dt, J=8.4, 1.4 Hz, 1H), 7.30-7.38 (m, 2H), 7.58 (dd, J=8.3, 0.8 Hz, 1H).

Example 25. 6-(2-fluoro-6-(2,2,2-trifluoroethoxy)phenyl)-1-methyl-1H-indazol-3-amine Obtained as a pale yellow solid (28% of yield) from 2-(3-amino-1-methyl-1H-indazol-6-yl)-3-fluorophenol (Intermediate 20; 57 mg, 0.22 mmol), cesium carbonate (216 mg, 0.66 mmol) and 2,2,2-trifluoroethyl trifluoromethanesulfonate (48 μL, 0.33 mmol) following the experimental procedure as described for Example 1. The crude obtained was purified by preparative-HPLC using the described conditions in the general procedures.

LRMS (m/z): 340 (M+1)⁺

¹H NMR (300 MHz, CDCl₃) δ 3.87 (s, 3H), 4.27 (q, J=8.1 Hz, 2H), 6.82 (d, J=8.3 Hz, 1H), 6.96 (t, J=8.4 Hz, 1H), 7.08 (d, J=8.3 Hz, 1H), 7.28-7.38 (m, 2H), 7.60 (d, J=8.3 Hz, 1H).

Example 26. 2-(3-amino-6-(3-fluoro-2-(2,2,3,3,3-pentafluoropropoxy)phenyl)-1H-indazol-1-yl)acetamide Obtained as a white solid (42% of yield) from 2-(3-amino-6-(3-fluoro-2-hydroxyphenyl)-1H-indazol-1-yl)acetamide (Intermediate 21; 56 mg, 0.18 mmol), cesium carbonate (182 mg, 0.55 mmol) and 2,2,3,3,3-pentafluoropropyl trifluoromethanesulfonate (46 μL, 0.27 mmol) following the experimental procedure as described for Example 1. The crude obtained was purified by preparative-HPLC using the described conditions in the general procedures.

LRMS (m/z): 433 (M+1)$^+$ $^1$H NMR (300 MHz, CDCl$_3$) δ 4.25 (t, J=12.8 Hz, 2H), 4.83 (s, 2H), 7.14-7.23 (m, 3H), 7.24-7.26 (m, 1H), 7.40 (s, 1H), 7.63 (d, J=8.3 Hz, 1H).

Example 27. 3-(1-methyl-6-(2-(2,2,3,3,3-pentafluoropropoxy)phenyl)-1H-indazol-3-ylamino)propan-1-ol Obtained as a foam (14.4% of yield) from 1-methyl-6-(2-(2,2,3,3,3-pentafluoropropoxy)phenyl)-1H-indazol-3-amine (Example 7; 61 mg, 0.16 mmol), (3-bromopropoxy)(tert-butyl)dimethylsilane (96 μL, 0.41 mmol), cesium carbonate (104 mg, 0.31 mmol), potassium iodide (13 mg, 0.078 mmol) and tetrabutylammonium iodide (30 mg, 0.08 mmol) following the experimental procedure as described for Example 11. The crude obtained was purified by preparative-HPLC using the described conditions in the general procedures and deprotecting tert-butyldimethylsilyloxy) ethyl group under the purification conditions.

LRMS (m/z): 430 (M+1)$^+$ $^1$H NMR (300 MHz, CDCl$_3$) δ 1.90 (bs, 2H), 3.71-3.80 (m, 2H), 3.84 (s, 3H), 4.29-4.43 (m, 2H), 7.02 (d, J=8.2 Hz, 1H), 7.11-7.23 (m, 2H), 7.33-7.43 (m, 2H), 7.44-7.56 (m, 2H).

Example 28. 2-(3-amino-6-(3-fluoro-2-(2,2,2-trifluoroethoxy)phenyl)-1H-indazol-1-yl)acetamide Obtained as a foam (2% of yield) from 2-(3-amino-6-(3-fluoro-2-hydroxyphenyl)-1H-indazol-1-yl)acetamide (Intermediate 21; 56 mg, 0.18 mmol),), cesium carbonate (182 mg, 0.55 mmol) and 2,2,2-trifluoroethyl trifluoromethanesulfonate (40 μL, 0.27 mmol) following the experimental procedure as described for Example 1. The crude obtained was purified by preparative-HPLC using the described conditions in the general procedures.

LRMS (m/z): 383 (M+1)$^+$ $^1$H NMR (300 MHz, MeOD) δ 4.11-4.19 (m, 2H), 4.79 (s, 3H), 7.04 (d, J=7.6 Hz, 1H), 7.19 (d, J=13.9 Hz, 4H), 7.74 (d, J=8.3 Hz, 1H).

Example 29. 2-(3-amino-6-(4-fluoro-2-(2,2,3,3,3-pentafluoropropoxy)phenyl)-1H-indazol-1-yl)acetamide Obtained as solid (25% of yield) from 2-(3-amino-6-(4-fluoro-2-hydroxyphenyl)-1H-indazol-1-yl)acetamide (Intermediate 22; 56 mg, 0.18 mmol), cesium carbonate (182 mg, 0.55 mmol) and 2,2,3,3,3-pentafluoropropyl trifluoromethanesulfonate (46 μL, 0.27 mmol) following the experimental procedure as described for Example 1. The crude obtained was purified by preparative-HPLC using the described conditions in the general procedures.

LRMS (m/z): 433 (M+1)$^+$ $^1$H NMR (300 MHz, CDCl$_3$) δ 3.36 (bs, 2H), 4.33 (t, J=12.0 Hz, 2H), 4.74 (s, 2H), 6.70 (bs, 2H), 6.86 (bs, 1H), 7.16 (d, J=8.7 Hz, 2H), 7.35 (bs, 1H), 7.57 (d, J=8.5 Hz, 1H).

Example 30. 2-(3-amino-6-(4-fluoro-2-(2,2,2-trifluoroethoxy)phenyl)-1H-indazol-1-yl)acetamide Obtained as solid (42% of yield) from 2-(3-amino-6-(4-fluoro-2-hydroxyphenyl)-1H-indazol-1-yl)acetamide (Intermediate 22; 56 mg, 0.18 mmol), cesium carbonate (182 mg, 0.55 mmol) and 2,2,2-trifluoroethyl trifluoromethanesulfonate (40 μL, 0.27 mmol) following the experimental procedure as described for Example 1. The crude obtained was purified by preparative-HPLC using the described conditions in the general procedures.

LRMS (m/z): 383 (M+1)$^+$ $^1$H NMR (300 MHz, MeOD) δ 4.42 (q, J=8.2 Hz, 2H), 4.77 (s, 2H), 6.62 (t, J=8.3 Hz, 1H), 6.81-6.93 (m, 2H), 7.19 (d, J=8.5 Hz, 1H), 7.34-7.45 (m, 1H), 7.70 (d, J=8.3 Hz, 1H).

Example 31. 2-(3-amino-6-(2-fluoro-6-(2,2,2-trifluoroethoxy)phenyl)-1H-indazol-1-yl)acetamide Obtained as white solid (1.9% of yield) from 2-(3-amino-6-(2-fluoro-6-hydroxyphenyl)-1H-indazol-1-yl)acetamide (Intermediate 23; 56 mg, 0.18 mmol), cesium carbonate (182 mg, 0.55 mmol) and 2,2,2-trifluoroethyl trifluoromethanesulfonate (40 μL, 0.27 mmol) following the experimental procedure as described for Example 1. The crude obtained was purified by preparative-HPLC using the described conditions in the general procedures.

LRMS (m/z): 383 (M+1)$^+$ $^1$H NMR (300 MHz, CDCl$_3$) δ 3.27-3.54 (m, 2H), 4.26 (q, J=7.6 Hz, 2H), 4.75 (s, 2H), 6.77 (d, J=8.2 Hz, 1H), 6.86-6.98 (m, 1H), 7.12 (d, J=8.4 Hz, 1H), 7.34 (s, 2H), 7.61 (d, J=8.9 Hz, 1H).

Example 32. 2,2'-(1-methyl-6-(2-(2,2,2-trifluoroethoxy)phenyl)-1H-indazol-3-ylazanediyl)diethanol Obtained as foam (47% of yield) from N,N-bis(2-((tert-butyldimethylsilypoxy)ethyl)-1-methyl-6-(2-(2,2,2-trifluoroethoxy)phenyl)-1H-indazol-3-amine (Intermediate 24; 145 mg, 0.30 mmol) and triethylamine trihydrofluoride (250 μL, 1.5 mmol) following the experimental procedure as described for Example 17. The crude obtained was purified by preparative-HPLC using the described conditions in the general procedures.

LRMS (m/z): 410 (M+1)$^+$ $^1$H NMR (300 MHz, CDCl$_3$) δ 3.49 (s, 3H), 3.75 (s, 4H), 3.93 (q, J=7.1, 5.8 Hz, 4H), 4.30 (q, J=8.2 Hz, 2H), 7.01 (dd, J=8.2, 0.9 Hz, 1H), 7.14-7.24 (m, 2H), 7.34-7.41 (m, 2H), 7.47 (dd, J=7.6, 1.7 Hz, 1H), 7.81 (d, J=8.5 Hz, 1H).

Example 33. 3-(3-amino-6-(3-fluoro-2-(2,2,2-trifluoroethoxy)phenyl)-1H-indazol-1-yl)propan-1-ol Obtained as a foam (12% of yield) from 1-(3-(tert-butyldimethylsilyloxy)propyl)-6-(3-fluoro-2-(2,2,2-trifluoroethoxy)phenyl)-1H-indazol-3-amine (Intermediate 26; 96 mg, 0.19 mmol) and triethylamine trihydrofluoride (157 μL, 0.96 mmol) following the experimental procedure as described for Example 17. The crude obtained was purified by preparative-HPLC using the described conditions in the general procedures.

LRMS (m/z): 384 (M+1)$^+$ $^1$H NMR (300 MHz, MeOD) δ 2.04 (p, J=6.5 Hz, 2H), 3.56 (t, J=6.1 Hz, 2H), 4.22-4.30 (m, 2H), 4.33 (t, J=6.7 Hz, 2H), 7.20-7.33 (m, 3H), 7.54-7.60 (m, 1H), 7.61-7.72 (m, 1H), 7.79 (d, J=8.4 Hz, 1H).

Example 34. 3-(3-amino-6-(3-fluoro-2-(2,2,3,3,3-pentafluoropropoxy)phenyl)-1H-indazol-1-yl)propan-1-ol Obtained as a foam (23% of yield) from 1-(3-(tert-butyldimethylsilyloxy)propyl)-6-(3-fluoro-2-(2,2,3,3,3-pentafluoropropoxy)phenyl)-1H-indazol-3-amine (Intermediate 27; 106 mg, 0.19 mmol) and triethylamine trihydrofluoride (157 µL, 0.96 mmol) following the experimental procedure as described for Example 17. The crude obtained was purified by preparative-HPLC using the described conditions in the general procedures.

LRMS (m/z): 434 (M+1)$^+$ $^1$H NMR (300 MHz, MeOD) δ 2.03 (p, J=6.5 Hz, 2H), 3.55 (t, J=6.2 Hz, 2H), 4.24-4.36 (m, 4H), 7.16 (dd, J=8.4, 1.3 Hz, 1H), 7.20-7.32 (m, 3H), 7.50 (d, J=1.0 Hz, 1H), 7.75 (dd, J=8.4, 0.7 Hz, 1H).

Example 35. 3-((1-methyl-6-(2-(2,2,2-trifluoroethoxy)phenyl)-1H-indazol-3-yl)amino)-3-oxopropan-1-aminium 2,2,2-trifluoroacetate Tert-butyl 3-(1-methyl-6-(2-(2,2,2-trifluoroethoxy)phenyl)-1H-indazol-3-ylamino)-3-oxopropylcarbamate (Intermediate 28; 26 mg, 0.052 mmol) was dissolved in a mixture of dichloromethane and acid trifluoroacetic (1:1; 2 mL) and the mixture was stirred at room temperature for 1 hour. The solvent was removed under reduced pressure and the crude obtained was treated with ether. The solid obtained was filtered and dried to give the title compound as a trifluoroacetate salt (55% of yield).

LRMS (m/z): 393 (M+1)$^+$ $^1$H NMR (300 MHz, CDCl$_3$) δ 2.90 (d, J=5.9 Hz, 2H), 3.29 (bs, 2H), 3.95 (s, 3H), 4.27 (q, J=8.2 Hz, 2H), 6.96 (d, J=8.1 Hz, 1H), 7.14 (t, J=7.4 Hz, 1H), 7.33 (s, 1H), 7.42 (d, J=7.6 Hz, 1H), 7.49 (s, 1H), 7.81 (d, J=8.8 Hz, 1H).

Example 36. 3-((6-(5-fluoro-2-(2,2,2-trifluoroethoxy)phenyl)-1-methyl-1H-indazol-3-yl)amino)-3-oxopropan-1-aminium 2,2,2-trifluoroacetate Obtained as a white solid (40% of yield) from tert-butyl 3-(6-(5-fluoro-2-(2,2,2-trifluoroethoxy)phenyl)-1-methyl-1H-indazol-3-ylamino)-3-oxopropylcarbamate (Intermediate 29; 60 mg, 0.11 mmol) and a mixture of dichloromethane and acid trifluoroacetic (1:1; 2 mL) following the experimental procedure as described for Example 35. The title compound was obtained as a trifluoroacetate salt.

LRMS (m/z): 411 (M+1)$^+$ $^1$H NMR (300 MHz, DMSO-d$_6$) δ 2.80 (t, J=6.5 Hz, 2H), 3.08-3.20 (m, 2H), 3.97 (s, 3H), 4.78 (q, J=8.8 Hz, 2H), 7.21-7.32 (m, 3H), 7.37 (d, J=8.8 Hz, 1H), 7.71 (s, 1H), 7.89 (d, J=8.6 Hz, 1H).

Example 37. 2-((6-(5-fluoro-2-(2,2,3,3,3-pentafluoropropoxy)phenyl)-1-methyl-1H-indazol-3-yl)amino)-N-methylethanaminium 2,2,2-trifluoroacetate Obtained as a yellow oil (4% of yield) from tert-butyl 2-(6-(5-fluoro-2-(2,2,3,3,3-pentafluoropropoxy)phenyl)-1-methyl-1H-indazol-3-ylamino)ethyl(methyl)carbamate (Intermediate 30; 150 mg, 0.27 mmol) and a mixture of dichloromethane and acid trifluoroacetic (1:1; 2 mL) following the experimental procedure as described for Example 35. The title compound was obtained as a trifluoroacetate salt.

LRMS (m/z): 447 (M+1)$^+$ $^1$H NMR (300 MHz, DMSO-d$_6$) δ 2.48 (bs, 2H), 2.99 (bs, 2H), 3.38 (bs, 2H), 3.76 (s, 3H), 4.82 (t, J=13.4 Hz, 2H), 6.32 (bs, 1H), 7.05 (d, J=8.6 Hz, 1H), 7.27 (bs, 3H), 7.69 (d, J=8.4 Hz, 1H), 8.33 (s, 1H).

Example 38. 3-(3-amino-6-(2-fluoro-6-(2,2,2-trifluoroethoxy)phenyl)-1H-indazol-1-yl)propan-1-ol Obtained as a yellow oil (32% of yield) from 1-(3-(tert-butyldimethylsilyloxy)propyl)-6-(2-fluoro-6-(2,2,2-trifluoroethoxy)phenyl)-1H-indazol-3-amine (Intermediate 32; 40 mg, 0.08 mmol) and triethylamine trihydrofluoride (39 µL, 0.24 mmol) following the experimental procedure as described for Example 17. The crude obtained was purified by preparative-HPLC using the described conditions in the general procedures.

LRMS (m/z): 384 (M+1)$^+$ $^1$H NMR (300 MHz, MeOD) δ 2.02 (p, J=6.4 Hz, 2H), 3.56 (t, J=6.2 Hz, 2H), 4.27 (t, J=6.7 Hz, 2H), 4.52 (q, J=8.4 Hz, 2H), 6.91-7.07 (m, 3H), 7.40 (d, J=7.8 Hz, 2H), 7.72 (d, J=8.4 Hz, 1H).

Example 39. 3-(3-amino-6-(2-(2,2-difluoroethoxy)-6-fluorophenyl)-1H-indazol-1-yl)propan-1-ol Obtained as a white solid (21% of yield) from 1-(3-(tert-butyldimethylsilyloxy)propyl)-6-(2-(2,2-difluoroethoxy)-6-fluorophenyl)-1H-indazol-3-amine (Intermediate 33; 35 mg, 0.07 mmol) and triethylamine trihydrofluoride (1.19 µL, 0.01 mmol) following the experimental procedure as described for Example 17. The crude obtained was purified by preparative-HPLC using the described conditions in the general procedures.

LRMS (m/z): 366 (M+1)$^+$ $^1$H NMR (300 MHz, MeOD) δ 3.57 (t, J=6.2 Hz, 2H), 4.22 (dd, J=13.7, 3.9 Hz, 2H), 4.26-4.38 (m, 2H), 6.02 (tt, J=55.0, 3.8 Hz, 2H), 6.93 (ddd, J=9.3, 8.4, 0.9 Hz, 1H), 6.99 (d, J=8.5 Hz, 1H), 7.12 (d, J=8.4 Hz, 1H), 7.40 (td, J=8.4, 6.5 Hz, 1H), 7.47 (s, 1H), 7.78 (dd, J=8.4, 0.7 Hz, 1H).

Example 40. 6-(3-methoxy-2-(2,2,2-trifluoroethoxy)phenyl)-1-methyl-1H-indazol-3-amine Obtained as a white solid (51% of yield) from 2-(3-amino-1-methyl-1H-indazol-6-yl)-6-methoxyphenol (Intermediate 34; 40 mg, 0.14 mmol), cesium carbonate (145 mg, 0.44 mmol) and 2,2,2-trifluoroethyl trifluoromethanesulfonate (32 µL, 0.22 mmol) following the experimental procedure as described for Example 1. The crude obtained was purified by preparative-HPLC using the described conditions in the general procedures.

LRMS (m/z): 352 (M+1)$^+$ $^1$H NMR (300 MHz, CDCl$_3$) δ 3.88 (s, 3H), 3.96 (s, 3H), 4.10 (q, J=8.6 Hz, 2H), 7.03 (dd, J=27.0, 7.4 Hz, 2H), 7.22 (t, J=7.9 Hz, 2H), 7.45 (s, 1H), 7.58 (d, J=9.0 Hz, 1H).

Example 41. 6-(2-(2,2-difluoroethoxy)-3-methoxyphenyl)-1-methyl-1H-indazol-3-amine Obtained as a white solid (25% of yield) from 2-(3-amino-1-methyl-1H-indazol-6-yl)-6-methoxyphenol (Intermediate 34; 40 mg, 0.14 mmol), cesium carbonate (145 mg, 0.44 mmol) and 2,2-difluoroethyl trifluoromethanesulfonate (29 µL, 0.21 mmol) following the experimental procedure as described for Example 1. The crude obtained was purified by preparative-HPLC using the described conditions in the general procedures.

LRMS (m/z): 323 (M+1)$^+$ $^1$H NMR (300 MHz, CDCl$_3$) δ 3.88 (s, 3H), 3.95 (bs, 4H), 5.74 (t, J=55.8 Hz, 1H), 7.02 (dd, J=22.3, 7.7 Hz, 2H), 7.21 (d, J=6.7 Hz, 2H), 7.41 (s, 1H), 7.58 (d, J=8.5 Hz, 1H).

Example 42. 6-(2-(2,2-difluoroethoxy)-3-fluorophenyl)-1-methyl-1H-indazol-3-amine Obtained as a brown solid (18% of yield) from 2-(3-amino-1-methyl-1H-indazol-6-yl)-6-fluorophenol (Intermediate 18; 100 mg, 0.38 mmol), cesium carbonate (126 mg, 0.38 mmol) and 2,2-difluoroethyl trifluoromethanesulfonate (77 µL, 0.57 mmol) following the experimental procedure as described for Example 1. The crude obtained was purified by preparative-HPLC using the described conditions in the general procedures.

LRMS (m/z): 322 (M+1)$^+$
$^1$H NMR (300 MHz, CDCl$_3$) δ 3.89 (s, 3H), 3.94-4.09 (m, 2H), 5.79 (t, J=55.2 Hz, 1H), 7.19 (q, J=7.8, 6.9 Hz, 4H), 7.40 (s, 1H), 7.60 (d, J=8.3 Hz, 1H).

Example 43. 3-(3-amino-6-(2-(2,2-difluoroethoxy)phenyl)-1H-indazol-1-yl)propan-1-ol Obtained as an oil (44% of yield) from 1-(3-(tert-butyldimethylsilyloxy)propyl)-6-(2-(2,2-difluoroethoxy)phenyl)-1H-indazol-3-amine (Intermediate 35; 6 mg, 0.012 mmol) and triethylamine trihydrofluoride (2.12 µL, 0.01 mmol) following the experimental procedure as described for Example 17. The crude obtained was purified by preparative-HPLC using the described conditions in the general procedures.

LRMS (m/z): 348 (M+1)$^+$
$^1$H NMR (300 MHz, MeOD) δ 2.03 (bs, 2H), 3.55 (bs, 2H), 3.73 bs 2H), 4.19-4.38 (m, 1H), 5.88-6.37 (m, 2H), 6.86 (m, 2H), 7.17 (dd, J=22.1, 8.2 Hz, 2H), 7.29 (d, J=7.5 Hz, 1H), 7.48 (d, J=13.9 Hz, 1H), 7.57-7.73 (m, 1H).

Example 44. 6-(3-fluoro-2-(2,2,2-trifluoroethoxy)phenyl)-1-methyl-N-((1-methylpiperidin-4-yl)methyl)-1H-indazol-3-amine Obtained as a solid (4.5% of yield) from 6-(3-fluoro-2-(2,2,2-trifluoroethoxy)phenyl)-1-methyl-1H-indazol-3-amine (Example 21; 40 mg, 0.11 mmol), 1-methylpiperidine-4-carbaldehyde (27 mg, 0.21 mmol) and cyanoborohydride (22 mg, 0.35 mmol) following the experimental procedure as described for Intermediate 24. The crude was purified by preparative-HPLC using the described conditions in the general procedures.

LRMS (m/z): 451 (M+1)$^+$
$^1$H NMR (300 MHz, CDCl$_3$) δ 1.71 (d, J=12.9 Hz, 2H), 2.00 (bs, 2H), 2.66 (bs, 6H), 3.30-3.47 (m, 4H), 3.83 (s, 3H), 4.11 (q, J=7.9 Hz, 2H), 7.15 (dd, J=19.5, 10.1 Hz, 4H), 7.28 (s, 1H), 7.59 (d, J=8.4 Hz, 1H).

Example 45. 2-((6-(3-fluoro-2-(2,2,2-trifluoroethoxy)phenyl)-1-methyl-1H-indazol-3-yl)amino)-N-methylethanaminium 2,2,2-trifluoroacetate Obtained as a white solid (14% of yield) from tert-butyl 2-(6-(3-fluoro-2-(2,2,2-trifluoroethoxy)phenyl)-1-methyl-1H-indazol-3-ylamino)ethyl(methyl)carbamate (Intermediate 36; 40 mg, 0.08 mmol) and a mixture of dichloromethane and acid trifluoroacetic (1:1; 2 mL) following the experimental procedure as described for Example 35. The title compound was obtained as a trifluoroacetate salt.

LRMS (m/z): 397 (M+1)$^+$
$^1$H NMR (300 MHz, CDCl$_3$) δ 2.66 (d, J=8.8 Hz, 2H), 3.22 (s, 3H), 3.67 (s, 3H), 3.82 (d, J=7.3 Hz, 2H), 4.09 (q, J=8.1 Hz, 2H), 7.15 (dd, J=12.4, 5.8 Hz, 4H), 7.36 (d, J=7.4 Hz, 1H), 7.64 (d, J=8.0 Hz, 1H).

Example 46. 4,4'-(((6-(3-fluoro-2-(2,2,2-trifluoroethoxy)phenyl)-1-methyl-1H-indazol-3-yl)azanediyl)bis(ethane-2,1-diyl))bis(piperidin-1-ium) 2,2,2-trifluoroacetate Obtained as a white solid (13.8% of yield) from tert-butyl 4,4'-(2,2'-(6-(3-fluoro-2-(2,2,2-trifluoroethoxy)phenyl)-1-methyl-1H-indazol-3-ylazanediyl)bis(ethane-2,1-diyl))dipiperidine-1-carboxylate (Intermediate 37; 40 mg, 0.05 mmol) and a mixture of dichloromethane and acid trifluoroacetic (1:1; 2 mL) following the experimental procedure as described for Example 35. The title compound was obtained as a ditrifluoroacetate salt.

LRMS (m/z): 562 (M+1)$^+$
$^1$H NMR (300 MHz, CDCl$_3$) δ 1.47 (s, 4H), 1.61 (bs, 4H), 1.89 (bs, 4H), 2.77 (d, J=12.1 Hz, 6H), 3.34 (bs, 4H), 3.45 (s, 4H), 3.85 (s, 3H), 4.15 (q, J=8.0 Hz, 2H), 7.16 (dd, J=17.3, 10.1 Hz, 4H), 7.40 (s, 1H), 7.62 (d, J=8.3 Hz, 1H).

Example 47. 1-methyl-6-(2-(2,2,2-trifluoroethoxy)pyridin-3-yl)-1H-indazol-3-amine Obtained as a brown solid (19% of yield) from 3-(3-amino-1-methyl-1H-indazol-6-yl)pyridin-2-ol (Intermediate 39; 30 mg, 0.12 mmol), cesium carbonate (122 mg, 0.337 mmol) and 2,2,2-trifluoroethyl trifluoromethanesulfonate (57 µL, 0.24 mmol) following the experimental procedure as described for Example 1. The crude obtained was purified by preparative-HPLC using the described conditions in the general procedures.

LRMS (m/z): 323 (M+1)$^+$
$^1$H NMR (300 MHz, MeOD) δ 3.80 (s, 3H), 4.92 (bs, 2H), 7.18 (t, J=8.8 Hz, 2H), 7.50 (s, 1H), 7.72 (d, J=8.4 Hz, 1H), 7.88 (d, J=7.3 Hz, 1H), 8.18 (d, J=4.6 Hz, 1H).

Example 48. 3-(3-amino-6-(3-fluoro-2-(2,2,2-trifluoroethoxy)phenyl)-1H-indazol-1-yl)propane-1,2-diol Obtained as a white solid (25% of yield) from 3-(3-amino-6-(3-fluoro-2-hydroxyphenyl)-1H-indazol-1-yl)propane-1,2-diol (Intermediate 41; 50 mg, 0.16 mmol), cesium carbonate (122 mg, 0.337 mmol) and 2,2,2-trifluoroethyl trifluoromethanesulfonate (57 µL, 0.24 mmol) following the experimental procedure as described for Example 1. The crude obtained was purified by preparative-HPLC using the described conditions in the general procedures.

LRMS (m/z): 400 (M+1)$^+$
$^1$H NMR (300 MHz, MeOD) δ 3.56 (bs, 2H), 4.06 (bs, 2H), 4.15-4.35 (m, 3H), 7.14-7.33 (m, 4H), 7.55 (s, 1H), 7.74 (d, J=7.9 Hz, 1H).

Example 49. 6-(2-(2,2-difluoroethoxy)pyridin-3-yl)-1-methyl-1H-indazol-3-amine Obtained as a foam (4.6% of yield) from 3-(3-amino-1-methyl-1H-indazol-6-yl)pyridin-2-ol (Intermediate 39; 70 mg, 0.29 mmol), cesium carbonate (122 mg, 0.337 mmol) and 2,2-difluoroethyl trifluoromethanesulfonate (57 µL, 0.24 mmol) following the experimental procedure as described for Example 1. The crude obtained was purified by preparative-HPLC using the described conditions in the general procedures.

LRMS (m/z): 305 (M+1)$^+$

¹H NMR (300 MHz, CDCl₃) δ 3.89 (s, 3H), 4.55-4.71 (m, 2H), 5.93-6.39 (m, 1H), 7.05-7.13 (m, 1H), 7.21 (d, J=8.4 Hz, 1H), 7.45 (d, J=8.5 Hz, 1H), 7.60 (d, J=8.5 Hz, 1H), 7.77 (d, J=7.4 Hz, 1H), 8.17 (s, 1H).

Example 50. N-(6-(3-fluoro-2-(2,2,2-trifluoroethoxy)phenyl)-1-methyl-1H-indazol-3-yl)sulfonamide To a solution of 6-(3-fluoro-2-(2,2,2-trifluoroethoxy)phenyl)-1-methyl-1H-indazol-3-amine (Example 21; 200 mg, 0.58 mmol) in tetrahydrofuran (5 mL) was added pyridine (168 μL, 2.06 mmol) and sulfamoyl chloride (143 mg, 1.23 mmol). The reaction mixture was stirred for 30 minutes at 0° C. and for 2 hours at room temperature. The solvent was removed under reduced pressure and the crude obtained was partitioned between EthylAcetate and sodiumhydrogen carbonate (4% solution). The organic phase was washed with bicarbonate and water. The organic phase was dried, filtered and the solvent was removed under reduced pressure obtaining a brown solid, which was purified by preparative-HPLC using the described conditions in the general procedures. The title compound was obtained as a white solid (52% of yield).

LRMS (m/z): 419 (M+1)⁺

¹H NMR (300 MHz, CDCl₃) δ 4.05 (s, 3H), 4.20 (q, J=8.6 Hz, 2H), 5.06 (s, 2H), 7.21 (d, J=14.9 Hz, 3H), 7.34 (d, J=8.3 Hz, 1H), 7.60 (s, 1H), 7.86 (d, J=9.1 Hz, 1H).

Example 51. 1-(3-aminopropyl)-6-(3-fluoro-2-(2,2,2-trifluoroethoxy)phenyl)-1H-indazol-3-amine 2,2,2-trifluoroacetate Obtained as a white solid (21% of yield) from tert-butyl 3-(3-amino-6-(3-fluoro-2-(2,2,2-trifluoroethoxy)phenyl)-1H-indazol-1-yl)propylcarbamate (Intermediate 45; 60 mg, 0.12 mmol) and a mixture of dichloromethane and acid trifluoroacetic (1:1; 4 mL) following the experimental procedure as described for Example 35. The title compound was obtained as a trifluoroacetate salt.

LRMS (m/z): 383 (M+1)⁺

¹H NMR (300 MHz, CDCl₃) δ 2.20 (bs, 2H), 3.00 (bs, 2H), 4.07-4.22 (m, 2H), 4.23 (d, J=11.4 Hz, 2H), 7.17 (m, 4H), 7.41 (s, 1H), 7.64 (d, J=8.2 Hz, 1H).

Example 52. 3-(3-amino-6-(2-fluoro-6-(2,2,2-trifluoroethoxy)phenyl)-1H-indazol-1-yl)propane-1,2-diol Obtained as a solid (23% of yield) from 3-(3-amino-6-(2-fluoro-6-hydroxyphenyl)-1H-indazol-1-yl)propane-1,2-diol (Intermediate 46; 48 mg, 0.15 mmol), cesium carbonate (98 mg, 0.31 mmol) and 2,2,2-trifluoroethyl trifluoromethanesulfonate (38 μL, 0.16 mmol) following the experimental procedure as described for Example 1. The crude obtained was purified by preparative-HPLC using the described conditions in the general procedures.

LRMS (m/z): 400 (M+1)⁺

¹H NMR (300 MHz, MeOD) δ 3.53 (s, 2H), 4.05 (bs, 1H), 4.11-4.33 (m, 2H), 4.50 (q, J=8.5 Hz, 2H), 6.98 (dd, J=17.8, 8.5 Hz, 3H), 7.40 (d, J=8.7 Hz, 2H), 7.71 (d, J=8.3 Hz, 1H).

Example 53. N-(6-(3-fluoro-2-(2,2,2-trifluoroethoxy)phenyl)-1-methyl-1H-indazol-3-yl)-N-(methylsulfonyl)methanesulfonamide To a solution of 6-(3-fluoro-2-(2,2,2-trifluoroethoxy)phenyl)-1-methyl-1H-indazol-3-amine (Example 21; 80 mg, 0.23 mmol) in a mixture of dichloromethane and tetrahydrofuran (1:1, 10 mL) was added methansulfonyl chloride (17 μL, 0.21 mmol) and diethylisopropylamine (165 μL, 0.94 mmol). The reaction mixture was stirred at room temperature for 2 hours. The solvent was removed under reduced pressure and the crude obtained was partitioned between dichloromethane and water. The organic phase was washed two times with water and brine. The organic phase was dried, filtered and the solvent was removed under reduced pressure to give a brown solid, which was purified by preparative-HPLC using the described conditions in the general procedures. The title compound was obtained as a white solid (15% of yield).

LRMS (m/z): 496 (M+1)⁺

¹H NMR (300 MHz, CDCl₃) δ 3.63 (s, 6H), 4.15 (s, 3H), 4.17-4.27 (m, 2H), 7.23 (tq, J=1.2, 0.6 Hz, 2H), 7.43-7.48 (m, 2H), 7.67-7.75 (m, 2H).

Example 54. N-(6-(3-fluoro-2-(2,2,2-trifluoroethoxy)phenyl)-1-methyl-1H-indazol-3-yl)ethanesulfonamide Obtained as a foam (2.5% of yield) from 6-(3-fluoro-2-(2,2,2-trifluoroethoxy)phenyl)-1-methyl-1H-indazol-3-amine (Example 21; 80 mg, 0.23 mmol), ethanesulfonyl chloride (21 μL, 0.22 mmol) and diethylisopropylamine (165 μL, 0.94 mmol) following the experimental procedure as described for Example 53. The crude obtained was purified purified by preparative-HPLC using the described conditions in the general procedures.

LRMS (m/z): 432 (M+1)⁺

¹H NMR (300 MHz, CDCl₃) δ 1.48-1.55 (m, 3H), 3.34 (q, J=7.4 Hz, 2H), 4.03-4.07 (s, 3H), 4.19 (qd, J=8.3, 0.5 Hz, 2H), 7.15-7.26 (m, 3H), 7.33-7.37 (m, 1H), 7.58-7.63 (m, 1H), 7.95 (dd, J=8.5, 0.8 Hz, 1H).

Example 55. 6-(2-(2,2-difluoroethoxy)-3-fluorophenyl)-N,N,1-trimethyl-1H-indazol-3-amine Obtained as a white solid (22% of yield) from 6-(2-(2,2-difluoroethoxy)-3-fluorophenyl)-1-methyl-1H-indazol-3-amine (Example 42; 30 mg, 0.09 mmol), formaldehyde (15 mg, 0.19 mmol) and sodiumcianoborohydride (17 mg, 0.27 mmol) following the experimental procedure as described for Intermediate 24. The crude obtained was purified by preparative-HPLC using the described conditions in the general procedures.

LRMS (m/z): 350 (M+1)⁺

¹H NMR (300 MHz, CDCl₃) δ 3.15 (s, 6H), 3.92 (s, 3H), 4.01 (tdd, J=13.3, 4.2, 0.7 Hz, 2H), 5.80 (tt, J=55.2, 4.2 Hz, 1H), 7.09-7.27 (m, 4H), 7.37-7.45 (m, 1H), 7.83 (d, J=8.5 Hz, 1H).

Example 56. N-(6-(2-(2,2-difluoroethoxy)-3-fluorophenyl)-1-methyl-1H-indazol-3-yl)-2,2,2-trifluoroacetamide To a solution of 6-(2-(2,2-difluoroethoxy)-3-fluorophenyl)-1-methyl-1H-indazol-3-amine (Example 42; 65 mg, 0.20 mmol) in dichloromethane (1 mL) was added pyridine (28 μL, 0.34 mmol) and trifluoroacetic anhydride (34 μL, 0.24 mmol). The reaction mixture was stirred at 2 hours at room temperature. The crude reaction was washed with acid chloride (1N), saturated bicarbonate and brine. The organic phase was dried, filtered and the solvent was removed under reduced pressure to give the title compound as a solid (23% of yield), which was used in the next step without further purification.

LRMS (m/z): 418 (M+1)+

¹H NMR (300 MHz, CDCl₃) δ 3.99-4.13 (m, 5H), 5.82 (tt, J=55.0, 4.0 Hz, 1H), 7.11-7.25 (m, 3H), 7.33-7.37 (m, 1H), 7.56-7.62 (m, 1H), 8.10 (dd, J=8.6, 0.8 Hz, 1H).

Example 57. 6-(2-(2,2-difluoroethoxy)-3-fluorophenyl)-N,1-dimethyl-1H-indazol-3-amine To a solution of N-(6-(2-(2,2-difluoroethoxy)-3-fluorophenyl)-1-methyl-1H-indazol-3-yl)-2,2,2-trifluoro-N-methylacetamide (Intermediate 47; 20 mg, 0.04 mmol) in ethanol (0.5 mL) was added sodium ethoxide (22 μL, 0.28 mmol) and the mixture was stirred at room temperature overnight. The solvent was removed under reduced pressure and the crude obtained was partitioned between ethyl acetate and water. The organic phase was washed with brine and bicarbonate 4% solution. The organic phase was dried, filtered and the solvent was removed under reduced pressure giving a yellow gum, which was purified by preparative-HPLC using the described conditions in the general procedures to give the title compound as a white solid (45% of yield).

LRMS (m/z): 336 (M+1)+

¹H NMR (300 MHz, CDCl₃) δ 3.14 (s, 2H), 3.91 (s, 2H), 4.00 (td, J=13.3, 4.2 Hz, 2H), 5.78 (tt, J=55.2, 4.2 Hz, 1H), 7.06-7.26 (m, 4H), 7.37 (s, 1H), 7.52-7.61 (m, 1H).

Example 58. 6-(2-(difluoromethoxy)-3-fluorophenyl)-1-methyl-1H-indazol-3-amine Obtained as a foam (13% of yield) from 2-(3-amino-1-methyl-1H-indazol-6-yl)-6-fluorophenol (Intermediate 18; 30 mg, 0.11 mmol), methyl 2-chloro-2,2-difluoroacetate (19 μL, 0.18 mmol) and cesium carbonate (112 mg, 0.34 mmol) following the experimental procedure as described for Example 1. The crude obtained was purified by preparative-HPLC using the described conditions in the general procedures.

LRMS (m/z): 308 (M+1)+

¹H NMR (300 MHz, MeOD) d 3.83 (s, 3H), 6.52 (td, J=74.1, 0.9 Hz, 1H), 7.13 (dd, J=8.4, 1.3 Hz, 1H), 7.25-7.44 (m, 4H), 7.75 (dd, J=8.4, 0.8 Hz, 1H).

Example 59. N-methyl-1H-(6-(3-fluoro-2-(2,2,2-trifluoroethoxy)phenyl)-1-methyl-1H-indazol-3-yl)sulfamide Obtained as a white solid (25% of yield) from 6-(3-fluoro-2-(2,2,2-trifluoroethoxy)phenyl)-1-methyl-1H-indazol-3-amine (Example 21; 80 mg, 0.23 mmol), methylsulfamoyl chloride (18 μL, 0.23 mmol) and pyridine (165 μL, 0.94 mmol) following the experimental procedure as described for Example 50. The crude obtained was purified by preparative-HPLC using the described conditions in the general procedures.

LRMS (m/z): 433 (M+1)+

¹H NMR (300 MHz, CDCl₃) δ 2.91 (d, J=5.4 Hz, 3H), 4.03 (s, 3H), 4.12-4.25 (m, 2H), 7.16-7.28 (m, 3H), 7.30-7.36 (m, 1H), 7.57-7.63 (m, 1H), 7.85 (dd, J=8.5, 0.8 Hz, 1H).

Example 60. 1-methyl-6-(2-(trifluoromethoxy)phenyl)-1H-indazol-3-amine

Obtained as a white solid (58% of yield) from 6-bromo-1-methyl-1H-indazol-3-amine (Intermediate 3; 48 mg, 0.21 mmol), 2-(trifluoromethoxy)phenylboronic acid (49 mg, 0.23 mmol), sodium carbonate (63 mg, 0.59 mmol) and [1,1'-Bis(diphenylphosphino)ferrocene]dichloropalladium(II) (10 mg, 0.012 mmol) following the experimental procedure as described for Intermediate 2. The crude obtained was purified by preparative-HPLC using the described conditions in the general procedures.

LRMS (m/z): 308 (M+1)+

¹H NMR (300 MHz, DMSO-d₆) δ 3.73 (s, 3H), 5.48 (bs, 2H), 6.96 (dd, J=8.3, 1.4 Hz, 1H), 7.38 (dd, J=1.3, 0.8 Hz, 1H), 7.44-7.63 (m, 4H), 7.71 (dd, J=8.3, 0.7 Hz, 1H).

Example 61. 2-(3-amino-6-(2-(trifluoromethoxy)phenyl)-1H-indazol-1-yl)acetamide Obtained as a white solid (27% of yield) from 2-(3-amino-6-bromo-1H-indazol-1-yl)acetamide (Intermediate 1; 55 mg, 0.2 mmol), 2-(trifluoromethoxy)phenylboronic acid (45 mg, 0.21 mmol), sodium carbonate (58 mg, 0.54 mmol) and [1,1'-Bis(diphenylphosphino)ferrocene]dichloropalladium(II) (7 mg, 0.01 mmol) following the experimental procedure as described for Intermediate 2. The crude obtained was purified by preparative-HPLC using the described conditions in the general procedures.

LRMS (m/z): 351 (M+1)+

¹H NMR (300 MHz, DMSO-d₆) δ 4.69 (s, 2H), 5.53 (s, 2H), 7.00 (d, J=8.3 Hz, 1H), 7.14 (s, 1H), 7.30 (s, 1H), 7.39 (s, 1H), 7.44-7.59 (m, 4H), 7.73 (d, J=8.3 Hz, 1H).

Example 62. 2-(1-(2-amino-2-oxoethyl)-6-(2-(trifluoromethoxy)phenyl)-1H-indazol-3-ylamino)acetamide To a solution of 2-(1-(2-amino-2-oxoethyl)-6-(2-(trifluoromethoxy)phenyl)-1H-indazol-3-ylamino)acetamide (Example 62; 40 mg, 0.11 mmol) in dimethylformamide (1 mL) was added in portions sodium hydride (60% oil dispersion; 5 mg, 020 mmol) at 0° C. and the mixture was stirred for 30 minutes, then 2-bromoacetamide and tetrabutylammonium fluoride (15 mg, 0.05 mmol) were added into the solution. The reaction mixture was heated at 110° C. for 1 hour. The mixture was poured into water and filtered. The solid obtained was purified by preparative-HPLC using the described conditions in the general procedures to give the title compound as a white solid (23% of yield).

LRMS (m/z): 408 (M+1)+

¹H NMR (300 MHz, CDCl₃) δ 3.5 (s, 2H), 4.2 (s, 2H), 6.9 (d, J=8.2 Hz, 1H), 7.1 (s, 1H), 7.3 (bs, 2H), 7.5 (bs, 2H), 8.05 (d, J=8.5 Hz, 1H).

Example 63. 2-(3-(2-hydroxyethylamino)-6-(2-(trifluoromethoxy)phenyl)-1H-indazol-1-yl)acetamide Obtained as a white solid (22% of yield) from 2-(1-(2-amino-2-oxoethyl)-6-(2-(trifluoromethoxy)phenyl)-1H-indazol-3-ylamino)acetamide (Example 62; 40 mg, 0.11 mmol), 2-bromoethanol (9 uL. 0.12 mmol), sodium hydride (5 mg, 0.20 mmol), potassium iodide (10 mg, 0.06 mmol) and tetrabutylammonium fluoride (15 mg, 0.057 mmol) following the experimental procedure as described for Example 11. The crude obtained was purified by preparative-HPLC using the described conditions in the general procedures.

LRMS (m/z): 395 (M+1)+

¹H NMR (300 MHz, MeOD) δ 3.48-3.60 (m, 2H), 3.87 (bs, 2H), 4.60 (s, 2H), 7.10-7.20 (m, 1H), 7.38-7.55 (m, 3H), 7.54-7.66 (m, 2H), 7.77 (dd, J=8.3, 0.7 Hz, 1H).

Example 64. 2-(3-amino-6-(2-(trifluoromethyl)phenyl)-1H-indazol-1-yl)acetamide Obtained as a white solid (3% of yield) from 2-(3-amino-6-bromo-1H-indazol-1-yl)acetamide (Intermediate 1; 102 mg, 0.37 mmol), 2-(trifluoromethyl)phenylboronic acid (86 mg, 0.45 mmol), sodium carbonate (120 mg, 1.13 mmol) and [1,1'-Bis(diphenylphosphino)ferrocene]dichloropalladium(II) (15 mg, 0.018 mmol) following the experimental procedure as described for Intermediate 2. The crude obtained was purified by preparative-HPLC using the described conditions in the general procedures.

LRMS (m/z): 335 (M+1)$^+$ $^1$H NMR (300 MHz, MeOD) δ 4.36 (s, 2H), 7.03 (d, J=7.7 Hz, 1H), 7.19 (s, 1H), 7.41 (s, 1H), 7.47-7.86 (m, 4H).

Example 65. 2-(3-((2-aminoethyl)amino)-6-(2-(trifluoromethoxy)phenyl)-1H-indazol-1-yl)acetamide Obtained as a foam (1.6% of yield) from 2-(3-amino-6-(2-(trifluoromethoxy)phenyl)-1H-indazol-1-yl)acetamide (Example 61; 40 mg, 0.11 mmol), tert-butyl 2-bromoethylcarbamate (26 mg, 0.11 mmol), sodium hydride (5 mg, 0.20 mmol), potassium iodide (10 mg, 0.06 mmol) and tetrabutylammonium fluoride (15 mg, 0.057 mmol) following the experimental procedure as described for Example 11, deprotection of tert-butyl group was done during the reaction. The crude obtained was purified by preparative-HPLC using the described conditions in the general procedures.

LRMS (m/z): 395 (M+1)$^+$ $^1$H NMR (300 MHz, MeOD) δ 1.44 (bs, 2H), 3.58-3.77 (m, 2H), 4.62 (s, 2H), 7.16 (d, J=8.3 Hz, 1H), 7.36-7.63 (m, 5H), 7.75 (d, J=8.4 Hz, 1H), 8.44 (bs, 2H).

Example 66. 2-(3-amino-6-(2-(trifluoromethoxy)phenyl)-1H-indazol-1-yl)ethanol Obtained as a foam (8.5% of yield) from 2-(3-amino-6-bromo-1H-indazol-1-yl)ethanol (Intermediate 48; 130 mg, 0.50 mmol), 2-(trifluoromethoxy)phenylboronic acid (109 mg, 0.53 mmol), sodium carbonate (153 mg, 1.45 mmol) and [1,1'-Bis(diphenylphosphino)ferrocene]dichloropalladium(II) (20 mg, 0.024 mmol) following the experimental procedure as described for Intermediate 2. The crude obtained was purified by preparative-HPLC using the described conditions in the general procedures.

LRMS (m/z): 338 (M+1)$^+$ $^1$H NMR (300 MHz, CDCl$_3$) δ 3.47-3.67 (m, 2H), 3.79-3.96 (m, 2H), 7.09 (d, J=8.3 Hz, 1H), 7.27-7.38 (m, 3H), 7.38-7.45 (m, 2H), 7.54 (d, J=8.4 Hz, 1H).

Example 67. 3-(3-amino-6-(2-(trifluoromethyl)phenyl)-1H-indazol-1-yl)propan-1-ol Obtained as a foam (40% of yield) from 1-(3-(tert-butyldimethylsilyloxy)propyl)-6-(2-(trifluoromethyl)phenyl)-1H-indazol-3-amine (Intermediate 49; 50 mg, 0.111 mmol) and triethylamine trihydrofluoride (90 µL, 0.55 mmol) following the experimental procedure as described for Example 17. The crude obtained was purified by Preparative-HPLC using the conditions described in general procedures.

LRMS (m/z): 336 (M+1)$^+$ $^1$H NMR (300 MHz, MeOD) δ 2.01 (p, J=6.6 Hz, 2H), 3.53 (t, J=6.3 Hz, 2H), 4.26 (t, J=6.8 Hz, 2H), 6.95 (dd, J=8.3, 0.6 Hz, 1H), 7.28 (s, 1H), 7.43-7.49 (m, 1H), 7.52-7.68 (m, 2H), 7.70 (dd, J=8.3, 0.8 Hz, 1H), 7.81 (dd, J=7.8, 1.3 Hz, 1H).

Example 68. 3-(3-amino-6-(2-(trifluoromethoxy)phenyl)-1H-indazol-1-yl)propan-1-ol Obtained as a white solid (54% of yield) from 1-(3-(tert-butyldimethylsilyloxy)propyl)-6-(2-(trifluoromethoxy)phenyl)-1H-indazol-3-amine (Intermediate 50; 41 mg, 0.088 mmol) and triethylamine trihydrofluoride (71 µL, 0.44 mmol) following the experimental procedure as described for Example 17. The crude obtained was purified by Preparative-HPLC using the conditions described in general procedures.

LRMS (m/z): 352 (M+1)$^+$ $^1$H NMR (300 MHz, MeOD) δ 2.03 (p, J=6.6 Hz, 2H), 3.54 (t, J=6.2 Hz, 2H), 4.29 (t, J=6.8 Hz, 2H), 7.10 (dd, J=8.4, 1.3 Hz, 1H), 7.40-7.45 (m, 2H), 7.46-7.51 (m, 2H), 7.57-7.61 (m, 1H), 7.74 (dd, J=8.4, 0.8 Hz, 1H).

Example 69. 1-(3-aminopropyl)-6-(2-(trifluoromethoxy)phenyl)-1H-indazol-3-amine A solution of tert-butyl 3-(3-amino-6-(2-(trifluoromethoxy)phenyl)-1H-indazol-1-yl)propylcarbamate (Intermediate 51; 40 mg, 0.088 mmol) in acid chloride (4M in dioxane; 2 mL) was stirred overnight at room temperature. The solvent was removed under reduced pressure and the crude was purified by Preparative-HPLC using the conditions described in general procedures to give the title compound as the hydrochloride salt (15% of yield).

LRMS (m/z): 351 (M+1)$^+$ $^1$H NMR (300 MHz, MeOD) δ 2.12-2.28 (m, 2H), 2.94-3.05 (m, 2H), 4.39 (t, J=6.3 Hz, 2H), 7.22 (d, J=8.4 Hz, 1H), 7.54 (dt, J=23.2, 10.7 Hz, 5H), 7.81 (d, J=8.3 Hz, 1H).

Example 70. 1-methyl-6-(2-(trifluoromethyl)phenyl)-1H-pyrazolo[3,4-b]pyridin-3-amine Obtained as a foam (11% of yield) from 6-(2-(trifluoromethyl)phenyl)-1H-pyrazolo[3,4-b]pyridin-3-amine (Intermediate 53; 40 mg, 0.14 mmol), sodium hydride (60% dispersion in mineral oil; 8.6 mg, 0.35 mmol) and methyl iodide (9.8 µL, 0.15 mmol) following the experimental procedure as described for Intermediate 3. The crude obtained was purified by Preparative-HPLC using the conditions described in general procedures.

LRMS (m/z): 293 (M+1)$^+$ $^1$H NMR (300 MHz, MeOD) δ 3.86 (s, 2H), 7.11 (d, J=8.2 Hz, 1H), 7.59 (d, J=7.5 Hz, 1H), 7.70 (m, 2H), 7.85 (d, J=7.8 Hz, 1H), 8.19 (d, J=8.1 Hz, 1H).

Example 71. 3-(3-amino-6-(2-(trifluoromethyl)phenyl)-1H-pyrazolo[3,4-b]pyridin-1-yl)propan-1-ol Obtained as brown solid (14% of yield) from 1-(3-(tert-butyldimethylsilyloxy)propyl)-6-(2-(trifluoromethyl)phenyl)-1H-pyrazolo[3,4-b]pyridin-3-amine (Intermediate 54; 87 mg, 0.19 mmol) and triethylamine trihydrofluoride (94 µL, 0.57 mmol) following the experimental procedure as described for Example 17. The crude obtained was purified by Preparative-HPLC using the conditions described in general procedures.

LRMS (m/z): 337 (M+1)$^+$ $^1$H NMR (300 MHz, MeOD) δ 1.98-2.10 (m, 2H), 3.55 (t, J=6.4 Hz, 2H), 4.38 (t, J=6.7 Hz, 2H), 7.15 (d, J=8.2 Hz,

1H), 7.60 (d, J=7.1 Hz, 1H), 7.71 (dt, J=24.2, 7.6 Hz, 2H), 7.86 (d, J=7.9 Hz, 1H), 8.21 (d, J=8.1 Hz, 1H).

Example 72. 6-(3-fluoro-2-(trifluoromethyl)phenyl)-1-methyl-1H-indazol-3-amine Obtained as a brown solid (4.2% of yield) from 1-methyl-6-(4,4,5,5-tetramethyl-1,3,2-dioxaborolan-2-yl)-1H-indazol-3-amine (Intermediate 42; 200 mg, 0.73 mmol), 1-bromo-3-fluoro-2-(trifluoromethyl)benzene (93 mg, 0.38 mmol), sodium carbonate (111 mg, 1.05 mmol) and [1,1'-Bis(diphenylphosphino)ferrocene]dichloropalladium(II) (14 mg, 0.017 mmol) following the experimental procedure as described for Intermediate 2. The crude obtained was purified by preparative-HPLC using the described conditions in the general procedures.

LRMS (m/z): 310 (M+1)$^+$
$^1$H NMR (300 MHz, MeOD) δ 3.81 (s, 3H), 6.92 (dd, J=8.3, 0.9 Hz, 1H), 7.21-7.27 (m, 2H), 7.31-7.47 (m, 1H), 7.59-7.76 (m, 2H).

Example 73. 1-methyl-6-(2-(trifluoromethyl)phenyl)-1H-pyrazolo[3,4-b]pyrazin-3-amine Obtained as a yellow solid (7% of yield) from 6-(2-(trifluoromethyl)phenyl)-1H-pyrazolo[3,4-b]pyrazin-3-amine (Intermediate 57; 75 mg, 0.26 mmol), iodomethane (42 mg, 0.29 mg) and sodium hydride (21 mg, 0.89 mmol) following the experimental procedure as described for Intermediate 3. The crude obtained was purified by preparative-HPLC using the described conditions in the general procedures.

LRMS (m/z): 294 (M+1)$^+$
$^1$H NMR (300 MHz, MeOD) δ 3.85-3.94 (m, 3H), 7.66 (dd, J=7.5, 0.7 Hz, 1H), 7.70-7.86 (m, 3H), 7.87-7.96 (m, 1H), 8.45 (s, 1H).

Example 74. 1-methyl-6-(2-(trifluoromethyl)pyridin-3-yl)-1H-indazol-3-amine

Obtained as a yellow solid (45% of yield) from 6-bromo-1-methyl-1H-indazol-3-amine (Intermediate 3; 50 mg, 0.22 mmol), 2-(trifluoromethyl)pyridin-3-ylboronic acid (51 mg, 0.26 mmol), sodium carbonate (70 mg, 0.66 mmol) and [1,1'-Bis(diphenylphosphino)ferrocene]dichloropalladium (II) (9 mg, 0.011 mmol) following the experimental procedure as described for Intermediate 2. The crude obtained was purified by preparative-HPLC using the described conditions in the general procedures.

LRMS (m/z): 293 (M+1)$^+$
$^1$H NMR (300 MHz, MeOD) δ 3.82 (s, 3H), 6.94-6.99 (m, 1H), 7.29 (s, 1H), 7.70-7.78 (m, 2H), 7.96 (dd, J=7.9, 0.9 Hz, 1H), 8.73 (dd, J=4.8, 1.1 Hz, 1H).

Example 75. N,N-dimethyl-N'-(6-(3-fluoro-2-(2,2,2-trifluoroethoxy)phenyl)-1-methyl-1H-indazol-3-yl)sulfamide Obtained as a foam (5.6% of yield) from 6-(3-fluoro-2-(2,2,2-trifluoroethoxy)phenyl)-1-methyl-1H-indazol-3-amine (Example 21; 95 mg, 0.28 mmol), dimethylsulfamoyl chloride (63 µL, 0.58 mmol) and pyridine (80 µL, 0.98 mmol) following the experimental procedure as described for Example 50. The crude obtained was purified by preparative-HPLC using the described conditions in the general procedures.

LRMS (m/z): 447 (M+1)$^+$
$^1$H NMR (300 MHz, CDCl$_3$) δ 2.90 (s, 6H), 4.05 (s, 3H), 4.19 (q, J=8.2 Hz, 2H), 7.05 (bs, 1H), 7.14-7.26 (m, 3H), 7.33 (dd, J=8.5, 1.2 Hz, 1H), 7.58 (s, 1H), 7.99 (d, J=8.5 Hz, 1H).

Example 76. N-(6-(3-fluoro-2-(2,2,2-trifluoroethoxy)phenyl)-1-methyl-1H-indazol-3-yl)piperidine-1-sulfonamide Obtained as a foam (5.2% of yield) from 6-(3-fluoro-2-(2,2,2-trifluoroethoxy)phenyl)-1-methyl-1H-indazol-3-amine (Example 21; 95 mg, 0.28 mmol), piperidine-1-sulfonyl chloride (82 µL, 0.58 mmol) and pyridine (80 µL, 0.98 mmol) following the experimental procedure as described for Example 50. The crude obtained was purified by preparative-HPLC using the described conditions in the general procedures.

LRMS (m/z): 487 (M+1)$^+$
$^1$H NMR (300 MHz, CDCl$_3$) δ 1.58 (bs, 6H), 3.23-3.32 (m, 4H), 4.04 (s, 3H), 4.18 (q, J=8.4 Hz, 3H), 6.76 (bs, 1H), 7.14-7.27 (m, 3H), 7.32 (d, J=8.6 Hz, 1H), 7.57 (s, 1H), 8.01 (d, J=8.5 Hz, 1H).

Example 77. 6-(2-fluoro-6-(2,2,2-trifluoroethoxy)phenyl)-1-methyl-1H-pyrazolo[3,4-b]pyrazin-3-amine Obtained as a foam (19% of yield) from 2-(3-amino-1-methyl-1H-pyrazolo[3,4-b]pyrazin-6-yl)-3-fluorophenol (23 mg, 0.088 mmol), cesium carbonate (57 mg, 0.17 mmol) and 2,2,2-trifluoroethyl trifluoromethanesulfonate (22 µL, 0.099 mmol) following the experimental procedure as described for Example 1. The crude obtained was purified by preparative-HPLC using the described conditions in the general procedures.

LRMS (m/z): 342 (M+1)$^+$
$^1$H NMR (300 MHz, MeOD) δ 3.88-3.92 (m, 3H), 4.64 (q, J=8.4 Hz, 2H), 6.99-7.14 (m, 2H), 7.56 (td, J=8.5, 6.5 Hz, 1H), 8.42 (s, 1H).

Example 78. 1-(3-aminopropyl)-6-(3-fluoro-2-(2,2,3,3,3-pentafluoropropoxy)phenyl)-1H-indazol-3-amine Obtained as hydrochloride white solid salt (7.3% of yield) from tert-butyl 3-(3-amino-6-(3-fluoro-2-(2,2,3,3,3-pentafluoropropoxy)phenyl)-1H-indazol-1-yl)propylcarbamate (Intermediate 62; 80 mg, 0.15 mmol) and hydrochloric acid (4M in dioxane; 2 mL, 0.05 mol) following the experimental procedure as described for Intermediate 69. The crude obtained was purified by preparative-HPLC using the described conditions in the general procedures.

LRMS (m/z): 433 (M+1)$^+$
$^1$HNMR (300 MHz, MeOD) δ 2.18 (dt, J=13.4, 6.7 Hz, 2H), 2.95-3.05 (m, 2H), 4.25-4.41 (m, 4H), 7.19 (dd, J=8.4, 1.3 Hz, 1H), 7.23-7.32 (m, 3H), 7.51 (d, J=0.7 Hz, 1H), 7.78 (dd, J=8.4, 0.7 Hz, 1H).

Example 79. 1-methyl-6-(3-(2,2,2-trifluoroethoxy)pyridin-4-yl)-1H-indazol-3-amine Obtained as a yellow solid (8% of yield) from 4-(3-amino-1-methyl-1H-indazol-6-yl)pyridin-3-ol (Intermediate 64; 28 mg, 0.11 mmol), cesium carbonate (113 mg, 0.34 mmol) and 2,2,2-trifluoroethyl trifluoromethanesulfonate (29 µL, 0.12 mmol) following the experimental procedure as described for Example 1. The crude obtained was purified by preparative-HPLC using the described conditions in the general procedures.

LRMS (m/z): 323 (M+1)$^+$ $^1$H NMR (300 MHz, MeOD) δ 3.90 (s, 3H), 4.78-4.91 (m, 2H), 7.40 (dd, J=8.5, 1.4 Hz, 1H), 7.78-7.82 (m, 1H), 7.86-7.95 (m, 2H), 8.55 (d, J=5.4 Hz, 1H), 8.68 (s, 1H).

Example 80. 1-isopropyl-6-(2-(trifluoromethoxy)phenyl)-1H-indazol-3-amine

Obtained as a yellow solid (5.1% of yield) from 6-(2-(trifluoromethoxy)phenyl)-1H-indazol-3-amine (Intermediate 51; 50 mg, 0.17 mmol), 2-bromopropane (23 mg, 0.18 mmol) and cesium carbonate (111 mg, 0.34 mmol) following the experimental procedure as described for Example 1. The crude obtained was purified by preparative-HPLC using the described conditions in the general procedures.

LRMS (m/z): 336 (M+1)$^+$ $^1$H NMR (300 MHz, MeOD) δ 1.44-1.52 (m, 6H), 4.75 (p, J=6.7 Hz, 1H), 7.09 (dd, J=8.4, 1.3 Hz, 1H), 7.39-7.45 (m, 2H), 7.46-7.52 (m, 2H), 7.54-7.62 (m, 1H), 7.74 (dd, J=8.4, 0.8 Hz, 1H).

Example 81. 1-isobutyl-6-(2-(trifluoromethoxy)phenyl)-1H-indazol-3-amine

Obtained as a yellow solid (6.6% of yield) from 6-(2-(trifluoromethoxy)phenyl)-1H-indazol-3-amine (Intermediate 51; 50 mg, 0.17 mmol), 1-bromo-2-methylpropane (28 mg, 0.20 mmol) and cesium carbonate (166 mg, 0.51 mmol) following the experimental procedure as described for Example 1. The crude obtained was purified by preparative-HPLC using the described conditions in the general procedures.

LRMS (m/z): 350 (M+1)$^+$ $^1$H NMR (300 MHz, MeOD) δ 0.85-0.95 (m, 6H), 2.24 (dp, J=13.8, 6.9 Hz, 1H), 3.98 (d, J=7.3 Hz, 2H), 7.05-7.12 (m, 1H), 7.35-7.41 (m, 1H), 7.41-7.51 (m, 3H), 7.53-7.60 (m, 1H), 7.71-7.79 (m, 1H).

Example 82. 1-(2-methoxyethyl)-6-(2-(trifluoromethoxy)phenyl)-1H-indazol-3-amine Obtained as a white solid (4.6% of yield) from 6-(2-(trifluoromethoxy)phenyl)-1H-indazol-3-amine (Intermediate 51; 50 mg, 0.17 mmol), 1-bromo-2-methoxyethane (26 mg, 0.18 mmol) and cesium carbonate (166 mg, 0.51 mmol) following the experimental procedure as described for Example 1. The crude obtained was purified by preparative-HPLC using the described conditions in the general procedures.

LRMS (m/z): 352 (M+1)$^+$ $^1$H NMR (300 MHz, MeOD) δ 3.43 (s, 3H), 3.54-3.60 (m, 2H), 3.67-3.74 (m, 2H), 7.07 (dd, J=8.4, 1.4 Hz, 1H), 7.36 (dd, J=1.4, 0.8 Hz, 1H), 7.45-7.50 (m, 3H), 7.53-7.58 (m, 1H), 7.76 (dd, J=8.4, 0.8 Hz, 1H).

Example 83. 1-(pyridin-3-ylmethyl)-6-(2-(trifluoromethoxy)phenyl)-1H-indazol-3-amine Obtained as a white solid (4% of yield) from 6-(2-(trifluoromethoxy)phenyl)-1H-indazol-3-amine (Intermediate 51; 50 mg, 0.17 mmol), 3-(bromomethyl)pyridine (35 mg, 0.20 mmol) and cesium carbonate (166 mg, 0.51 mmol) following the experimental procedure as described for Example 1. The crude obtained was purified by preparative-HPLC using the described conditions in the general procedures.

LRMS (m/z): 385 (M+1)$^+$ $^1$H NMR (300 MHz, MeOD) δ 4.65 (s, 2H), 7.06-7.11 (m, 1H), 7.36 (dd, J=1.3, 0.7 Hz, 1H), 7.38-7.50 (m, 4H), 7.51-7.57 (m, 1H), 7.78 (dd, J=8.4, 0.6 Hz, 1H), 7.96 (dt, J=7.9, 1.5 Hz, 1H), 8.42 (d, J=4.3 Hz, 1H), 8.65 (s, 1H).

Example 84. 1-ethyl-6-(2-(trifluoromethoxy)phenyl)-1H-indazol-3-amine

Obtained as a solid (2.8% of yield) from 6-(2-(trifluoromethoxy)phenyl)-1H-indazol-3-amine (Intermediate 51; 50 mg, 0.17 mmol), bromoethane (22 mg, 0.2 mmol) and cesium carbonate (166 mg, 0.51 mmol) following the experimental procedure as described for Example 1. The crude obtained was purified by preparative-HPLC using the described conditions in the general procedures.

LRMS (m/z): 322 (M+1)$^+$ $^1$H NMR (300 MHz, MeOD) δ 1.31-1.42 (m, 3H), 4.24 (q, J=7.1 Hz, 2H), 7.09 (m, 1H), 7.37-7.41 (m, 1H), 7.42-7.46 (m, 1H), 7.46-7.51 (m, 2H), 7.56-7.61 (m, 1H), 7.75 (dd, J=8.4, 0.7 Hz, 1H).

Example 85. N-(6-(3-fluoro-2-(2,2,2-trifluoroethoxy)phenyl)-1-methyl-1H-indazol-3-yl)morpholine-4-sulfonamide Obtained as a foam (1.4% of yield) from 6-(3-fluoro-2-(2,2,2-trifluoroethoxy)phenyl)-1-methyl-1H-indazol-3-amine (Example 21; 95 mg, 0.28 mmol), morpholine-4-sulfonyl chloride (109 mg, 0.58 mmol) and pyridine (80 μL, 0.98 mmol) following the experimental procedure as described for Example 50. The crude obtained was purified by preparative-HPLC using the described conditions in the general procedures.

LRMS (m/z): 489 (M+1)$^+$ $^1$H NMR (300 MHz, MeOD) δ 3.27-3.32 (m, 4H), 3.65-3.71 (m, 4H), 4.04 (d, J=2.7 Hz, 3H), 4.20 (q, J=8.5 Hz, 2H), 7.16-7.35 (m, 5H), 7.59 (d, J=0.8 Hz, 1H).

Example 86. N-(6-(3-fluoro-2-(2,2,2-trifluoroethoxy)phenyl)-1-methyl-1H-indazol-3-yl)azetidine-1-sulfonamide Obtained as a foam (1.5% of yield) from 6-(3-fluoro-2-(2,2,2-trifluoroethoxy)phenyl)-1-methyl-1H-indazol-3-amine (Example 21; 95 mg, 0.28 mmol), azetidine-1-sulfonyl chloride (90 mg, 0.57 mmol) and pyridine (80 μL, 0.98 mmol) following the experimental procedure as described for Example 50. The crude obtained was purified by preparative-HPLC using the described conditions in the general procedures.

LRMS (m/z): 459 (M+1)$^+$ $^1$H NMR (300 MHz, MeOD) δ 2.00-2.13 (m, 2H), 3.02-3.13 (m, 2H), 4.02 (bs, 2H), 4.05-4.07 (m, 3H), 4.28 (q, J=8.6 Hz, 2H), 7.24-7.37 (m, 3H), 7.67-7.70 (m, 2H), 7.91 (dd, J=8.5, 0.8 Hz, 1H).

Example 87. 6-(3-fluoro-2-(2,2,3,3,3-pentafluoropropoxy)phenyl)-1-methyl-N-(tetrahydro-2H-pyran-4-yl)-1H-indazol-3-amine Obtained as a white solid (3.9% of yield) from 6-(3-fluoro-2-(2,2,3,3,3-pentafluoropropoxy)phenyl)-1-methyl-1H-indazol-3-amine (Example 22; 40 mg, 0.10 mmol), dihydro-2H-pyran-4(3H)-one (15 μL, 0.16 mmol), sodium triacetoxiborohydride (55 mg, 0.25 mmol) and acetic acid (18 μL, 0.31 mmol) following the experimental procedure as described for Intermediate 24. The crude obtained was purified by preparative-HPLC using the described conditions in the general procedures.

LRMS (m/z): 474 (M+1)+

$^1$H NMR (300 MHz, MeOD) δ 1.56-1.73 (m, 2H), 2.16 (dd, J=12.8, 2.0 Hz, 2H), 3.60 (td, J=11.7, 2.0 Hz, 2H), 3.84 (s, 3H), 4.04 (dd, J=9.0, 3.9 Hz, 2H), 4.29 (t, J=12.9 Hz, 2H), 7.12 (dd, J=8.4, 1.3 Hz, 1H), 7.23 (dd, J=7.6, 2.9 Hz, 1H), 7.29 (m, 2H), 7.43 (s, 1H), 7.78 (dd, J=8.4, 0.7 Hz, 1H).

Example 88. $N^1$-(6-(3-fluoro-2-(2,2,3,3,3-pentafluoropropoxy)phenyl)-1-methyl-1H-indazol-3-yl)cyclohexane-1,4-diamine 2,2,2-trifluoroacetate A solution of tert-butyl 4-(6-(3-fluoro-2-(2,2,3,3,3-pentafluoropropoxy)phenyl)-1-methyl-1H-indazol-3-ylamino)cyclohexylcarbamate (Example 22; 50 mg, 0.08 mol) in trifluoroacetic acid (2 mL) was stirred at room temperature for 2 hours. The solvent was removed under reduced pressure to give a crude, which was purified by preparative-HPLC using the described conditions in the general procedures. The title compound was obtained as a trifluoroacetate white solid salt (8% of yield).

LRMS (m/z): 487 (M+1)+

$^1$H NMR (300 MHz, MeOD) δ 1.35-1.54 (m, 2H), 1.62 (d, J=11.9 Hz, 2H), 2.15 (d, J=10.6 Hz, 2H), 2.37 (d, J=11.4 Hz, 2H), 3.14 (m, 1H), 3.63 (m, 1H), 3.84 (s, 3H), 4.29 (t, J=12.6 Hz, 2H), 7.12 (dd, J=8.3, 1.1 Hz, 1H), 7.24 (m, 3H), 7.43 (s, 1H), 7.75 (d, J=8.3 Hz, 1H).

Biological Testing

Assay Procedure Nav1.7 and Nav1.5 Screening Assay

Cell Lines

Stable cell lines expressing the full-length protein of the voltage-gated sodium channels Nav1.7 or Nav1.5, with or without one beta-1, beta-2, beta-3, or beta-4 subunit, are created by transfected CHO cells or HEK293 cells, or any other suitable cell line, with a vector construct containing the complete open reading frame under a suitable promoter, as well known in the art.

In Vitro Electrophysiology

Electrophysiological studies are performed with an IonWorks Quattro (Molecular Devices Corp.) automated patch-clamp electrophysiology platform as described by (Schroeder K et al. *Journal of Biomolecular Screening* 2003, 8 (1), 50-64). Buffers for the experiments have the following composition (mM): Internal solution; K-gluconate 100, KCl 40, MgCl$_2$ 3.2, HEPES 5, EGTA 3, pH 7.3. To this amphotericin B is added to final concentration of 0.1 mg/ml to generate access solution. External solution; Dulbecco's Phosphate buffered saline (D-PBS) NaCl 137.93, KCl 2.67, KH$_2$PO$_4$ 1.47, Na$_2$HPO$_4$ 8.06, CaCl$_2$ 0.90, MgCl$_2$ 0.49. Prior to the experiment the cells expressing the voltage-gated ion channel of interest are detached from the tissue culture flasks, centrifuged and resuspended in D-PBS. Compounds are prepared and serially diluted in DMSO and finally diluted 1:100 in D-PBS. Cells are exposed to compounds through the pipetting system integrated into the platform and the voltage-gated ion channel of interest is activated with specific voltage stimulation protocols. The following voltage stimulation protocol is used for testing compounds against the voltage-gated sodium channel Nav1.7; from a holding potential of –100 mV a train of eight 60 ms depolarising steps to –20 mV at a frequency of 14 Hz are employed followed by a further step to –20 mV for 2000 ms. After which the voltage is returned to –100 mV for 10 ms before another voltage step to –20 mV for 60 ms is applied. The following voltage stimulation protocol is used for testing compounds against the voltage-gated sodium channel Nav1.5; from a holding potential of –120 mV a train of twenty-six 120 ms depolarising steps to –20 mV at a frequency of 5 Hz are employed. Recordings are made before and after compound addition with the compound incubation time being 5 minutes.

Percent block was calculated for each concentration in duplicate for peak 1 and peak 10 and peak 1 and 25 for Nav 1.7 and Nav 1.5 respectively in order to assess compound activity at close and inactivated states and IC$_{50}$ curves were fitted to percent block as a function of concentration The results are shown in Table 1.

| Example | Na$_v$ 1.7 IC$_{50}$ (μM) | Na$_v$ 1.5 IC$_{50}$ (μM) |
| --- | --- | --- |
| Example 3 | 1.23 | >33 |
| Example 8 | 0.32 | >33 |
| Example 12 | 0.82 | >33 |
| Example 14 | 0.56 | 8 |
| Example 22 | 0.10 | >33 |
| Example 24 | 0.56 | >33 |
| Example 27 | 1.5 | 19.8 |
| Example 26 | 3.65 | — |
| Example 40 | 0.20 | >33 |
| Example 41 | 1.07 | >33 |
| Example 42 | 0.29 | 23 |
| Example 44 | 1.86 | 4.5 |
| Example 47 | 2.37 | >33 |
| Exmaple 57 | 1.3 | >33 |
| Example 58 | 0.86 | >33 |
| Example 67 | 0.74 | 30 |
| Example 68 | 0.2 | 25 |
| Example 82 | 2 | — |

It can be seen from Table 1 that the compounds of Formula (I) are potent "activity". Preferred compounds of the invention possess an IC$_{50}$ value for Nav1.7 inhibition less than 5 μM, preferably less than 3 μM and most preferably less than 1 μM. On the other hand, compounds of Formula(I) exhibit a high selectivity with respect to Nav1.5

Combinations

The compounds of the present invention may also be combined with other active compounds, such as those mentioned above, in the treatment of a pathological condition or disease as hereinabove described.

The active compounds in the combination product may be administered together in the same pharmaceutical composition or in different compositions intended for separate, simultaneous, concomitant or sequential administration by the same or a different route.

It is contemplated that all active agents would be administered at the same time, or very close in time. Alternatively, one or two actives could be administered in the morning and the other (s) later in the day. Or in another scenario, one or two actives could be administered twice daily and the other (s) once daily, either at the same time as one of the twice-a-day dosing occurred, or separately. Preferably at least two, and more preferably all, of the actives would be administered together at the same time. Preferably, at least two, and more preferably all actives would be administered as an admixture.

The invention is also directed to a combination product of the compounds of the invention together with one or more other therapeutic agents for use in the treatment of a pathological condition or disease as hereinabove described.

The invention also encompasses the use of a combination of the compounds of the invention together with one or more other therapeutic agents for the manufacture of a formulation or medicament for treating these diseases.

The invention also provides a method of treatment of a pathological condition or disease as hereinabove described comprising administering a therapeutically effective amount of a combination of the compounds of the invention together with one or more other therapeutic agents, such as (a) Opioid receptor agonists such as but not restricted to morphine, phentanyl, hydromorphone or hydrocodone, (b) Opioid receptor partial agonists such as but not restricted to meptazinol, (c) NSAIDS such as but not restricted to acetyl salicilic acid, ibuprofen, naproxen, aceclofenac or diclofenac, (d) COX-2 inhibitors such as but not restricted to rofecoxib or celecoxib, (e) Ion channel modulators such as but not restricted to ziconotide or gabapentin, (f) Centrally acting agents such as but not restricted to flupirtine or neofam, (g) Agents for neuropathic pain such as but not restricted to carbamazepine, gabapentine, duloxetine or pregabaline, (h) Agents for cancer pain such as but not restricted to calcitonine, lexidronam or oxycodone for pain patients (i) Anti-fibrotics such as but not restricted to pirfenidone, nintenadib for patients with idiopathic pulmonary fibrosis, (j) Prostacyclin analogues such as but not restricted to epoprostenol, beraprost, treprostinil or iloprost (k) Endothelin antagonists such as but not restricted to bosentac, sitaxentan, ambrisentan or macitentan, (l) Phosphodiesterase V inhibitdors such as but not restricted to sildenafil or taldenafil, (m) Guanylate cyclase stimulators such as but not restricted to riociguat for patients with pulmonary hypertension, (n) Oral and inhaled corticosteroids such as but not restricted to fluticasone (o) Phosphodiesterase IV inhibitors like roflumilast, (p) Beta2-adrenoceptor agonists such as but not restricted to salbutamol, salmeterol, indacaterol or olodaterol, (q) Muscarinic antagonists such as but not restricted to ipratropium, tiotropium, aclidinium, glycopyrronium or umeclidinium, (r) Xantines such as but not restricted to teophyline, (s) Mast cell stabilizers such as but not restricted to tranilast and tazonilast, (t) Leukotriene modifiers such as but not restricted to montelukast, zafirlukast and zileuton, (u) Th2 cytokine inhibidors such as but not restricted to suplatast, (v) Thromboxane antagonists/thromboxane synthase inhibidors such as but not restricted to ozagrel and seratrodast, (w) Anti-IgE therapy compounds such as but not restricted to xolair for patients with asthma (x) Histamine antagonists such as but not restricted to ebastine, cetiricine and loratadine, (y) Antiinflammatory agents (such as NSAIDs, corticosteroids, calcineurin inhibitors, anti-TNF, anti-IL17, anti-IL12/IL13, anti-IL5, anti IL4/IL-13, anti-IL31 or anti-IgE antibodies, (z) JAK inhibitors such as but not restricted to ruxolitinib or tofacitinib, (aa) Syk inhibitors (ab) Immunosupressants;

(ac) Antipruritic agents such as kappa opioid agonists, mu opioid agonists, neurokinin receptor 1 antagonists such as but not restricted to aprepitant, 5-HT3 antagonists and, cannabinoids for patients with dermatological diseases (ad) Anti-tussive agents; Decongestants; Mucolytics; Expectorants; or Proton Pump Inhibitors, for simultaneous, separate or sequential use in the treatment of the human or animal body.

The active compounds in the combinations of the invention may be administered by any suitable route, depending on the nature of the disorder to be treated, e.g. orally (as syrups, tablets, capsules, lozenges, controlled-release preparations, fast-dissolving preparations, etc); topically (as creams, ointments, lotions, nasal sprays or aerosols, etc); by injection (subcutaneous, intradermic, intramuscular, intravenous, etc.) or by inhalation (as a dry powder, a solution, a dispersion, etc).

The active compounds in the combination, i.e. the aminoindazole derivatives of the invention, and the other optional active compounds may be administered together in the same pharmaceutical composition or in different compositions intended for separate, simultaneous, concomitant or sequential administration by the same or a different route.

One execution of the present invention consists of a kit of parts comprising a aminoindazole derivative of the invention together with instructions for simultaneous, concurrent, separate or sequential use in combination with another active compound useful in the treatment of above mentioned diseases.

Another execution of the present invention consists of a package comprising an aminoindazole derivative of the invention and another active compound useful in the treatment of these diseases.

Pharmaceutical Compositions

Pharmaceutical compositions according to the present invention comprise the compounds of the invention in association with a pharmaceutically acceptable diluent or carrier.

As used herein, the term pharmaceutical composition refers to a mixture of one or more of the compounds described herein, or physiologically/pharmaceutically acceptable salts, solvates, N-oxides, stereoisomers, deuterated derivatives thereof or prodrugs thereof, with other chemical components, such as physiologically/pharmaceutically acceptable carriers and excipients. The purpose of a pharmaceutical composition is to facilitate administration of a compound to an organism.

As used herein, a physiologically/pharmaceutically acceptable diluent or carrier refers to a carrier or diluent that does not cause significant irritation to an organism and does not abrogate the biological activity and properties of the administered compound.

The present invention also provides pharmaceutical compositions which comprise, as an active ingredient, at least a compound of Formula (I) or a pharmaceutically acceptable salt thereof in association with a pharmaceutically acceptable excipient such as a carrier or diluent. The active ingredient may comprise 0.001% to 99% by weight, preferably 0.01% to 90% by weight, of the composition depending upon the nature of the formulation and whether further dilution is to be made prior to application. Preferably the compositions are made up in a form suitable for oral, inhalation, topical, nasal, rectal, percutaneous or injectable administration.

Pharmaceutical compositions suitable for the delivery of compounds of the invention and methods for their preparation will be readily apparent to those skilled in the art. Such compositions and methods for their preparation can be found, for example, in Remington: The Science and Practice of Pharmacy, 21st Edition, Lippincott Williams & Wilkins, Philadelphia, Pa., 2001.

The pharmaceutically acceptable excipients which are admixed with the active compound or salts of such compound, to form the compositions of this invention are well-known per se and the actual excipients used depend inter alia on the intended method of administering the compositions. Examples, without limitation, of excipients include calcium carbonate, calcium phosphate, various sugars and types of starch, cellulose derivatives, gelatin, vegetable oils and polyethylene glycols.

i) Oral Administration

The compounds of the invention may be administered orally (peroral administration; per os (latin)). Oral administration involve swallowing, so that the compound is absorbed from the gut and delivered to the liver via the portal circulation (hepatic first pass metabolism) and finally enters the gastrointestinal (GI) tract.

Compositions for oral administration may take the form of tablets, retard tablets, sublingual tablets, capsules, inhalation aerosols, inhalation solutions, dry powder inhalation, or liquid preparations, such as mixtures, solutions, elixirs, syrups or suspensions, all containing the compound of the invention; such preparations may be made by methods well-known in the art. The active ingredient may also be presented as a bolus, electuary or paste.

Where the composition is in the form of a tablet, any pharmaceutical carrier routinely used for preparing solid formulations may be used. Examples of such carriers include magnesium stearate, talc, gelatine, acacia, stearic acid, starch, lactose and sucrose.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent.

Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmel lose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet. Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant. Tablet blends may be compressed directly or by roller to form tablets. Tablet blends or portions of blends may alternatively be wet-, dry-, or melt-granulated, melt congealed, or extruded before tabletting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., 1980.

Where the composition is in the form of a capsule, any routine encapsulation is suitable, for example using the aforementioned carriers in a hard gelatine capsule. Where the composition is in the form of a soft gelatine capsule any pharmaceutical carrier routinely used for preparing dispersions or suspensions may be considered, for example aqueous gums, celluloses, silicates or oils, and are incorporated in a soft gelatine capsule. Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent. Liquid formulations may also be prepared by the reconstitution of a solid, for example, from a sachet.

ii) Oral Mucosal Administration

The compounds of the invention can also be administered via the oral mucosal. Within the oral mucosal cavity, delivery of drugs is classified into three categories: (a) sublingual delivery, which is systemic delivery of drugs through the mucosal membranes lining the floor of the mouth, (b) buccal delivery, which is drug administration through the mucosal membranes lining the cheeks (buccal mucosa), and (c) local delivery, which is drug delivery into the oral cavity.

Pharmaceutical products to be administered via the oral mucosal can be designed using mucoadhesive, quick dissolve tablets and solid lozenge formulations, which are formulated with one or more mucoadhesive (bioadhesive) polymers (such as hydroxy propyl cellulose, polyvinyl pyrrolidone, sodium carboxymethyl cellulose, hydroxy propyl methyl cellulose, hydroxy ethyl cellulose, polyvinyl alcohol, polyisobutylene or polyisoprene); and oral mucosal permeation enhancers (such as butanol, butyric acid, propranolol, sodium lauryl sulphate and others)

iii) Inhaled Administration

The compounds of the invention can also be administered by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. Each capsule or cartridge may generally contain between 0.001-50 mg, more preferably 0.01-5 mg of active ingredient or the equivalent amount of a pharmaceutically acceptable salt thereof. Alternatively, the active ingredient (s) may be presented without excipients.

Packaging of the formulation may be suitable for unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices.

For inhalers of the first type, single doses have been weighed by the manufacturer into small containers, which are mostly hard gelatine capsules. A capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients.

Other drawbacks related to the use of hard gelatine capsules for inhalation powders are (a) poor protection against moisture uptake from the ambient air, (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported (e.g. Nielsen et al, 1997).

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e.g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (Ex. EP0069715) or disks (Ex. GB 2041763; EP 0424790; DE 4239402 and EP 0674533), rotatable cylinders (Ex. EP 0166294; GB 2165159 and WO 92/09322) and rotatable frustums (Ex. WO 92/00771), all having cavities which have to be filled with powder from the container. Other multi dose devices have measuring slides (Ex. U.S. Pat. No. 5,201,308 and WO 97/00703) or measuring plungers with a local or circumferential recess to displace a certain volume of powder from the container to a delivery chamber or an air conduit (Ex. EP 0505321, WO 92/04068 and WO 92/04928), or measuring slides such as the Genuair® (formerly known as Novolizer SD2FL), which is described the following patent applications Nos: WO97/000703, WO03/000325 and WO2006/008027.

Reproducible dose measuring is one of the major concerns for multi dose inhaler devices.

The powder formulation has to exhibit good and stable flow properties, because filling of the dose measuring cups or cavities is mostly under the influence of the force of gravity.

For reloaded single dose and multiple unit dose inhalers, the dose measuring accuracy and reproducibility can be guaranteed by the manufacturer. Multi dose inhalers on the other hand, can contain a much higher number of doses, whereas the number of handlings to prime a dose is generally lower.

Because the inspiratory air stream in multi-dose devices is often straight across the dose measuring cavity, and because the massive and rigid dose measuring systems of multi dose inhalers can not be agitated by this inspiratory air stream, the powder mass is simply entrained from the cavity and little de-agglomeration is obtained during discharge.

Consequently, separate disintegration means are necessary. However in practice, they are not always part of the inhaler design. Because of the high number of doses in multi-dose devices, powder adhesion onto the inner walls of the air conduits and the de-agglomeration means must be minimized and/or regular cleaning of these parts must be possible, without affecting the residual doses in the device. Some multi dose inhalers have disposable drug containers that can be replaced after the prescribed number of doses has been taken (Ex. WO 97/000703). For such semi-permanent multi dose inhalers with disposable drug containers, the requirements to prevent drug accumulation are even stricter.

Apart from applications through dry powder inhalers the compositions of the invention can be administered in aerosols which operate via propellant gases or by means of so-called atomisers, via which solutions of pharmacologically-active substances can be sprayed under high pressure so that a mist of inhalable particles results. The advantage of these atomisers is that the use of propellant gases can be completely dispensed with. Such atomiser is the Respimat® which is described, for example, in PCT Patent Applications Nos. WO 91/14468 and WO 97/12687, reference here is being made to the contents thereof.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the active ingredient (s) and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant.

The aerosol composition may be excipient free or may optionally contain additional formulation excipients well known in the art such as surfactants (e.g. oleic acid or lecithin) and cosolvens (e.g. ethanol). Pressurised formulations will generally be retained in a canister (e.g. an aluminium canister) closed with a valve (e.g. a metering valve) and fitted into an actuator provided with a mouthpiece.

Medicaments for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline.

Achieving high dose reproducibility with micronised powders is difficult because of their poor flowability and extreme agglomeration tendency. To improve the efficiency of dry powder compositions, the particles should be large while in the inhaler, but small when discharged into the respiratory tract. Thus, an excipient such as lactose or glucose is generally employed. The particle size of the excipient will usually be much greater than the inhaled medicament within the present invention. When the excipient is lactose it will typically be present as milled lactose, preferably crystalline alpha lactose monohydrate.

Pressurized aerosol compositions will generally be filled into canisters fitted with a valve, especially a metering valve. Canisters may optionally be coated with a plastics material e.g. a fluorocarbon polymer as described in WO96/32150. Canisters will be fitted into an actuator adapted for buccal delivery.

iv) Nasal Mucosal Administration

The compounds of the invention may also be administered via the nasal mucosal.

Typical compositions for nasal mucosa administration are typically applied by a metering, atomizing spray pump and are in the form of a solution or suspension in an inert vehicle such as water optionally in combination with conventional excipients such as buffers, anti-microbials, tonicity modifying agents and viscosity modifying agents.

v) Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art. The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

vi) Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and microneedle or needle-free injection.

Formulations for topical administration may be formulated to be immediate and/or modified release. Modified release formulations include delayed-, sustained-, pulsed-, controlled-, targeted and programmed release.

vii) Rectal/Intravaginal Administration

Compounds of the invention may be administered rectally or vaginally, for example, in the form of a suppository, pessary, or enema. Cocoa butter is a traditional suppository base, but various alternatives may be used as appropriate. Formulations for rectal/vaginal administration may be formulated to be immediate and/or modified release. Modified release formulations include delayed-, sustained-, pulsed-, controlled-, targeted and programmed release.

viii) Ocular Administration

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable {e.g. absorbable gel sponges, collagen) and nonbiodegradable (e.g. silicone) implants, wafers, lenses and particulate or vesicular systems, such as niosomes or liposomes. A polymer such as crossed-linked polyacrylic acid, polyvinyl-alcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

ix) Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

The amount of the active compound administered will be dependent on the subject being treated, the severity of the disorder or condition, the rate of administration, the disposition of the compound and the discretion of the prescribing physician. However, an effective dosage is typically in the range of 0.01-3000 mg, more preferably 0.5-1000 mg of active ingredient or the equivalent amount of a pharmaceutically acceptable salt thereof per day. Daily dosage may be administered in one or more treatments, preferably from 1 to 4 treatments, per day.

Preferably, the the pharmaceutical compositions of the invention are made up in a form suitable for oral, inhalation or topical administration.

The pharmaceutical formulations may conveniently be presented in unit dosage form and may be prepared by any of the methods well known in the art of pharmacy.

Preferably the composition is in unit dosage form, for example a tablet, capsule or metered aerosol dose, so that the patient may administer a single dose.

The amount of each active which is required to achieve a therapeutic effect will, of course, vary with the particular active, the route of administration, the subject under treatment, and the particular disorder or disease being treated.

Formulation Examples

The following preparations forms are cited as formulation examples:

Formulation Example 1 (Oral Suspension)

| Ingredient | Amount |
| --- | --- |
| Active Compound | 3 mg |
| Citric acid | 0.5 g |
| Sodium chloride | 2.0 g |
| Methyl paraben | 0.1 g |
| Granulated sugar | 25 g |

-continued

| Ingredient | Amount |
| --- | --- |
| Sorbitol (70% solution) | 11 g |
| Veegum K | 1.0 g |
| Flavoring | 0.02 g |
| Dye | 0.5 mg |
| Distilled water | q.s. to 100 mL |

Formulation Example 2 (Hard Gelatine Capsule for Oral Administration)

| Ingredient | Amount |
| --- | --- |
| Active Compound | 1 mg |
| Lactose | 150 mg |
| Magnesium stearate | 3 mg |

Formulation Example 3 (Gelatin Cartridge for Inhalation)

| Ingredient | Amount |
| --- | --- |
| Active Compound (micronized) | 0.2 mg |
| Lactose | 25 mg |

Formulation Example 4 (Formulation for Inhalation with a DPI)

| Ingredient | Amount |
| --- | --- |
| Active Compound (micronized) | 15 mg |
| Lactose | 3000 mg |

Formulation Example 5 (Formulation for a MDI)

| Ingredient | Amount |
| --- | --- |
| Active Compound (micronized) | 10 g |
| 1,1,1,2,3,3,3-heptafluoro-n-propane | q.s. to 200 mL |

Formulation Example 6 (Topical Formulation)

| Ingredient | Amount |
| --- | --- |
| Active compound | 1% |
| Cetyl alcohol | 3% |
| Stearyl alcohol | 4% |
| Glyceryl monostearate | 4% |
| Sorbitan monostearate | 0.8% |
| Sorbitan monostearate POE | 0.8% |
| Liquid Vaseline | 0.8% |
| Glycerine | 15% |

-continued

| Ingredient | Amount |
| --- | --- |
| Preservative | 0.2% |
| Purified water | add to 100% |

Modifications, which do not affect, alter, change or modify the essential aspects of the compounds, combinations or pharmaceutical compositions described, are included within the scope of the present invention.

The invention claimed is:

1. A compound of Formula (I), or a pharmaceutically acceptable salt, N-oxide, or isotopically-labeled derivative thereof:

Formula (I)

wherein:
X is independently chosen from a —N= and —CR$^C$=;
R$_1$ is —R$^d$ or —O—R$^d$;
R$_2$ and R$_3$ are independently chosen from a hydrogen atom, a linear or branched C$_{1-4}$ alkyl group, a linear or branched C$_{1-4}$ hydroxyalkyl group, a monocyclic C$_{3-7}$ cycloalkyl group optionally substituted with one or more substituents chosen from a linear or branched C$_{1-4}$ alkyl group and amino group, a monocyclic 4-to 7-membered heterocyclyl containing at least one heteroatom chosen from N, S, and O, a linear or branched C$_{1-4}$ alkylsulfonyl group, —(CH$_2$)$_p$—CO—(CH$_2$)$_q$—NH$_2$ group, —(CH$_2$)$_r$—NR$^a$R$^b$ group, —(CH$_2$)$_p$—R$^e$ group, —SO$_2$—NR$^a$R$^b$ group, and —CO—CF$_3$ group;
R$_4$ is chosen from a linear or branched C$_{1-4}$ alkyl group optionally substituted with one or more substituents chosen from a halogen atom, —(CH$_2$)$_p$—CO—(CH$_2$)$_q$—NH$_2$ group, a linear or branched C$_{1-4}$ hydroxyalkyl group, a linear or branched C$_{1-4}$ aminoalkyl group, (C$_{1-2}$ alkoxy)-(C$_{1-2}$)alkyl group, —(CH$_2$)$_p$—R$^e$ group, and —(CH$_2$)$_r$—NR$^a$R$^b$ group;
R$_5$ is chosen from a hydrogen atom and a halogen atom;
R$^a$ and R$^b$ are independently chosen from a hydrogen atom or a linear or branched C$_{1-4}$ alkyl group, or R$^a$ and R$^b$ together with N form a monocyclic 4 to 7-membered heterocyclyl and optionally containing at least one further heteroatom chosen from N, S, and O;
R$^c$ is chosen from a hydrogen atom, a halogen atom, a linear or branched C$_{1-4}$ alkyl group and a linear or branched C$_{1-4}$ alkoxy group;
R$^d$ is chosen from a linear or branched C$_{1-6}$ haloalkyl group;
R$^e$ is chosen from a monocyclic 6 to 8-membered heteroaryl group containing at least one heteroatom chosen from N, S and O, a monocyclic 3 to 8-membered heterocyclyl group containing at least one heteroatom chosen from N, S, and O, and optionally substituted with one or more substituents chosen from a linear or branched C$_{1-4}$ alkyl group;
p and q are independently 0, 1 or 2; and
r is 1, 2, 3 or 4.

2. The compound according to claim 1, wherein X is —CR$^C$=, and wherein R$^c$ is independently chosen from a hydrogen atom and a halogen atom.

3. The compound according to claim 2, wherein R$^c$ is chosen from a hydrogen atom and a fluorine atom.

4. The compound according to claim 1, wherein R$_1$ is —R$^d$ or —O—R$^d$, and wherein R$^d$ is a linear or branched C$_{1-3}$ fluoroalkyl group.

5. The compound according to claim 1, wherein R$_2$ and R$_3$ are independently chosen from a hydrogen atom, a linear or branched C$_{1-4}$ alkyl group, a linear or branched C$_{1-4}$ hydroxyalkyl group, —(CH$_2$)$_p$—R$^e$ group and —SO$_2$—NR$^a$R$^b$ group, R$^a$ and R$^b$ are independently chosen from a hydrogen atom or a C$_{1-2}$ alkyl group, and wherein R$^e$ is a monocyclic 4 to 6-membered N-containing heterocyclyl group and optionally substituted with a methyl group.

6. The compound according to claim 5, wherein R$_2$ and R$_3$ are independently chosen from a hydrogen atom, a methyl group, and a C$_{1-2}$ hydroxyalkyl group.

7. The compound according to claim 6, wherein R$_2$ and R$_3$ are hydrogen atom.

8. The compound according to claim 1, wherein R$_4$ is chosen from a linear or branched C$_{1-4}$ alkyl group optionally substituted with one or more substituents chosen from a halogen atom, —(CH$_2$)—CO—NH$_2$ group and a linear C$_{1-3}$ hydroxyalkyl group.

9. The compound according to claim 8, wherein R$_4$ is chosen from a methyl group and a —CH$_2$CF$_3$ group.

10. The compound according to claim 1, wherein R$_5$ is chosen from a hydrogen atom and a fluorine atom.

11. The compound according to claim 1, wherein
X is independently chosen from a —N= and —CR$^C$=,
R$_1$ is —R$^d$ or —O—R$^d$,
R$_2$ and R$_3$ are independently chosen from a hydrogen atom, a methyl group, a linear C$_{2-3}$ hydroxyalkyl group, a cyclohexyl group substituted with an amino group, a O-containing monocyclic 6-membered heterocyclyl group, a C$_{1-2}$ alkylsulfonyl group, —(CH$_2$)$_p$—CO—(CH$_2$)$_q$—NH$_2$ group, —(CH$_2$)$_r$—NR$^a$R$^b$ group, —(CH$_2$)$_p$—R$^e$ group, —SO$_2$—NR$^a$R$^b$ group, and —CO—CF$_3$ group,
R$_4$ is chosen from a linear or branched C$_{1-4}$ alkyl group optionally substituted with one or more substituents chosen from a fluorine atom, —(CH$_2$)—CO—NH$_2$ group, a linear C$_{2-3}$ hydroxyalkyl group, an aminopropyl group, a methoxyethyl group, —(CH$_2$)$_p$—R$^e$ group and —(CH$_2$)$_r$—NR$^a$R$^b$ group,
R$_5$ is chosen from a hydrogen atom and halogen atom,
R$^a$ and R$^b$ are independently chosen from a hydrogen atom or C$_{1-2}$ alkyl group, or R$^a$ and R$^b$ together with N form a monocyclic 4-to 6-membered heterocyclyl and optionally containing at least one further heteroatom selected from O,
is independently chosen from a hydrogen atom, a fluorine atom, and a methoxy group,
R$^d$ is chosen from a linear or branched C$_{1-3}$ fluoroalkyl group,
R$^e$ is chosen from a monocyclic 6-membered heteroaryl group containing N as heteroatom or a monocyclic 6-membered heterocyclyl group containing N as heteroatom and optionally substituted with a methyl group, p and q are independently chosen from 0, 1 or 2, and r is 2.

12. The compound according to claim 1, wherein
X is —$CR^C$=, wherein $R^c$ is independently chosen from a hydrogen atom and a fluorine atom,
$R_1$ is —$R^d$ or —O—$R^d$, wherein $R^d$ is chosen from a linear or branched $C_{2-3}$ fluoroalkyl group,
$R_2$ and $R_3$ are hydrogen,
$R_4$ is a methyl group, and
$R_5$ is a hydrogen atom.

13. The compound according to claim 1, wherein the compound is chosen from:
2-(3-amino-6-(5-fluoro-2-(2,2,3,3,3-pentafluoropropoxy)phenyl)-1H-indazol-1-yl)acetamide,
2-(3-amino-6-(5-fluoro-2-(2,2,2-trifluoroethoxy)phenyl)-1H-indazol-1-yl)acetamide,
6-(5-methoxy-2-(2,2,3,3,3-pentafluoropropoxy)phenyl)-1-methyl-1H-indazol-3-amine,
6-(5-fluoro-2-(2,2,3,3,3-pentafluoropropoxy)phenyl)-1-methyl-1H-indazol-3-amine,
2-(3-amino-6-(2-(2,2,3,3,3-pentafluoropropoxy)phenyl)-1H-indazol-1-yl)acetamide,
2-(3-amino-6-(2-(2,2,2-trifluoroethoxy)phenyl)-1H-indazol-1-yl)acetamide,
1-methyl-6-(2-(2,2,3,3,3-pentafluoropropoxy)phenyl)-1H-indazol-3-amine,
1-methyl-6-(2-(2,2,2-trifluoroethoxy)phenyl)-1H-indazol-3-amine,
6-(5-methoxy-2-(2,2,2-trifluoroethoxy)phenyl)-1-methyl-1H-indazol-3-amine,
6-(5-fluoro-2-(2,2,2-trifluoroethoxy)phenyl)-1-methyl-1H-indazol-3-amine,
2-(1-methyl-6-(2-(2,2,2-trifluoroethoxy)phenyl)-1H-indazol-3-ylamino)acetamide,
2-(1-methyl-6-(2-(2,2,3,3,3-pentafluoropropoxy)phenyl)-1H-indazol-3-ylamino)ethanol,
2-(1-trifluoromethyl-6-(2-(2,2,2-trifluoroethoxy)phenyl)-1H-indazol-3-amine,
6-(2-(2,2,3,3,3-pentafluoropropoxy)phenyl)-1H-indazol-3-amine,
2-(3-amino-6-(2-(2,2,2-trifluoroethoxy)phenyl)-1H-indazol-1-yl)ethanol,
6-(5-fluoro-2-(2,2,3,3,3-pentafluoropropoxy)phenyl)-1H-indazol-3-amine,
3-(3-amino-6-(2-(2,2,3,3,3-pentafluoropropoxy)phenyl)-1H-indazol-1-yl) propan-1-ol,
3-(3-amino-6-(5-fluoro-2-(2,2,2-trifluoroethoxy)phenyl)-1H-indazol-1-yl) propan-1-ol,
3-(3-amino-6-(5-fluoro-2-(2,2,3,3,3-pentafluoropropoxy)phenyl)-1H-indazol-1-yl)propan-1-ol,
2-(6-(5-fluoro-2-(2,2,3,3,3-pentafluoropropoxy)phenyl)-3-(3-hydroxypropylamino)-1H-indazol-1-yl)acetamide,
6-(3-fluoro-2-(2,2,2-trifluoroethoxy)phenyl)-1-methyl-1H-indazol-3-amine,
6-(3-fluoro-2-(2,2,3,3,3-pentafluoropropoxy)phenyl)-1-methyl-1H-indazol-3-amine,
6-(4-fluoro-2-(2,2,3,3,3-pentafluoropropoxy)phenyl)-1-methyl-1H-indazol-3-amine,
6-(2-fluoro-6-(2,2,3,3,3-pentafluoropropoxy)phenyl)-1-methyl-1H-indazol-3-amine,
6-(2-fluoro-6-(2,2,2-trifluoroethoxy)phenyl)-1-methyl-1H-indazol-3-amine,
2-(3-amino-6-(3-fluoro-2-(2,2,3,3,3-pentafluoropropoxy)phenyl)-1H-indazol-1-yl)acetamide,
3-(1-methyl-6-(2-(2,2,3,3,3-pentafluoropropoxy)phenyl)-1H-indazol-3-ylamino)propan-1-ol,
2-(3-amino-6-(3-fluoro-2-(2,2,2-trifluoroethoxy)phenyl)-1H-indazol-1-yl)acetamide,
2-(3-amino-6-(4-fluoro-2-(2,2,3,3,3-pentafluoropropoxy)phenyl)-1H-indazol-1-yl)acetamide,
2-(3-amino-6-(4-fluoro-2-(2,2,2-trifluoroethoxy)phenyl)-1H-indazol-1-yl)acetamide,
2-(3-amino-6-(2-fluoro-6-(2,2,2-trifluoroethoxy)phenyl)-1H-indazol-1-yl)acetamide,
2,2'-(1-methyl-6-(2-(2,2,2-trifluoroethoxy)phenyl)-1H-indazol-3-ylazanediyl)diethanol,
3-(3-amino-6-(3-fluoro-2-(2,2,2-trifluoroethoxy)phenyl)-1H-indazol-1-yl) propan-1-ol,
3-(3-amino-6-(3-fluoro-2-(2,2,3,3,3-pentafluoropropoxy)phenyl)-1H-indazol-1-yl)propan-1-ol,
3-((1-methyl-6-(2-(2,2,2-trifluoroethoxy)phenyl)-1H-indazol-3-yl)amino)-3-oxopropan-1-amine,
3-((6-(5-fluoro-2-(2,2,2-trifluoroethoxy)phenyl)-1-methyl-1H-indazol-3-yl)amino)-3-oxopropan-1-amine,
N-1-(6-(5-fluoro-2-(2,2,3,3,3-pentafluoropropoxy)phenyl)-1-methyl-1H-indazol-3-yl)-N2-methylethane-1,2-diamine,
3-(3-amino-6-(2-fluoro-6-(2,2,2-trifluoroethoxy)phenyl)-1H-indazol-1-yl) propan-1-ol,
3-(3-amino-6-(2-(2,2-difluoroethoxy)-6-fluorophenyl)-1H-indazol-1-yl)propan-1-ol,
6-(3-methoxy-2-(2,2,2-trifluoroethoxy)phenyl)-1-methyl-1H-indazol-3-amine,
6-(2-(2,2-difluoroethoxy)-3-methoxyphenyl)-1-methyl-1H-indazol-3-amine,
6-(2-(2,2-difluoroethoxy)-3-fluorophenyl)-1-methyl-1H-indazol-3-amine,
3-(3-amino-6-(2-(2,2-difluoroethoxy)phenyl)-1H-indazol-1-yl)propan-1-ol,
6-(3-fluoro-2-(2,2,2-trifluoroethoxy)phenyl)-1-methyl-N-((1-methylpiperidin-4-yl)methyl)-1H-indazol-3-amine,
N-1-(6-(3-fluoro-2-(2,22-trifluoroethoxy)phenyl)-1-methyl-1H-indazol-3-yl)-N2-methylethane-1,2-diamine,
6-(3-fluoro-2-(2,2,2-trifluoroethoxy)phenyl)-1-methyl-N,N-bis(2-(piperidin-4-yl)ethyl)-1H-indazol-3-amine,
1-methyl-6-(2-(2,2,2-trifluoroethoxy)pyridin-3-yl)-1H-indazol-3-amine,
3-(3-amino-6-(3-fluoro-2-(2,2,2-trifluoroethoxy)phenyl)-1H-indazol-1-yl)propane-1,2-diol,
6-(2-(2,2-difluoroethoxy)pyridin-3-yl)-1-methyl-1H-indazol-3-amine,
N-(6-(3-fluoro-2-(2,2,2-trifluoroethoxy)phenyl)-1-methyl-1H-indazol-3-yl)sulfonamide,
1-(3-aminopropyl)-6-(3-fluoro-2-(2,2,2-trifluoroethoxy)phenyl)-1H-indazol-3-amine,
3-(3-amino-6-(2-fluoro-6-(2,2,2-trifluoroethoxy)phenyl)-1H-indazol-1-yl)propane-1,2-diol,
N-(6-(3-fluoro-2-(2,2,2-trifluoroethoxy)phenyl)-1-methyl-1H-indazol-3-yl)methanesulfonamide,
N-(6-(3-fluoro-2-(2,2,2-trifluoroethoxy)phenyl)-1-methyl-1H-indazol-3-yl)ethanesulfonamide,
6-(2-(2,2-difluoroethoxy)-3-fluorophenyl)-N,N,1-trimethyl-1H-indazol-3-amine,
N-(6-(2-(2,2-difluoroethoxy)-3-fluorophenyl)-1-methyl-1H-indazol-3-yl)-2,2,2-trifluoroacetamide,
6-(2-(2,2-difluoroethoxy)-3-fluorophenyl)-N,1-dimethyl-1H-indazol-3-amine,
6-(2-(difluoromethoxy)-3-fluorophenyl)-1-methyl-1H-indazol-3-amine, N-methyl-N'-(6-(3-fluoro-2-(2,2,2-trifluoroethoxy)phenyl)-1-methyl-1H-indazol-3-yl)sulfamide,
1-methyl-6-(2-(trifluoromethoxy)phenyl)-1H-indazol-3-amine,
2-(3-amino-6-(2-(trifluoromethoxy)phenyl)-1H-indazol-1-yl)acetamide,
2-(1-(2-amino-2-oxoethyl)-6-(2-(trifluoromethoxy)phenyl)-1H-indazol-3-ylamino)acetamide,
2-(3-(2-hydroxyethylamino)-6-(2-(trifluoromethoxy)phenyl)-1H-indazol-1-yl)acetamide,
2-(3-amino-6-(2-(trifluoromethyl)phenyl)-1H-indazol-1-yl)acetamide,
2-(3-((2-aminoethyl)amino)-6-(2-(trifluoromethoxy)phenyl)-1H-indazol-1-yl)acetamide,
2-(3-amino-6-(2-(trifluoromethoxy)phenyl)-1H-indazol-1-yl)ethanol,
3-(3-amino-6-(2-(trifluoromethyl)phenyl)-1H-indazol-1-yl)propan-1-ol,
3-(3-amino-6-(2-(trifluoromethoxy)phenyl)-1H-indazol-1-yl)propan-1-ol,
1-(3-aminopropyl)-6-(2-(trifluoromethoxy)phenyl)-1H-indazol-3-amine,
1-methyl-6-(2-(trifluoromethyl)phenyl)-1H-pyrazolo[3,4-b]pyridin-3-amine,
3-(3-amino-6-(2-(trifluoromethyl)phenyl)-1H-pyrazolo[3,4-b]pyridin-1-yl) propan-1-ol,
6-(3-fluoro-2-(trifluoromethyl)phenyl)-1-methyl-1H-indazol-3-amine,
1-methyl-6-(2-(trifluoromethyl)phenyl)-1H-pyrazolo[3,4-b]pyrazin-3-amine,
1-methyl-6-(2-(trifluoromethyl)pyridin-3-yl)-1H-indazol-3-amine,
N,N-dimethyl-N'-(6-(3-fluoro-2-(2,2,2-trifluoroethoxy)phenyl)-1-methyl-1H-indazol-3-yl)sulfamide,
N-(6-(3-fluoro-2-(2,2,2-trifluoroethoxy)phenyl)-1-methyl-1H-indazol-3-yl)piperidine-1-sulfonamide,
6-(2-fluoro-6-(2,2,2-trifluoroethoxy)phenyl)-1-methyl-1H-pyrazolo[3,4-b]pyrazin-3-amine,
1-(3-aminopropyl)-6-(3-fluoro-2-(2,2,3,3,3-pentafluoropropoxy)phenyl)-1H-indazol-3-amine,
1-methyl-6-(3-(2,2,2-trifluoroethoxy)pyridin-4-yl)-1H-indazol-3-amine,
1-isopropyl-6-(2-(trifluoromethoxy)phenyl)-1H-indazol-3-amine,
1-isobutyl-6-(2-(trifluoromethoxy)phenyl)-1H-indazol-3-amine,
1-(2-methoxyethyl)-6-(2-(trifluoromethoxy)phenyl)-1H-indazol-3-amine,
1-(pyridin-3-ylmethyl)-6-(2-(trifluoromethoxy)phenyl)-1H-indazol-3-amine,
1-ethyl-6-(2-(trifluoromethoxy)phen yl)-1H-indazol-3-amine,
N-(6-(3-fluoro-2-(2,2,2-trifluoroethoxy)phenyl)-1-methyl-1H-indazol-3-yl)morpholine-4-sulfonamide,
N-(6-(3-fluoro-2-(2,2,2-trifluoroethoxy)phenyl)-1-methyl-1H-indazol-3-yl)azetidine-1-sulfonamide,
6-(3-fluoro-2-(2,2,3,3,3-pentafluoropropoxy)phenyl)-1-methyl-N-(tetrahydro-2H-pyran-4-yl)-1H-indazol-3-amine,
$N^1$-(6-(3-fluoro-2-(2,2,3,3,3-pentafluoropropoxy)phenyl)-1-methyl-1H-indazol-3-yl)cyclohexane-1,4-diamine,
N-(6-(3-fluoro-2-(2,2,2-trifluoroethoxy)phenyl)-1-methyl-1H-indazol-3-yl)-N-(methylsulfonyl)methanesulfonamide,
1-(3-(dimethylamino)propyl)-6-(3-fluoro-2-(2,2,2-trifluoroethoxy)phenyl)-1H-indazol-3-amine,
6-(3-fluoro-2-(2,2,2-trifluoroethoxy)phenyl)-1-methyl-1H-pyrazolo[4,3-b]pyridin-3-amine,
6-(3-fluoro-2-(2,2,2-trifluoroethoxy)phenyl)-4-methoxy-1-methyl-1H-indazol-3-amine,
4-fluoro-6-(3-fluoro-2-(2,2,2-trifluoroethoxy)phenyl)-1-methyl-1H-indazol-3-amine,
or a pharmaceutically acceptable salt, N-oxide, or isotopically-labeled derivative thereof.

14. A pharmaceutical composition comprising the compound according to claim 1 and a pharmaceutically acceptable diluent or carrier.

15. A combination product for simultaneous, separate, or sequential use in the treatment of the human or animal body comprising (i) the compound according to claim 1; and at least one additional compound chosen from:
(a) Opioid receptor agonists,
(b) Opioid receptor partial agonists,
(c) NSAIDS,
(d) COX-2 inhibitors,
(e) Ion channel modulators,
(f) Centrally acting agents,
(g) Agents for neuropathic pain,
(h) Agents for cancer pain,
(i) Anti-fibrotics,
(j) Prostacyclin analogues,
(k) Endothelin antagonists,
(l) Phosphodiesterase V inhibitors,
(m) Guanylate cyclase stimulators,
(n) Oral and inhaled corticosteroids,
(o) Phosphodiesterase IV inhibitors,
(p) Beta2-adrenoceptor agonists,
(q) Muscarinic antagonists,
(r) Xanthines,
(s) Mast cell stabilizers,
(t) Leukotriene modifiers,
(u) Th2 cytokine inhibitors,
(v) Thromboxane antagonists/thromboxane synthase inhibitors,
(w) Anti-IgE therapy compounds,
(x) Histamine antagonists,
(y) Antiinflammatory agents,
(z) JAK inhibitors,
(aa) Syk inhibitors,
(ab) Immunosupressants,
(ac) Antipruritic agents, and
(ad) Anti-tussive agents, Decongestants, Mucolytics, Expectorants, or Proton Pump Inhibitors.

16. A method for treating a subject afflicted with a pathological condition or a disease mediated by modulation of voltage-gated sodium channels comprising administering to said subject an effective amount of the compound according to claim 1, wherein the pathological condition or disease is chosen from pain, idiopathic cough, chronic cough, cough related to respiratory diseases, respiratory diseases, itch, dermatological diseases, epilepsy, squizophrenia and bipolar disorder.

17. The method according to claim 16, wherein the pain disease is chosen from acute pain, chronic pain, inflammatory pain, visceral pain, nociceptive pain, neurophatic pain, postherpetic pain, trigeminal neuralgia, diabetic neuropathy, chronic back pain, chronic pelvic pain, migraine and pain resulting from cancer and chemotherapy.

18. The method of claim 16, wherein the voltage-gated sodium channel is Nav1.7.

19. A method for treating a subject afflicted with a pathological condition or disease mediated by modulation of voltage-gated sodium channels comprising administering to said subject an effective amount of the compound according to claim 1.

20. The method of claim 19, wherein the voltage-gated sodium channel is Nav1.7.

* * * * *

UNITED STATES PATENT AND TRADEMARK OFFICE
CERTIFICATE OF CORRECTION

PATENT NO. : 10,173,985 B2  
APPLICATION NO. : 15/559120  
DATED : January 8, 2019  
INVENTOR(S) : Laia Sole Feu and Silvia Fonquerna Pou Page 1 of 1

It is certified that error appears in the above-identified patent and that said Letters Patent is hereby corrected as shown below:

In the Claims

Claim 7, Column 70, Line 26, "are hydrogen atom." should read --are hydrogen.--.

Claim 11, Column 70, Line 59, "is independently chosen from a hydrogen atom, a fluorine" should read --$R^c$ is independently chosen from a hydrogen atom, a fluorine--.

Claim 13, Column 72, Line 39, "N-1-(6-(3-fluoro-2-(2,22-trifluoroethoxy)phenyl)-1-" should read --N-1-(6-(3-fluoro-2-(2,2,2-trifluoroethoxy)phenyl)-1- --.

Signed and Sealed this  
Fifth Day of March, 2019

Andrei Iancu  
*Director of the United States Patent and Trademark Office*